(12) United States Patent
Kizhakkedathu et al.

(10) Patent No.: US 11,459,434 B2
(45) Date of Patent: Oct. 4, 2022

(54) ANTIFOULING POLYMERIC COATING COMPOSITIONS

(71) Applicant: The University of British Columbia, Vancouver (CA)

(72) Inventors: Jayachandran N. Kizhakkedathu, New Westminster (CA); Dirk Lange, Vancouver (CA); Joey Lo, Richmond (CA); Yan Mei, Vancouver (CA); Kai Yu, Vancouver (CA)

(73) Assignee: The University of British Columbia, Vancouver (CA)

( * ) Notice: Subject to any disclaimer, the term of this patent is extended or adjusted under 35 U.S.C. 154(b) by 345 days.

(21) Appl. No.: 15/574,787

(22) PCT Filed: May 26, 2016

(86) PCT No.: PCT/CA2016/000157
§ 371 (c)(1),
(2) Date: Apr. 11, 2018

(87) PCT Pub. No.: WO2016/187698
PCT Pub. Date: Dec. 1, 2016

(65) Prior Publication Data
US 2018/0147326 A1    May 31, 2018

Related U.S. Application Data

(60) Provisional application No. 62/166,255, filed on May 26, 2015.

(51) Int. Cl.
| | | |
|---|---|---|
| *A61L 29/14* | (2006.01) | |
| *A61L 29/08* | (2006.01) | |
| *C09D 165/00* | (2006.01) | |
| *C09D 5/16* | (2006.01) | |
| *C08J 7/04* | (2020.01) | |
| *C08J 7/046* | (2020.01) | |
| *C08L 33/26* | (2006.01) | |
| *A61L 27/34* | (2006.01) | |
| *A61L 31/10* | (2006.01) | |
| *C09D 133/06* | (2006.01) | |
| *C08J 7/056* | (2020.01) | |

(52) U.S. Cl.
CPC ............. *C08J 7/046* (2020.01); *A61L 27/34* (2013.01); *A61L 29/085* (2013.01); *A61L 29/14* (2013.01); *A61L 31/10* (2013.01); *C08J 7/0427* (2020.01); *C08J 7/056* (2020.01); *C08L 33/26* (2013.01); *C09D 5/16* (2013.01); *C09D 5/1662* (2013.01); *C09D 133/06* (2013.01); *C09D 165/00* (2013.01); *A61L 2400/10* (2013.01); *A61L 2420/02* (2013.01); *C08G 2261/3221* (2013.01); *C08G 2261/3241* (2013.01); *C08J 2433/26* (2013.01)

(58) Field of Classification Search
CPC ....... C08L 65/00; C08L 33/26; C09D 133/26; C09D 133/06; C09D 165/00; C09D 5/16; C09D 5/1662; A61L 2400/10; A61L 2420/02; A61L 27/34; A61L 29/085; A61L 29/14; A61L 31/10; C08G 2261/3221; C08G 2261/3241; C08J 2433/26; C08J 7/0427; C08J 7/047; C08J 7/056; C08J 7/042
See application file for complete search history.

(56) References Cited

U.S. PATENT DOCUMENTS

| | | |
|---|---|---|
| 8,962,772 B2 | 2/2015 | Ding et al. |
| 2010/0051538 A1 | 3/2010 | Freeman et al. |
| 2015/0217237 A1 | 8/2015 | Abetz et al. |

FOREIGN PATENT DOCUMENTS

| | | | | |
|---|---|---|---|---|
| CN | 104530314 | | 4/2015 | |
| WO | 2002060505 | | 8/2002 | |
| WO | WO 02/060505 | * | 8/2002 | ............. A61L 27/00 |
| WO | 2010006196 | | 1/2010 | |
| WO | 2011005258 | | 1/2011 | |
| WO | 2014118382 | | 8/2014 | |
| WO | WO2014/118382 | * | 8/2014 | ............. A61L 27/43 |
| WO | 2016022796 | | 2/2016 | |

OTHER PUBLICATIONS

Chen et al., (2015) "Assembly of poly(dopamine) / poly (acrylamide) mixed coatings by single-step surface modification strategy and its application to the separation of proteins using capillary electrophoresis," J. Sep. Sci., 38: 2915-2923.
Zhou et al., (2014) "Fabrication of antifouling membrane surface by poly (sulfobetaine methacrylate)/ polydopamine co-deposition," Journal of Membrane Science, 466: 18-25.
Kizhakkedathu et al., (2015) "Self-assembly as a Design Principle in the Development of Binary Antithrombotic anti Antimicrobial Coating," UBC, 1-38.
Liu et al., (2014) "Dopamine-Assisted Deposition of Dextran for Nonfouling Applications," Langmuir, 30: 3118-3126.
Wu et al. (2012) "Investigation of the Hydration of Nonfouling Material Poly(sulfobetaine methacrylate) by Low-Field Nuclear Magnetic Resonance," Langmuir, 28: 7436-7441.

* cited by examiner

*Primary Examiner* — Anna R Falkowitz
(74) *Attorney, Agent, or Firm* — Rudy J. Ng; Bozicevic, Field & Francis LLP

(57) ABSTRACT

Provided herein are compositions comprising: (a) a polymeric catechol binder, such as: polymeric dopamine, polymeric norepinephrine, polymeric epinephrine; polymeric pyrogallol, polymeric tannic acid, polymeric hydroxyhydroquinone, polymeric catechin, polymeric epigallocatechin etc.; and (b) a hydrophilic polymer, methods for using the compositions to coat a substrate, and methods for making the compositions. In particular, the substrate may form part of an apparatus on which it would be beneficial to limit biofouling and/or protein binding.

17 Claims, 30 Drawing Sheets

$P$ = 0.19, no difference   $P$ = 0.0008, significant difference   $P$ = 0.004, significant difference

DA

NE

TA

PG

ANTIFOULING POLYMERIC COATING COMPOSITIONS

CROSS REFERENCE TO RELATED APPLICATIONS

This application claims the benefit of U.S. Provisional Patent Application Ser. No. 62/166,255 filed on 26 May 2015, entitled "ONE-STEP APPROACH TO UNIVERSAL ANTIFOULING COATINGS".

TECHNICAL FIELD

The present invention relates to catechol polymer and catechol derivative polymer coating field. In particular, the invention relates to catechol polymers or catechol derivative polymers in combination with certain hydrophilic polymers to form compositions, to provide methods for making the compositions and to provide uses for the compositions.

BACKGROUND

In an aging society, medical devices are increasingly used to improve a patients' quality of life and to extend their life expectancy. For example, intravascular catheters are used to deliver fluids or drugs into bloodstream, and urinary catheters are used to drain waste fluids from the body. In spite of their extensive use, medical devices, such as catheters, are associated with two major challenges: thrombus formation and biofouling or biofilm formation. When such a medical device is inserted into the body of a living organism, a cascade of events is initiated, including protein adsorption, platelet adhesion and activation, complement proteins binding and activation, cellular activation, and cellular attachment on the device surface. These events may initiate host response to the device including the initiation of the coagulation cascade and an inflammatory response leading the formation thrombus and cell attachment on the device surface. In addition, devices having a hydrophobic surface may provide an initial attachment site for microorganisms, which may attach and grow on the device surface and form microbial biofilms. When such microbial growth and/or thrombus formation occurs in an already immune-compromised patient, this may lead to elongated treatment times or even death.

Although hydrophilic polymer coatings have shown significant advantages as antifouling coatings, it has proven challenging to translate the techniques that have been developed on model surfaces to real world biomedical plastics. For example, many commercially available biomedical devices consist of undefined polymeric components, and it is challenging to apply one coating method to all the polymeric devices. Many of the current coating technologies do not meet all the criteria needed for the translation to medical devices, including the prevention of thrombus and biofilm formation, adaptation to multiple materials and surfaces, easy application of the coating to devices of various sizes and shapes and materials, stability of the coating, and economic feasibility.

Mussel-inspired catechol surface chemistry provide numerous strategies that have been used to develop and generate bio-inert coatings on device surfaces. Dopamine and its derivatives mimic the composition of mussel foot proteins, forming surface-adherent coatings on a wide array of materials. One strategy endowed different substrates with antifouling functions via post-modification of polydopamine (PDA) by attaching a reactive PDA layer on the surface and then reacting the functionalized hydrophilic polymers with the PDA layer via the thiol or amino groups on the hydrophilic polymers. Using this method, PDA coatings have been post-modified with functionalized polyethylene glycol, hyperbranched polyglycerol, zwitterionic polymers, and zwitterionic peptide, leading to a significant reduction of protein adsorption and cell adhesion. However, one limitation of these types of coatings is that they are very thin and lack long-term antifouling properties. Another strategy utilizes the anchoring and crosslinking properties of the catechol modality to develop antifouling coatings. In this case, polymer-catechol conjugates were utilized for the generation of an antifouling layer on a surface. Various non-fouling polymers were conjugated with catechol groups, and these conjugates were successful for developing coating surfaces (SUNDARAM, Harihara S. et al. Advanced Materials Interfaces (2014) 1: 1400071). However, the majority of these systems were only able to introduce a low density of catechol groups in the structure due to solubility issues. Such conjugates showed poor coating ability on polymeric materials due to lack of intermolecular crosslinking. Hence, it is challenging to coat hydrophilic polymers onto different surfaces with optimized thickness via a simple dipping process.

The exact mechanism of dopamine polymerization has not yet been clearly demonstrated. Some groups have suggested that PDA results from covalent bonding (HONG, Seonki et al. Advanced Functional Materials (2012) 22: 4711-4717), while others suggest a supramolecular aggregate of monomer that are held together through a combination of charge transfer, $\pi$-stacking and hydrogen bonding interactions [DREYER, Daniel R. et al. Langmuir (2012) 28:6428-6435].

Additionally, U.S. Pat. No. 8,541,060 discloses the use of a surface-modifying agent (SMA), such as dopamine and other catechols, to form a polymeric coat on a substrate, WO2011-005258 describes the combination of PDA and amine functionalized PEG and U.S. Pat. No. 8,962,772 discloses a catechol layer covalently linked to a antimicrobial cationic polycarbonate. Some groups have successfully incorporated low molecular weight polyvinyl alcohol [ZHANG, Yan et al. Langmuir (2012) 28:17585-17592], biomacomolecules including Dextran [LIU, Yunxiao et al. Langmuir (2014) 30:3118-3126] and, and heparin hyaluronic acid (HUANG, Renliang et al. Langmuir (2015) 31: 12061-12070) onto the surface during dopamine polymerization via supramolecular interaction. However, the obtained surface coatings exhibited limited antifouling performance.

SUMMARY

The present invention is based, in part, on the surprising discovery that the combination of a polymeric binder as described herein with a high molecular weight hydrophilic polymer as described herein produced a composition useful for coating a substrate. Furthermore, those substrates, when coated showed further useful properties. In some embodiments, the combination of a polymeric binder as described herein with a high molecular weight hydrophilic polymer as described herein exhibited useful properties that make them especially useful for coating substrates, whereby they allow for a single step application to a substrate. In other embodiments, the combination of a polymeric binder as described herein with a high molecular weight hydrophilic polymer as described herein provided a substrate coating that became smoother as the molecular weight of the hydrophilic polymer increased. Similarly, it was surprisingly discovered that when a composition comprising a polymeric binder as described herein was combined with a hydrophilic polymer as described herein, the substrate coatings produced in some embodiments coated a substrate more uniformly as the molecular weight of the hydrophilic polymer increased. In addition, in the compositions tested it was surprisingly discovered that as the molecular weight of the hydrophilic polymer increased the antifouling properties also improved. Similarly, in some of the compositions tested it was surprisingly discovered that as the molecular weight of the hydrophilic polymer increased the antithrombotic properties also improved. In some of the compositions tested, it was surprisingly discovered that as the molecular weight of the hydrophilic polymer increased the uniformity of the coating on the substrate improved.

In accordance with one embodiment, there is provided a composition, the composition, the composition comprising: (a) a polymeric binder, wherein a monomer of the polymeric binder may have the following structure:

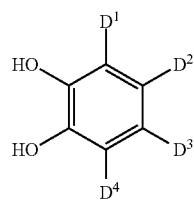

wherein, $D^1$ may be selected from H, OH,

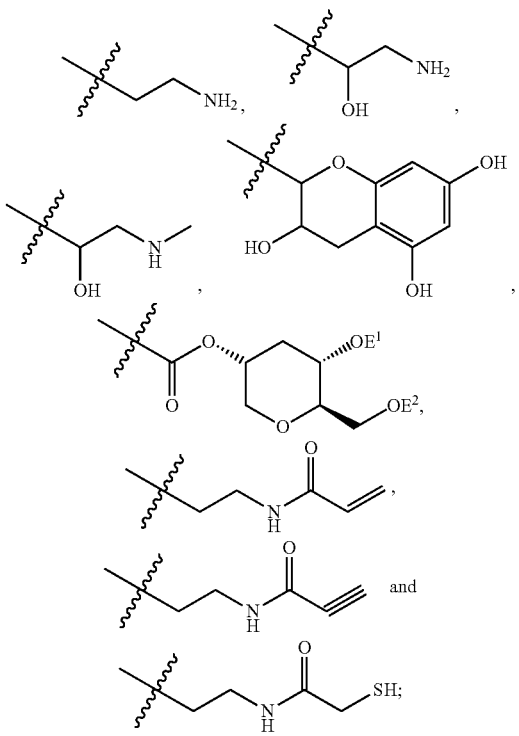

$D^2$ may be selected from H, OH,

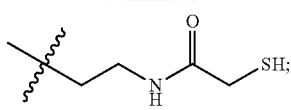

$D^3$ may be selected from H, OH,

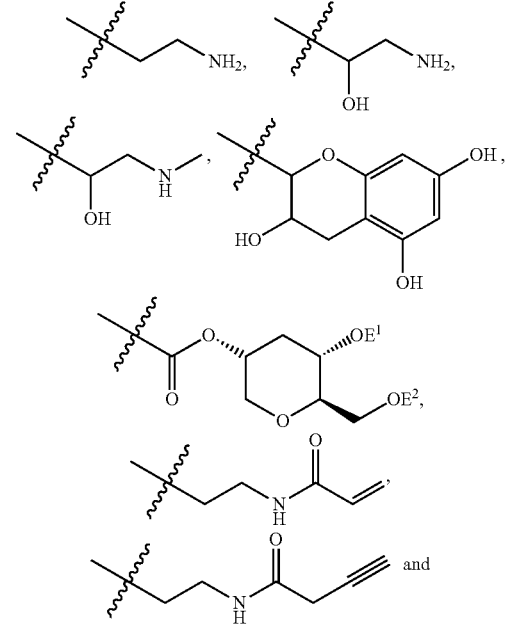

-continued

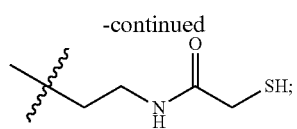

$D^4$ may be selected from H, OH,

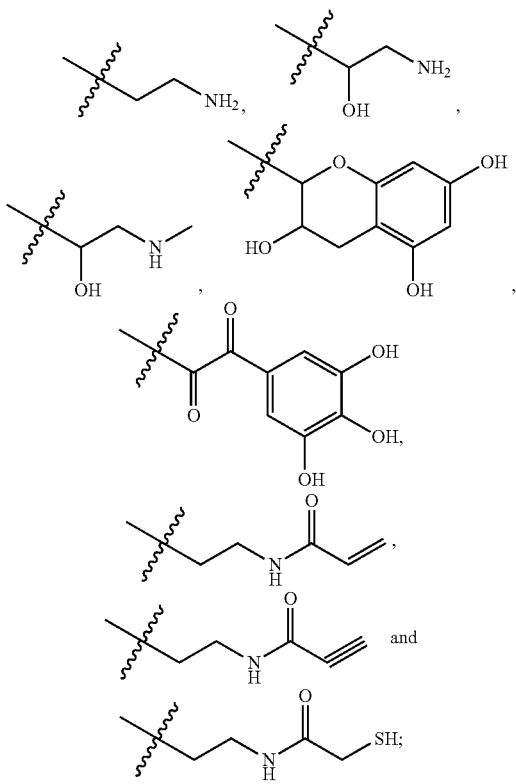

wherein $E^1$ may be H or

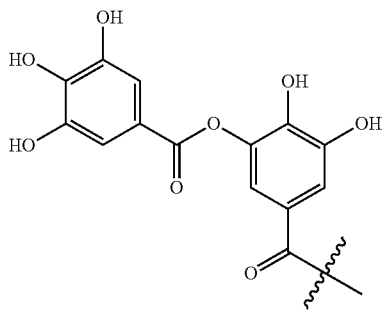 [SMILES: *C(=O)c1cc(O)c(O)c(OC(=O)c2cc(O)c(O)c(O)c2)c1]

wherein $E^2$ may be H or

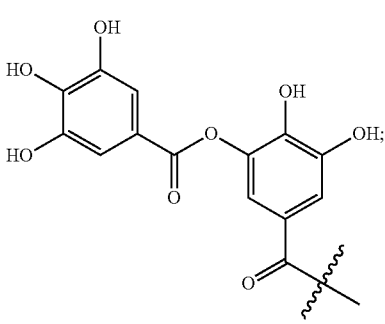 [SMILES: *C(=O)c1cc(O)c(O)c(OC(=O)c2cc(O)c(O)c(O)c2)c1]

and (b) a hydrophilic polymer, wherein the hydrophilic polymer is comprised of monomer units having the following structure:

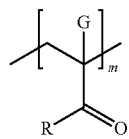

II wherein, G may be H or $CH_3$; R may be selected from

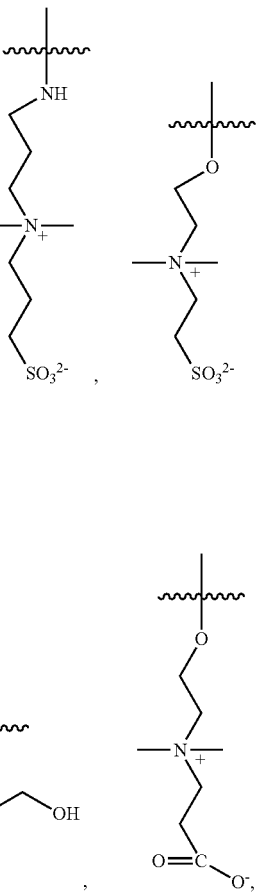

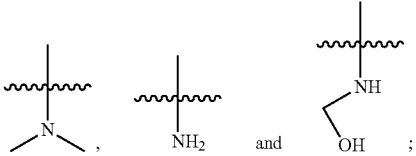

and m may be an integer between 400 and 5,000,000.

In accordance with another embodiment, there is provided a coated substrate, the coated substrate comprising: (a) a substrate; (b) a polymeric binder bound to the substrate, wherein a monomer of the polymeric binder may have the following structure:

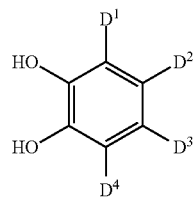
wherein, $D^1$ may be selected from H, OH,
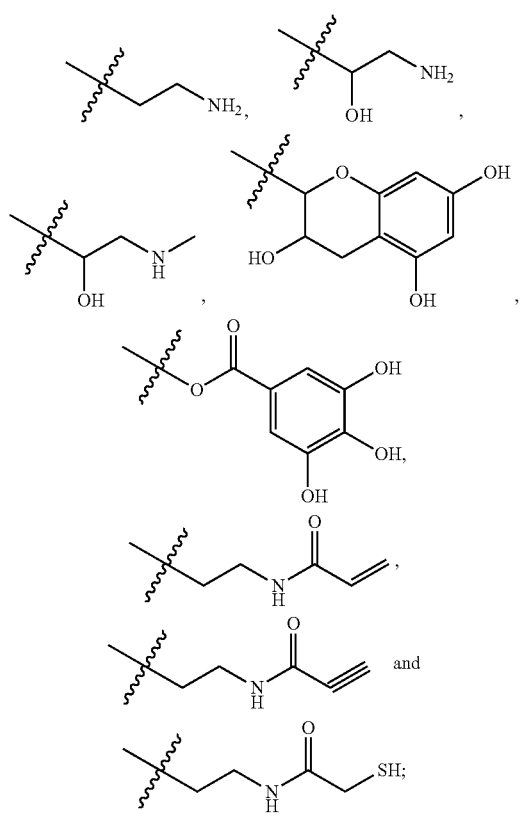
$D^2$ may be selected from H, OH,
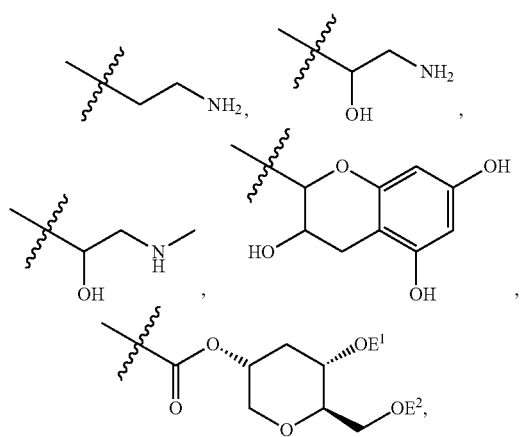
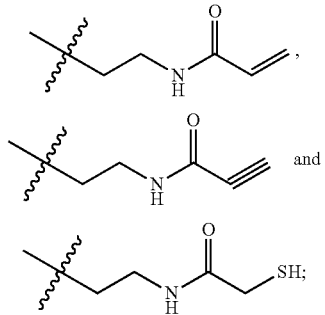
$D^3$ may be selected from H, OH,
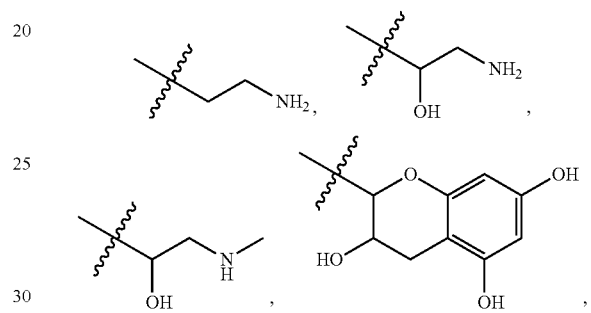
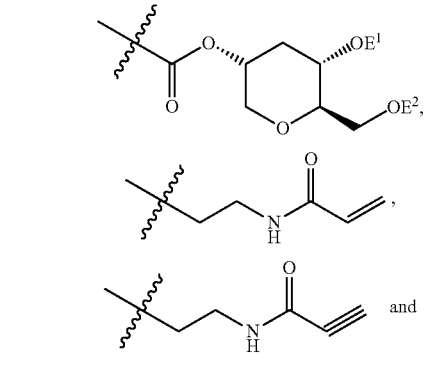
$D^4$ may be selected from H, OH,
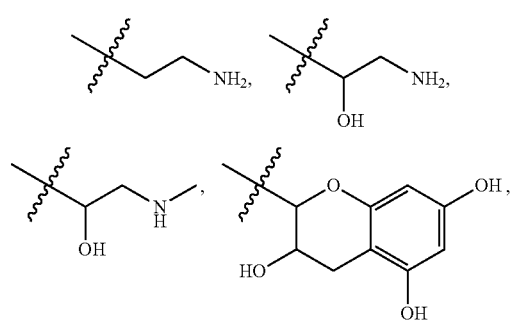

-continued

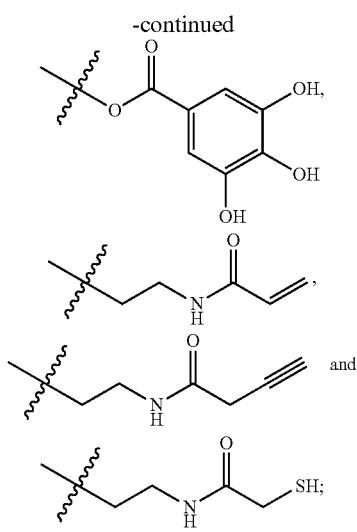

wherein $E^1$ may be H or

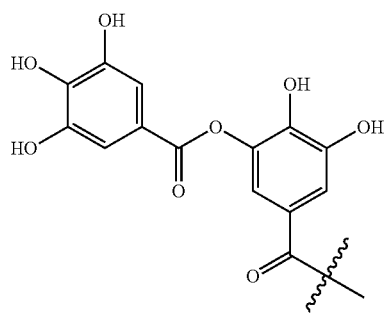 [SMILES: *C(=O)c1cc(O)c(O)c(OC(=O)c2cc(O)c(O)c(O)c2)c1]

wherein $E^2$ may be H or

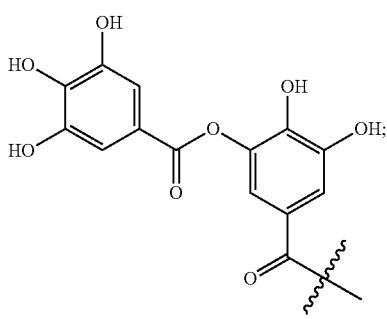 [SMILES: *C(=O)c1cc(O)c(O)c(OC(=O)c2cc(O)c(O)c(O)c2)c1]

and (c) a hydrophilic polymer bound to the polymeric binder, wherein the hydrophilic polymer may be comprised of monomer units having the following structure:

II
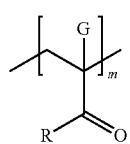

wherein, G may be H or $CH_3$; R may be selected from

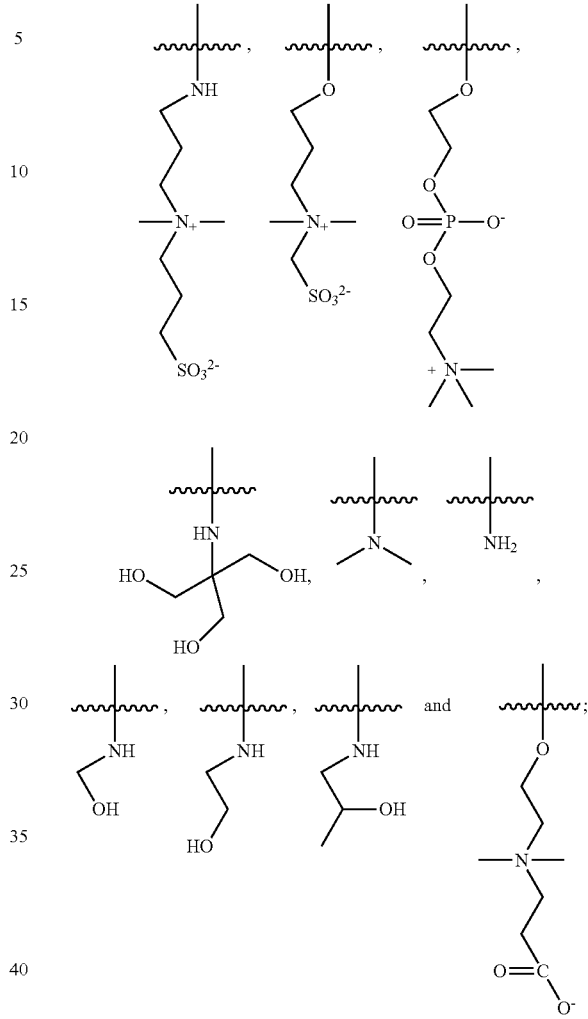

and m may be an integer between 400 and 5,000,000.

In accordance with another embodiment, there is provided a method of coating a substrate, wherein the substrate is immersed in a solution comprising the composition described herein.

In accordance with another embodiment, there is provided a method of coating a substrate, wherein the substrate is sprayed with a solution comprising the composition described herein.

In accordance with another embodiment, there is provided a use of a composition described herein for coating a substrate.

In accordance with another embodiment, there is provided a coated substrate described herein for preventing biofouling of the substrate.

In accordance with another embodiment, there is provided a coated a substrate as described herein for use in preventing adhesion to the substrate.

In accordance with another embodiment, there is provided a coated a substrate as described herein for use in preventing thrombus formation.

$D^1$ may be selected from H, OH,
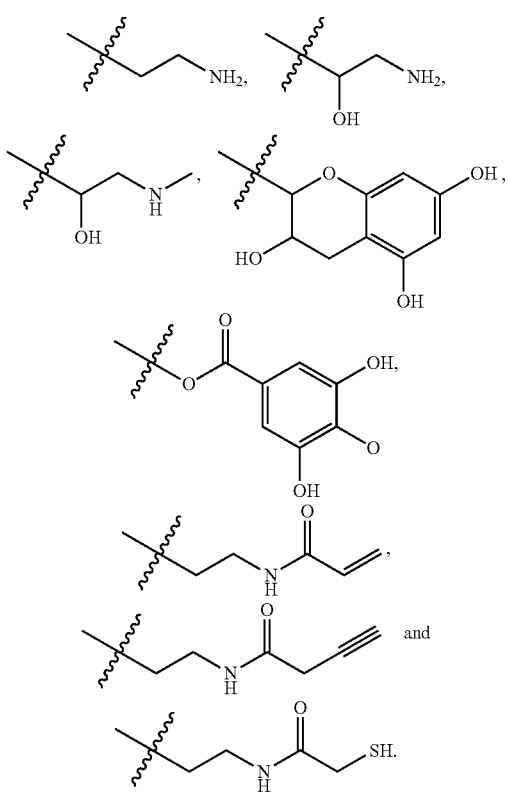
$D^1$ may be selected from H, OH,
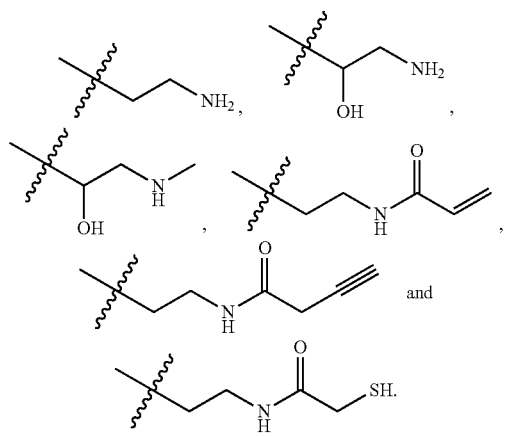
$D^1$ may be selected from H, OH,
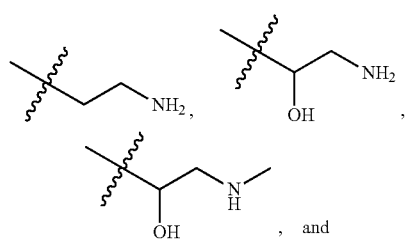
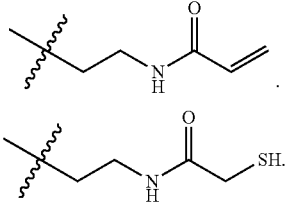
$D^1$ may be selected from H, OH,
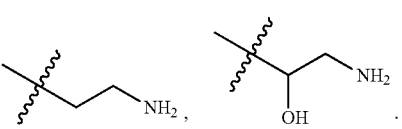
$D^1$ may be selected from H and OH.
$D^2$ may be selected from H, OH,
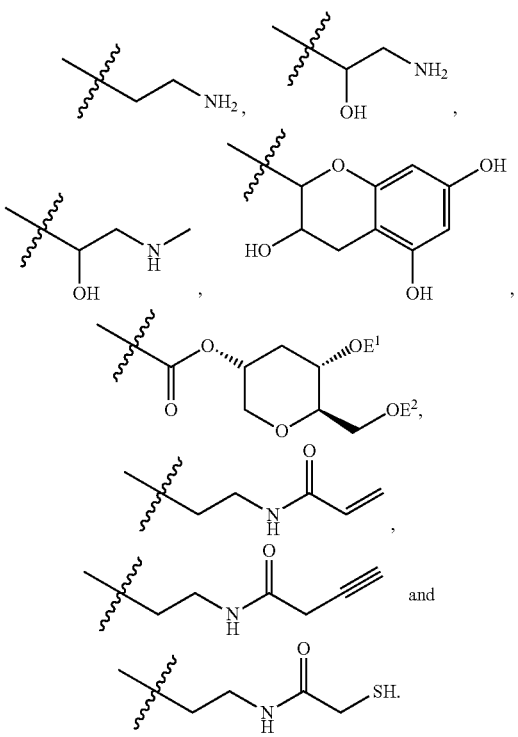
$D^2$ may be selected from H, OH,
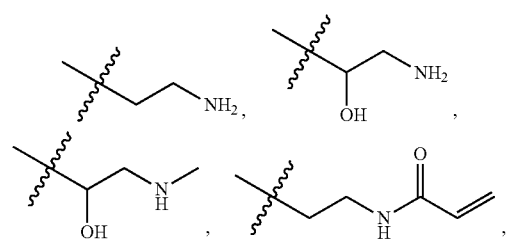

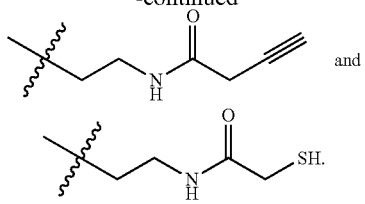 and
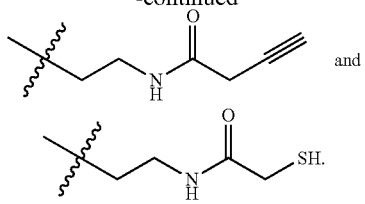 SH.
$D^2$ may be selected from H, OH,
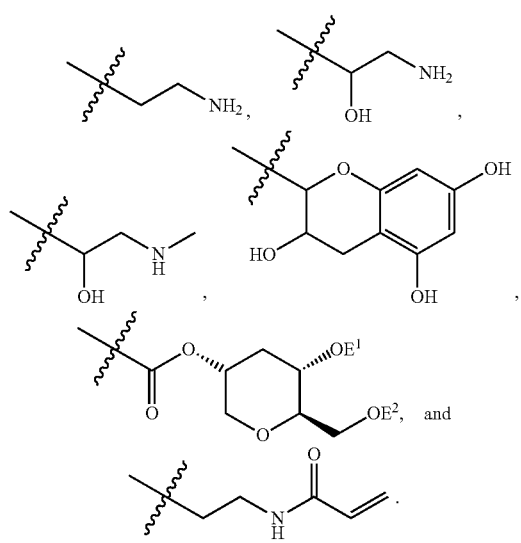
$D^2$ may be selected from H, OH,
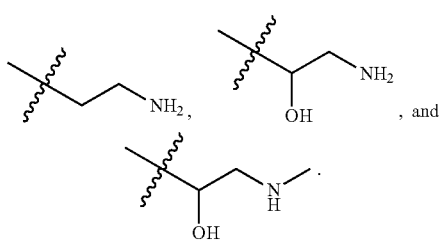
$D^2$ may be selected from H, OH,
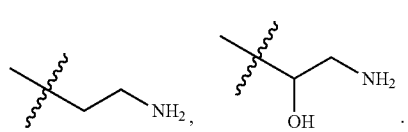
$D^2$ may be selected from H, OH,
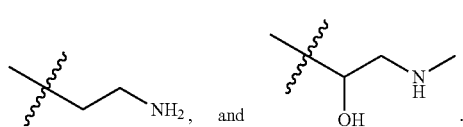.
$D^2$ may be selected from H,
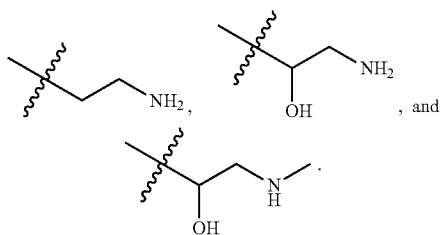
$D^2$ may be selected from OH,
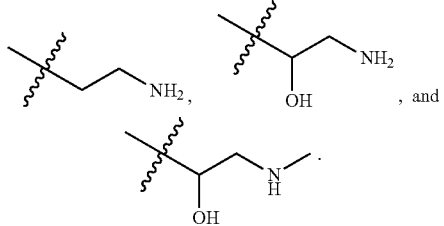
$D^2$ may be selected from
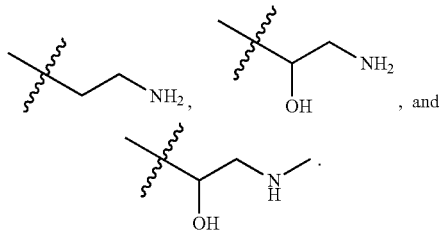
$D^2$ may be selected from H, OH, and
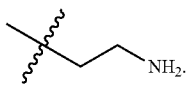.
$D^3$ may be selected from H, OH,
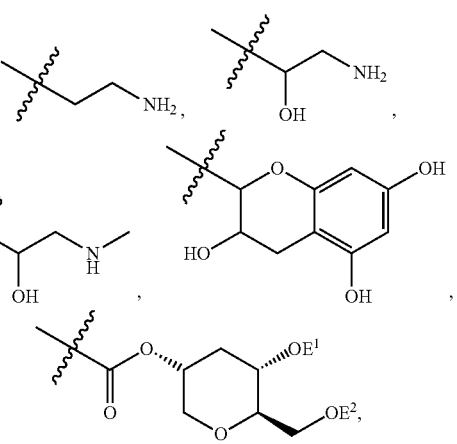

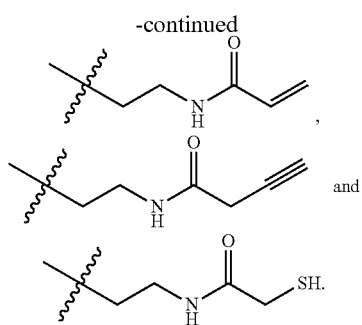
$D^3$ may be selected from H, OH,
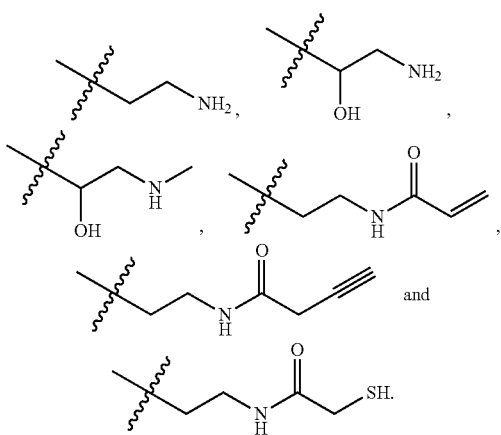
$D^3$ may be selected from H, OH,
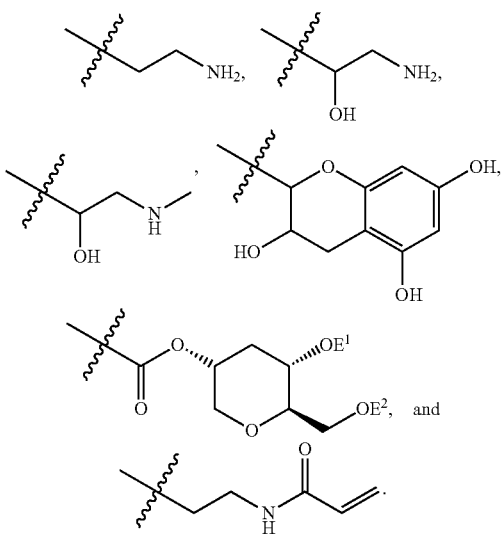
$D^3$ may be selected from H, OH,
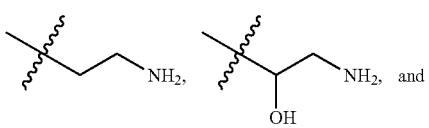
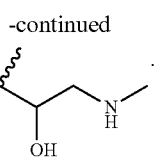
$D^3$ may be selected from H, OH,
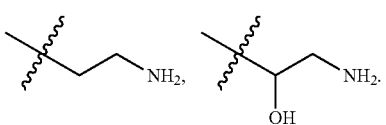
$D^3$ may be selected from H, OH,
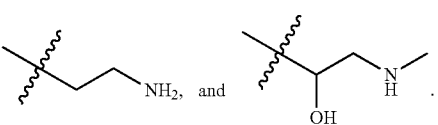
$D^3$ may be selected from H,
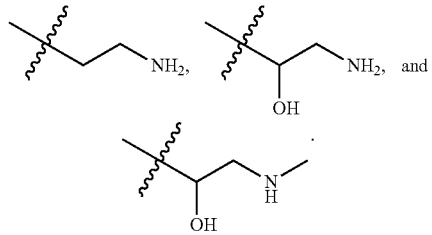
$D^3$ may be selected from OH,
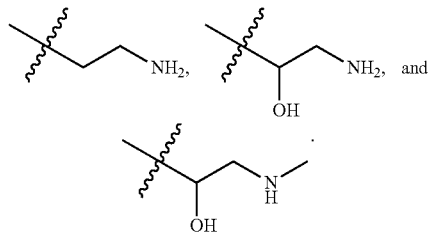
$D^3$ may be selected from
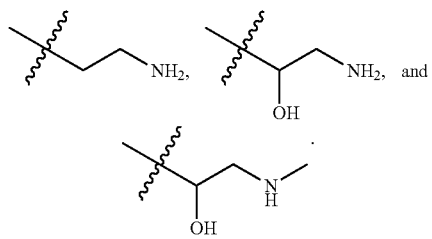

$D^3$ may be selected from H, OH, and
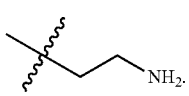
$D^4$ may be selected from H, OH,
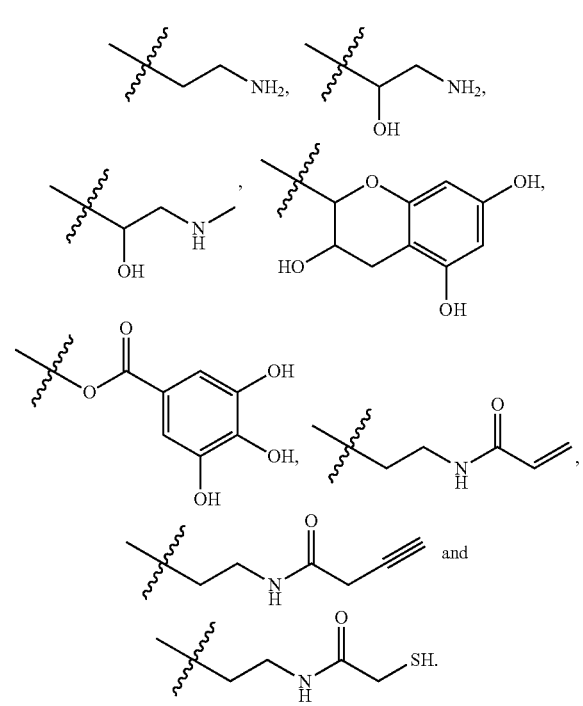
,
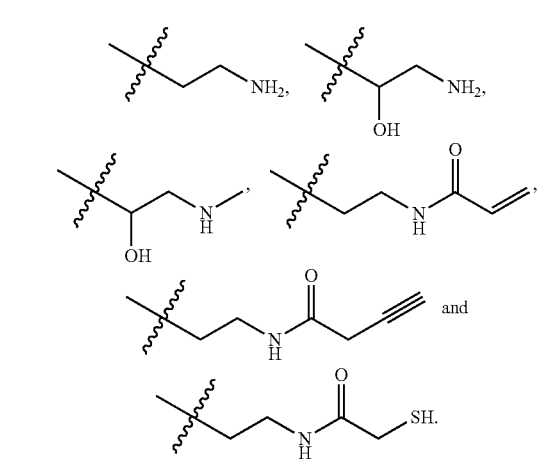
$D^4$ may be selected from H, OH,
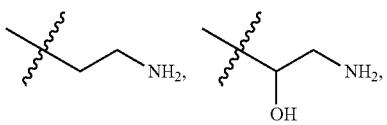
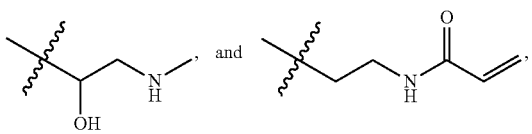
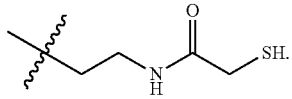
$D^4$ may be selected from H, OH,
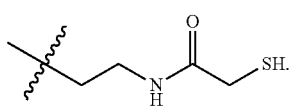
$D^4$ may be selected from H and OH.
$E^1$ may be H or
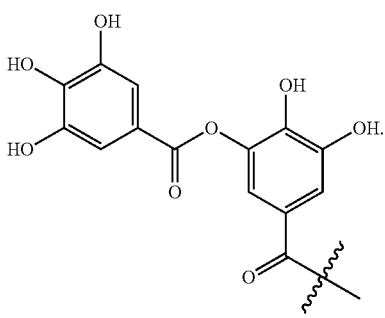 [SMILES: *C(=O)c1cc(O)c(O)c(OC(=O)c2cc(O)c(O)c(O)c2)c1]
$E^1$ may be H. $E^1$ may be
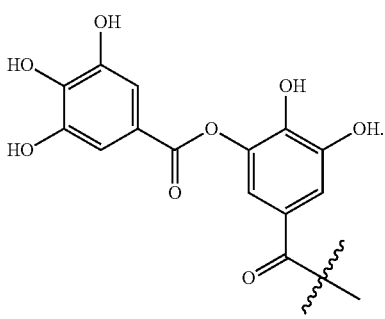 [SMILES: *C(=O)c1cc(O)c(O)c(OC(=O)c2cc(O)c(O)c(O)c2)c1]

$E^2$ may be H or
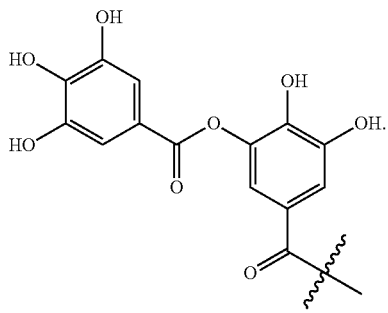 [SMILES: *C(=O)c1cc(O)c(O)c(OC(=O)c2cc(O)c(O)c(O)c2)c1]
$E^2$ may be H. $E^2$ may be
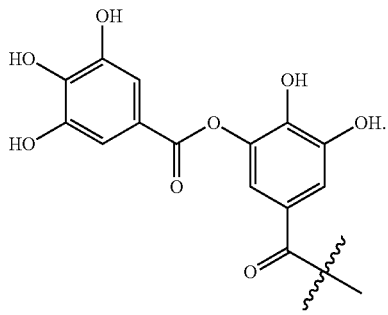 [SMILES: *C(=O)c1cc(O)c(O)c(OC(=O)c2cc(O)c(O)c(O)c2)c1]
G may be H or $CH_3$. G may be $CH_3$. R may be selected from
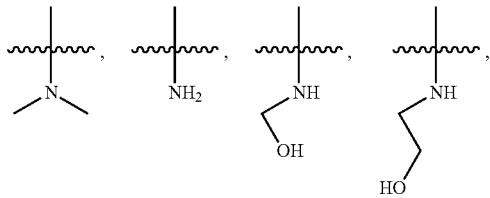
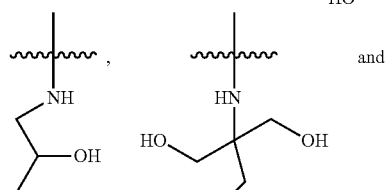
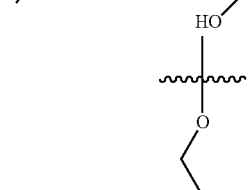
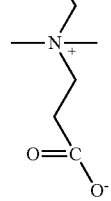
R may be selected from
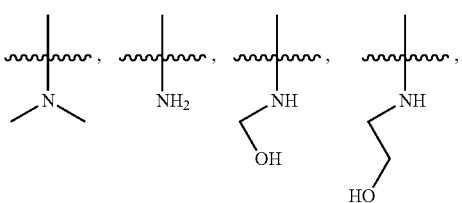
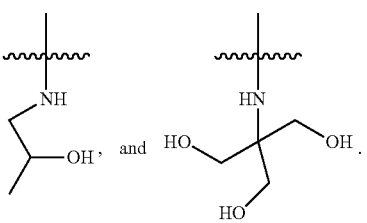
R may be selected from
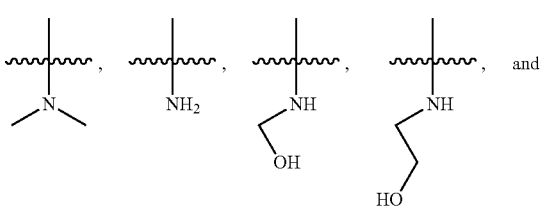
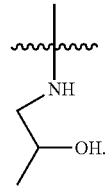
R may be selected from
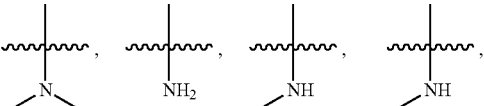
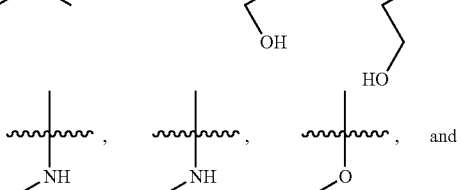
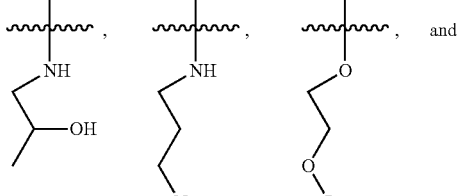
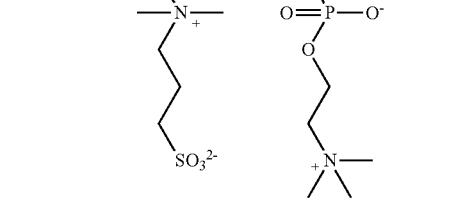

-continued

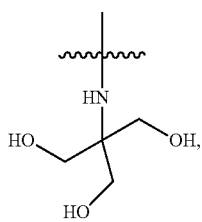

R may be selected from

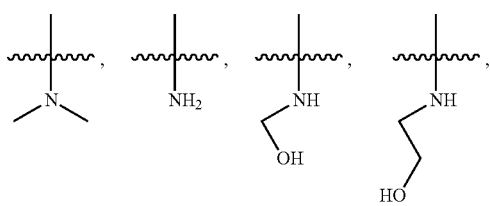

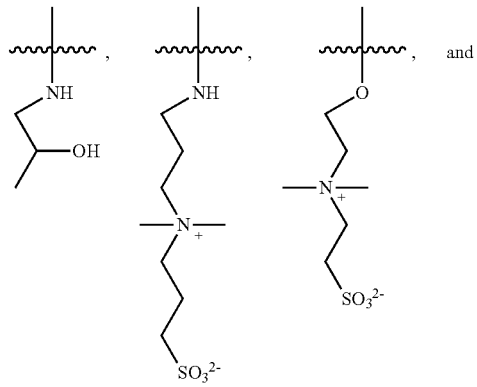

R may be selected from

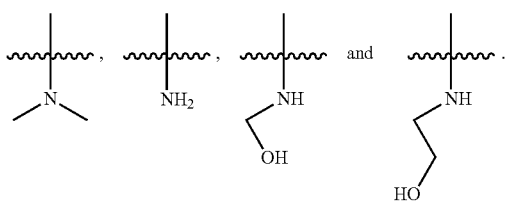

R may be selected from

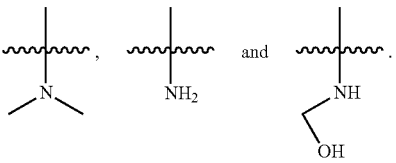

R may be

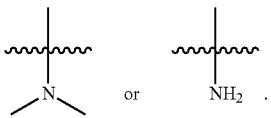

R may be

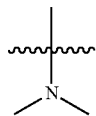

m may be an integer between 400 and 5,000,000. m may be an integer between 200 and 5,000,000. m may be an integer between 300 and 5,000,000. m may be an integer between 400 and 6,000,000. m may be an integer between 400 and 7,000,000. m may be an integer between 400 and 10,000,000. m may be an integer between 400 and 12,000,000. m may be an integer between 400 and 2,000,000. m may be an integer between 400 and 3,000,000. m may be an integer between 400 and 2,000,000. m may be an integer between 400 and 1,000,000. m may be an integer between 400 and 500,000.

The composition may further include a buffer. The composition may further include an aqueous solution. The aqueous solution may be without a salt. The aqueous solution may be with a salt. The composition may further include a water soluble organic solvent. The water soluble organic solvent may be selected from one or more of: alcohol, DMF, DMSO, acetonitrile and acetone. The composition may further include water. The buffer may have a pH of between 7 and 12. The buffer may have a pH of between 7 and 11. The buffer may have a pH of between 7 and 10. The buffer may have a pH of between 7 and 9. The buffer may have a pH of between 7 and 8. The buffer may have a pH of between 7.3 and 10. The buffer may have a pH of between 7.4 and 10. The buffer may have a pH of between 7.5 and 10. The buffer may have a pH of between 7.6 and 10. The buffer may have a pH of between 7.7 and 10. The buffer may have a pH of between 8 and 10. The buffer may have a pH of between 8 and 11. The buffer may have a pH of between 8 and 12. The buffer may be without a salt. The buffer may include a salt. The ratio of the polymeric binder to hydrophilic polymer may be between 100:1 and 1:100. The ratio of the polymeric binder to hydrophilic polymer may be between 1:1 and 1:30. The ratio of the polymeric binder to hydrophilic polymer may be between 1:5 and 1:15. The ratio of the polymeric binder to hydrophilic polymer may be between 1:2 and 1:10. The ratio of the polymeric binder to hydrophilic polymer may be between 1:1 and 1:10. The ratio of the polymeric binder to hydrophilic polymer may be between 1:3 and 1:10. The ratio of the polymeric binder to hydrophilic polymer may be between 1:4 and 1:10. The ratio of the polymeric binder to hydrophilic polymer may be between 1:1 and 1:15. The ratio of the polymeric binder to hydrophilic polymer may be between 1:2 and 1:15. The ratio of the polymeric binder to hydrophilic polymer may be between 1:3 and 1:15. The ratio of the polymeric binder to hydrophilic polymer may be between 1:4 and 1:15. The ratio of the polymeric binder to hydrophilic polymer may be between 1:5 and 1:12.

The hydrophilic polymer may have a number average molecular weight ($M_n$) of at least 100 kDa. The hydrophilic polymer may have a number average molecular weight ($M_n$) of at least 150 kDa. The hydrophilic polymer may have a number average molecular weight ($M_n$) of at least 200 kDa. The hydrophilic polymer may have a number average molecular weight ($M_n$) of at least 250 kDa. The hydrophilic polymer may have a number average molecular weight ($M_n$) of at least 213 kDa. The hydrophilic polymer may have a number average molecular weight ($M_n$) of at least 300 kDa. The hydrophilic polymer may have a number average molecular weight ($M_n$) of at least 350 kDa. The hydrophilic polymer may have a number average molecular weight ($M_n$) of at least 400 kDa. The hydrophilic polymer may have a number average molecular weight ($M_n$) of at least 450 kDa. The hydrophilic polymer may have a number average molecular weight ($M_n$) of at least 500 kDa. The hydrophilic polymer may have a number average molecular weight ($M_n$) of at least 600 kDa. The hydrophilic polymer may have a number average molecular weight ($M_n$) of at least 700 kDa. The hydrophilic polymer may have a number average molecular weight ($M_n$) of at least 795 kDa. The hydrophilic polymer may have a number average molecular weight ($M_n$) of at least 800 kDa. The hydrophilic polymer may have a number average molecular weight ($M_n$) of at least 900 kDa. The hydrophilic polymer may have a number average molecular weight ($M_n$) of at least 996 kDa.

The polymeric binder may be selected from one or more of: polymeric dopamine (PDA); polymeric norepinephrine (PNE); polymeric epinephrine (PEPI); polymeric pyrogallol (PPG); polymeric tannic acid (PTA); polymeric hydroxyhydroquinone (PHHQ); polymeric catechin; and polymeric epigallocatechin. The polymeric binder may be selected from one or more of: polymeric dopamine (PDA); polymeric norepinephrine (PNE); polymeric epinephrine (PEPI); polymeric pyrogallol (PPG); and polymeric tannic acid (PTA). The polymeric binder may be selected from one or more of: polymeric dopamine (PDA); polymeric norepinephrine (PNE); polymeric epinephrine (PEPI); and polymeric pyrogallol (PPG). The polymeric binder may be selected from one or more of: polymeric dopamine (PDA); polymeric norepinephrine (PNE); polymeric pyrogallol (PPG); and polymeric tannic acid (PTA). The polymeric binder may be selected from one or more of: polymeric dopamine (PDA); polymeric epinephrine (PEPI) and polymeric norepinephrine (PNE). The polymeric binder may be polymeric dopamine (PDA).

The hydrophilic polymer may be selected from one or more of: poly(acrylamide) (PAM); poly(N,N-dimethyl acrylamide) (PDMA); poly(N-hydroxymethyl acrylamide) (PHMA); poly(N-hydroxyethyl acrylamide) (PHEA); poly{N-[tris(hydroxymethyl) methyl]acrylamide} (PTHMAM); poly(N-(2-hydroxypropyl)methacrylamide) (PHPMA); poly(N-(3-(methacryloylamino)propyl)-N,N-dimethyl-N-(3-sulfopropyl) ammonium hydroxide) (PMPDSAH); and poly(2-methacryloyloxyethyl phosphorylcholine) (PMPC). The hydrophilic polymer may be selected from one or more of: PAM; PDMA; PHMA; PHEA; and PHPMA. The hydrophilic polymer may be selected from one or more of: PAM; and PDMA. The hydrophilic polymer may be selected from one or more of: PDMA; and PHMA. The hydrophilic polymer may be selected from one or more of: PDMA; and PHEA. The hydrophilic polymer may be selected from one or more of: PDMA; and PHPMA. The hydrophilic polymer may be selected from one or more of: PAM; PDMA; and PHMA. The hydrophilic polymer may be selected from one or more of: PAM; PDMA; and PHEA. The hydrophilic polymer may be selected from one or more of: PAM; PDMA; and PHPMA. The hydrophilic polymer may be selected from one or more of: PDMA; PHMA; and PHEA. The hydrophilic polymer may be selected from one or more of: PDMA; PHMA; and PHPMA. The hydrophilic polymer may be selected from one or more of: PAM; PDMA; PHMA; and PHEA. The hydrophilic polymer may be selected from one or more of: PAM; PDMA; PHMA; and PHPMA. The hydrophilic polymer may be selected from one or more of: PAM; PDMA; PHEA; and PHPMA. The hydrophilic polymer may be selected from one or more of: PDMA; PHMA; PHEA; and PHPMA. The hydrophilic polymer may be PDMA.

The substrate may be a plastic, a metal, a ceramic, a carbon based material, a metal oxide, a hydrogels, a biological tissue, a wood or a cement. The substrate may be poly(propylene) (PP); poly(urethane) (PU); poly(ethylene) (PE); unplasticized polyvinyl chloride (uPVC); plasticized polyvinyl chloride (pPVC); poly(imide) (PI); ethylene vinyl acetate (EVA); poly(tetrafluoroethylene) (PTFE); titanium dioxide ($TiO_2$), or silicon dioxide ($SiO_2$). The substrate may be PP, PU, PE, uPVC, pPVC, PI, EVA, or PTFE. The substrate may be $TiO_2$ or $SiO_2$. The substrate may form part of an apparatus. The apparatus may be selected from: a urinary device; a dental fixture; an artificial joint; a vascular device; a storage device; a microfluidic device; a filtration membrane; a feed tube; or a diagnostic device. The vascular device may a catheter, a lead, or a stent. The urinary device may be a urine storage device, catheter, or a stent. The filtration membrane may be a blood filtration membrane, a water purification membrane, or an air purification membrane.

The method may further comprise drying the substrate. The method may further comprise applying a further coat of the solution following the drying of the substrate. The method may further comprise a second drying of the substrate. The method may further comprise one or more repetitions of the applying a further coat of the solution followed by one or more subsequent drying steps. The method may further comprise mechanical agitation following immersion in the solution. The method may further comprise the application of a primer, prior to immersion in or spraying of a solution comprising a composition described herein. The drying may be in flow of argon gas or a flow of nitrogen gas.

The composition described herein may be for use as an anti-fouling agent. The composition described herein may be for use as an anti-adhesion agent. The coated substrate described herein may be for reducing biofouling. The coated substrate described herein may be for reducing adhesion. The coated substrate described herein may be for reducing thrombus formation.

The coating may be of uniform thickness. The coating may be applied in 2 coats. The coating may be applied in 3 coats. The coating may be applied in 4 coats. The coating may be applied in 5 coats. The coating may be applied in 6 coats. The coating may be applied in 7 coats. The coating may be applied in 8 coats. The coating may be applied in 9 coats. The coating may be applied in 10 coats. The coating may be applied in 1 coat.

The methods described herein may be for preventing thrombus formation; biofouling; biofilm formation; protein adsorption; protein binding; cell adhesion; platelet adhesion; microorganism adhesion; and microorganism adhesion and growth. The microorganism may be bacteria. The bacteria may be Gram-positive or Gram-negative bacteria. The gram-positive bacteria may be *Staphyloccous aureus* (*S. aureus*). The gram-negative bacteria may be *Escherichia coli* (*E. coli*).

The coating solution may comprise a coating comprising PDA and hydrophilic polymer with a molecular weight of 300 kDa and higher. The coating solution may comprise a solution comprising PDA and hydrophilic polymer with a molecular weight of 300 kDa and higher. The coating solution may comprise a PDA and a hydrophilic polymer with a molecular weight of 300 kDa and higher.

The hydrophilic polymer may be PAM, PDMA, PHMA, PHEA, PTHMAM, PMA, PHPMA, PMPDSAH, PMPC, PVP, PEO, HPG, or Dextran. The hydrophilic polymer may be PDMA, PHPMA, PAM, or PHEA. The hydrophilic polymer may be PDMA. In a further embodiment the formed polymeric particles may be uniform. In a further embodiment the polymeric particles of the coating may be uniform.

The method of coating a surface, may include providing a solution comprising PDA and hydrophilic polymer and contacting said solution with the surface of a substrate. Wherein the method is substrate independent, and wherein the method of contacting the solution and surface of the substrate may be as a dip-coating. Wherein the substrate may be a plastic, a metal, a ceramic, a carbon based material, a metal oxide, a hydrogels, a biological tissue, a wood or a cement.

In a further embodiment the present invention provides a method of coating a surface, wherein the method comprises providing a solution comprising PDA and hydrophilic polymer of molecular weight above 300 KDa and applying said coating to a substrate.

The method may be substrate independent, and wherein the method of application may be as a dip-coating. The substrate may be plastic, metal, or metal oxide. The substrate may be one or more of PP, PU, PE, uPVC, pPVC, PI, EVA, Teflon, titanium dioxide ($TiO_2$), or silicon dioxide ($SiO_2$). The substrate may be PP, PU, PE, uPVC, pPVC, PI, EVA, or Teflon. The substrate may be $TiO_2$ or $SiO_2$.

The coating may be of high lubricity. The coating may prevent biofilm formation. The coating may be for the prevention of protein adsorption, protein binding, cell adhesion, platelet adhesion, or microorganism adhesion. The coating may prevent microorganism adhesion and growth. The substrate may be a medical implant or device.

The coating may be applied to urinary implants and devices, dental fixtures, artificial joints, vascular stents, or other type of vascular implant and devices, as well as blood filtration systems, blood storage devices, microfluidic devices and diagnostic devices. The coating described herein may also be used ex vivo.

DETAILED DESCRIPTION

Figures 1A, 1B:
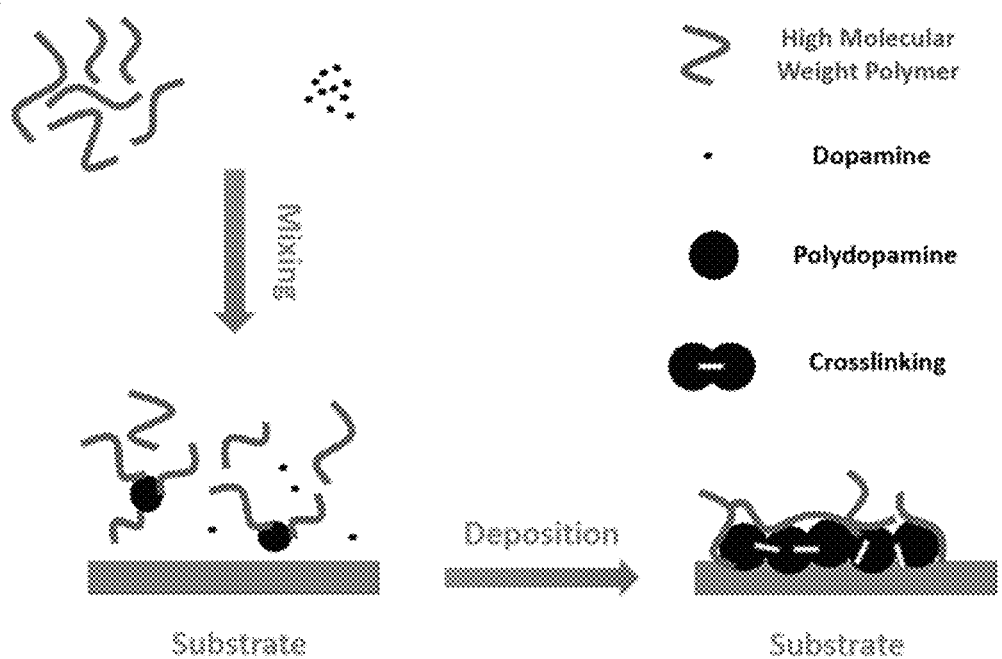
FIG. 1A shows a schematic illustration of deposition of high molecular weight hydrophilic polymers and dopamine on a substrate in an alkaline solution.
FIG. 1B shows the chemical structures of the monomer units that may up some of polymers tested herein.

The following detailed description will be better understood when read in conjunction with the appended figures. For the purpose of illustrating the invention, the figures demonstrate embodiments of the present invention. However, the invention is not limited to the precise arrangements, examples, and instrumentalities shown.

Any terms not directly defined herein shall be understood to have the meanings commonly associated with them as understood within the art of the invention.

The term "high molecular weight polymer" or HMW polymer as used herein refers to any polymer having a molecular weight ≥100,000 daltons (i.e. greater than and equal to 100 kDa) and in particular refers to the hydrophilic polymers described herein.

As used herein "uniformity" refers to the thickness of the coating formed over the entire surface of the substrate to which the coating compositions described herein were applied. The term implies that there is a consistency over the entirety of the substrate surface in terms of composition (i.e. polymeric binder and hydrophilic polymer) and the overall thickness of the coating and thus has implications for the smoothness of the coating.

The term "polymeric binder" as used herein is meant to encompass catechol and catechol derivative polymers encompassed by Structure I, wherein Structure I is represented by I
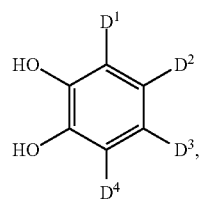
wherein, $D^1$ may be selected from H, OH,
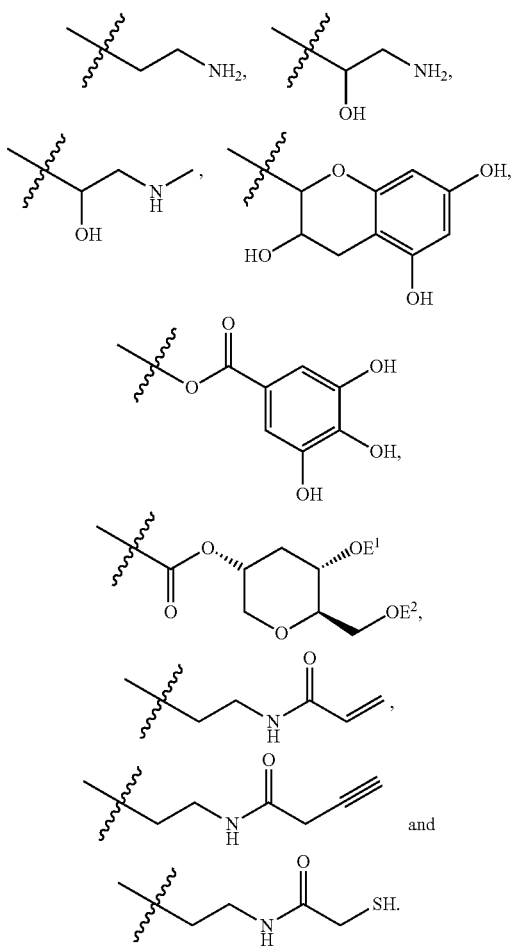
$D^2$ may be selected from H, OH,
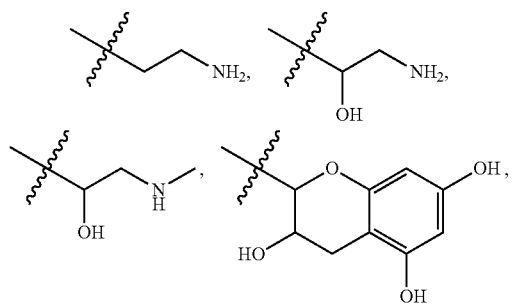
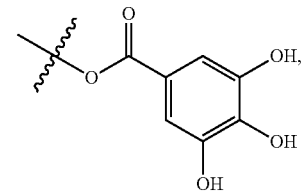
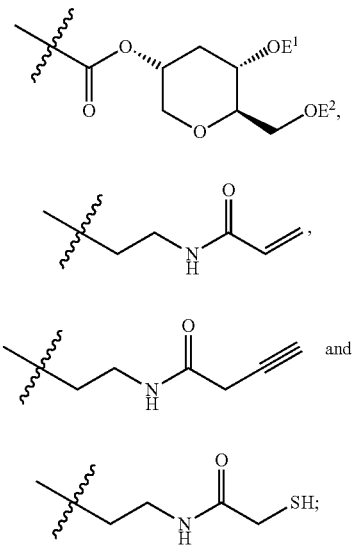
$D^3$ may be selected from H, OH,
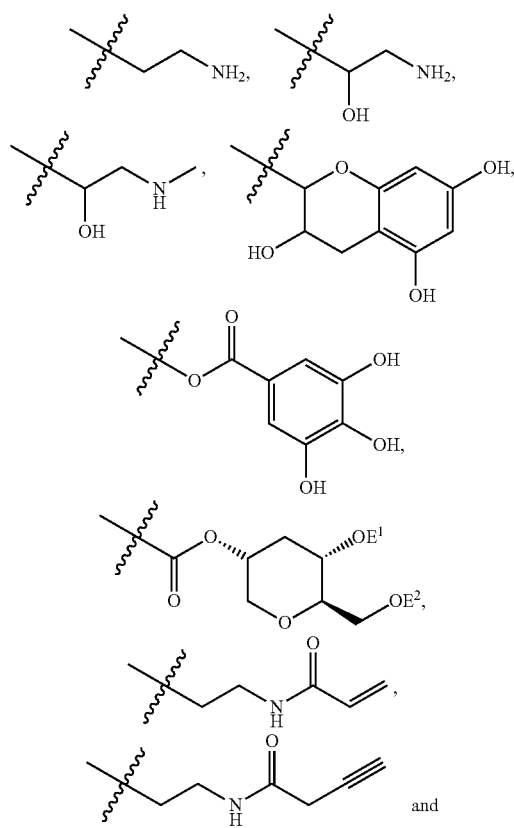

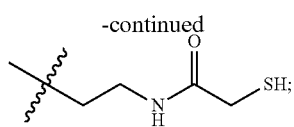

$D^4$ may be selected from H, OH,

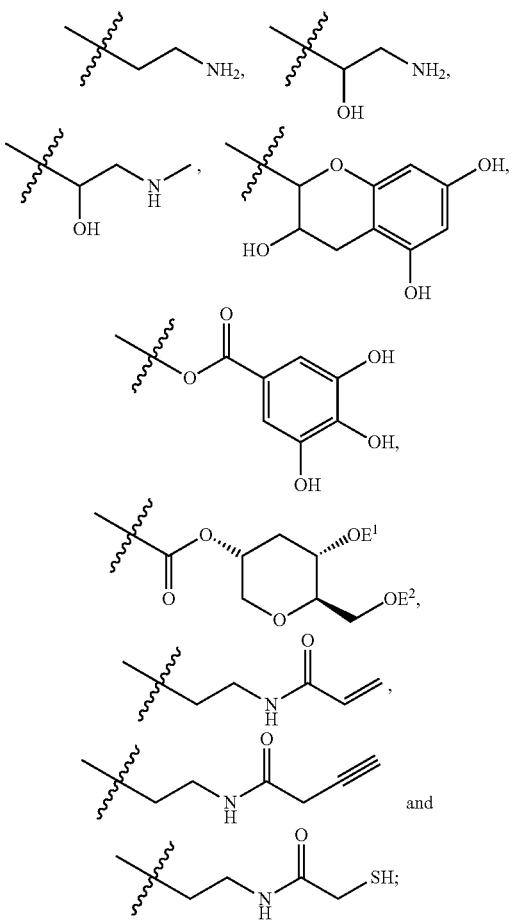

wherein $E^1$ and $E^2$ may be selected from H or

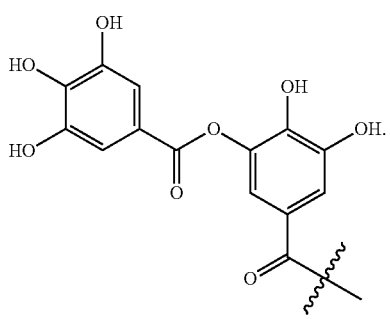 [SMILES: *C(=O)c1cc(O)c(O)c(OC(=O)c2cc(O)c(O)c(O)c2)c1]

For example, a polymeric binder may be a polymeric dopamine (PDA), a polymeric norepinephrine (PNE), a polymeric epinephrine (PEPI), a polymeric pyrogallol (PPG), a polymeric tannic acid (PTA), a polymeric hydroxyhydroquinone (PHHQ), a polymeric catechin, or a polymeric epigallocatechin.

As used herein a "hydrophilic polymer" is meant to encompass polyacrylamides, polymethacrylamides and polymethacrylates having Structure II, wherein Structure II is as follows:

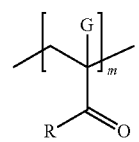

wherein, G may be H or $CH_3$. R may be selected from

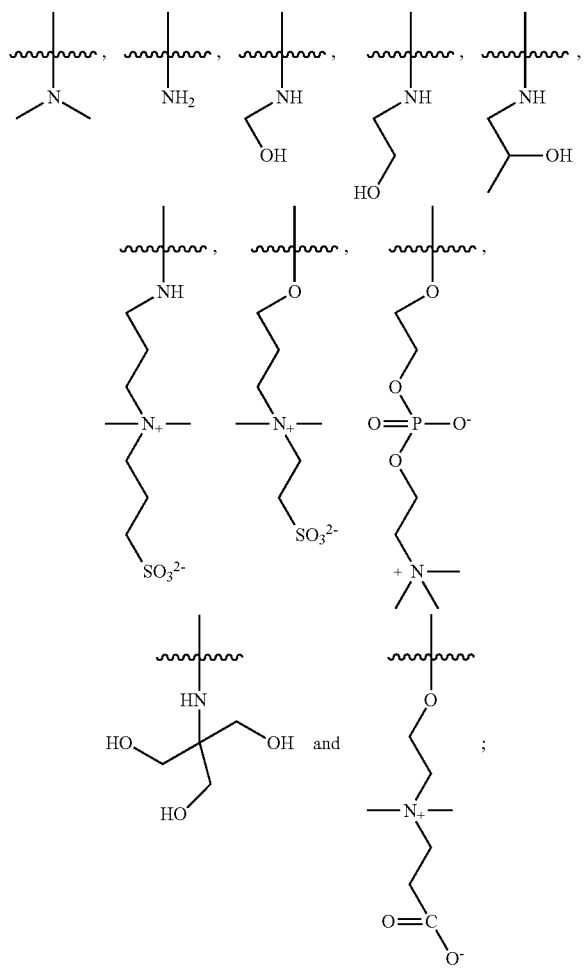

and m may be an integer between 400 and 5,000,000. Alternatively, a hydrophilic polymer may be an acrylate, an acrylamide, a methacrylate or a methacrylamide with hydroxyls, amides, substituted amides, sulfhydryl, zwitter ions in the pendent chains where degree of polymerization (m) is between 400 and 5,000,000. Alternatively, a hydrophilic polymer may be an acrylate, an acrylamide, a methacrylate or a methacrylamide wherein degree of polymerization (m) is between 400 and 5,000,000.

The term "biofilm" is used herein as it is normally understood to a person of ordinary skill in the art and often refers to any group of organisms adhering to the surface of a structure.

The term "biofouling" is used herein as it is normally understood to a person of ordinary skill in the art and often refers to the colonization of an interface by organisms, which often leads to deterioration of the interface.

The term "antifouling" is used herein as it is normally understood to a person of ordinary skill in the art and often refers to the reduction of formation of biofilms and biofouling.

The term "thrombus" is used herein as it is normally understood to a person of ordinary skill in the art and often referred to as blood clot, as the product of blood coagulation steps in hemostasis.

The term "primer" as used herein is meant to encompass any coating applied to a substrate before a subsequent composition is applied. The primer may act to prepare the surface of the substrate or facilitate the application of an subsequent composition to the substrate.

The term "plastic" as used herein is meant to encompass a vast number of synthetic or semi-synthetic organic polymers that are malleable and may be molded into solid forms. Exemplary plastics are: Polyester (PES); Polyethylene terephthalate (PET); Polyethylene (PE); High-density polyethylene (HDPE); Polyvinyl chloride (PVC); Polyvinylidene chloride (PVDC); Low-density polyethylene (LDPE); Polypropylene (PP); Polystyrene (PS); High impact polystyrene (HIPS); Polyamides (PA) (Nylons); Acrylonitrile butadiene styrene (ABS); Polyethylene/Acrylonitrile Butadiene Styrene (PE/ABS a blend of PE and ABS); Polycarbonate (PC); Polycarbonate/Acrylonitrile Butadiene Styrene (PC/ABS a blend of PC and ABS); Polyurethane (PU); Polylactic acid (PLA); Polyimide; Polyetherimide (PEI); Polyetheretherketone (PEEK); phenol formaldehydes (PF); and Polymethyl methacrylate (PMMA).

The term "polydopamine (PDA)" is used herein as it is normally understood to a person of ordinary skill in the art and often refers to the pH-dependent self-polymerization of dopamine. However, "polydopamine" may be formed by any polymerisation of dopamine monomers. It should be noted that the mechanism of PDA formation is currently not understood (Dreyer, D. R. et al., 2013; Lynge, M. E. et al., 2011). Furthermore, it should be noted that the structure of the polymer product has not been elucidated yet (Dreyer, D. R. et al., 2013).

The term "hydrophilic polymer" is used herein as it is normally understood to a person of ordinary skill in the art and often refers to a polymer containing polar or charged functional groups, rendering them soluble in water.

The term "PAM" is used herein as it is normally understood to a person of ordinary skill in the art and often refers to poly(acrylamide).

The term "PDMA" is used herein as it is normally understood to a person of ordinary skill in the art and often refers to poly(N,N-dimethyl acrylamide).

The term "PHMA" is used herein as it is normally understood to a person of ordinary skill in the art and often refers to "poly(N-hydroxymethyl acrylamide)".

The term "PHEA" is used herein as it is normally understood to a person of ordinary skill in the art and often refers to "poly(N-hydroxyethyl acrylamide)".

The term "PTHMAM" is used herein as it is normally understood to a person of ordinary skill in the art and often refers to "poly{N-[tris(hydroxymethyl) methyl]acrylamide}".

The term "PMA" is used herein as it is normally understood to a person of ordinary skill in the art and often refers to "poly(methacrylamide)".

The term "PHPMA" is used herein as it is normally understood to a person of ordinary skill in the art and often refers to "poly(N-(2-hydroxypropyl)methacrylamide)".

The term "PMPDSAH" is used herein as it is normally understood to a person of ordinary skill in the art and often refers to "poly(N-(3-(methacryloylamino)propyl)-N,N-dimethyl-N-(3-sulfopropyl) ammonium hydroxide)".

The term "PMPC" is used herein as it is normally understood to a person of ordinary skill in the art and often refers to "poly(2-methacryloyloxyethyl phosphorylcholine)".

The term "PVP" is used herein as it is normally understood to a person of ordinary skill in the art and often refers to "poly(vinyl pyrrolidone)".

The term "PEO" is used herein as it is normally understood to a person of ordinary skill in the art and often refers to "poly(ethylene oxide)".

The term "HPG" is used herein as it is normally understood to a person of ordinary skill in the art and often refers to "hyperbranched polyglycerol".

The term "Dextran" is used herein as it is normally understood to a person of ordinary skill in the art and often refers to "branched glucan composed if chains of varying length".

The term "PP" is used herein as it is normally understood to a person of ordinary skill in the art and often refers to "poly(propylene)".

The term "PU" is used herein as it is normally understood to a person of ordinary skill in the art and often refers to "poly(urethane)".

The term "PE" is used herein as it is normally understood to a person of ordinary skill in the art and often refers to "poly(ethylene)".

The term "uPVC" is used herein as it is normally understood to a person of ordinary skill in the art and often refers to "unplasticized polyvinyl chloride".

The term "pPVC" is used herein as it is normally understood to a person of ordinary skill in the art and often refers to "plasticized polyvinyl chloride".

The term "PI" is used herein as it is normally understood to a person of ordinary skill in the art and often refers to "poly(imide)".

The term "EVA" is used herein as it is normally understood to a person of ordinary skill in the art and often refers to "ethylene vinyl acetate".

The term "Teflon" is used herein as it is normally understood to a person of ordinary skill in the art and often refers to "poly(tetrafluoroethylene) or PTFE".

The term "coating" is used herein as it is normally understood to a person of ordinary skill in the art to be a covering that is applied to the surface of an object and is to be broadly constructed to include adhesive coating, resistive coating (e.g., resistive to cellular adhesion), and protective coating. The present invention offers adhesion in "highly humid" environments (50% to 80% humidity) and "wet", "saturated", or "super-saturated" environments (at least 8% humidity and higher). Adhesion under dry environment is also contemplated herein.

The term "dip-coating" is used herein as it is normally understood to a person of ordinary skill in the art and often refers to the immersion of the substrate into the solution of the coating material.

The term "lubricity" is used herein as it is normally understood to a person of ordinary skill in the art and often refers to the property of "slipperiness" or "smoothness", or "a surface with low friction".

The coating described herein has high lubricity. These coatings are useful for medical devices where their lubrication results in reduced frictional forces when the device is introduced and moved within the body, reducing inflammation and tissue trauma as well as supporting patient comfort.

Various alternative embodiments and examples are described herein. These embodiments and examples are illustrative and should not be construed as limiting the scope of the invention.

Materials and Methods

Polymer synthesis and characterization: The high molecular weight polymers were synthesized by aqueous ATRP. Molecular weight and polydispercity index (PDI) of polymers were determined by using GPC on a Waters 2690™ separation module fitted with a DAWN EOS™ multi-angle laser light scattering detector from Wyatt Technology Corp.™ with 18 detectors placed at different angles and a refractive index detector (Optilab DSP™ from Wyatt Technology Corp.™). An Ultrahydrogel™ linear column with a bead size of 6-13 μm (elution range $10^3$ to $5 \times 10^6$ Da) and an Ultrahydrogel 120™ with a bead size of 6 μm (elution range 150 to $5 \times 10^3$ Da) from Waters™ were used. The dn/de value of high molecular weight polymers in the mobile phase was determined at λ=620 nm and was used for determining molecular weight parameters. The number-average mean square radius moments were taken as the radius of gyration of the polymer.

Surface modification: The silicon wafer and titanium dioxide were exposed to oxygen plasma for 4 min to remove adventitious contamination. Other polymer substrates were cleaned by sonication in deionized water for 10 min and blow-dried under a stream of nitrogen gas. For surface modification, a mixture of 2 mg/ml dopamine and 10 mg/ml polymer was prepared in 10 mM Tris buffer (pH=8.5). The substrates were then immersed in dopamine or polymer/dopamine solution and kept for 24 h without stirring. Afterwards, the modified samples were rinsed with deionized water and dried in a steam of nitrogen gas.

Characterization of particle formation: Dynamic light scattering (DLS) measurements of the polymer solution (0.16 mg/ml in ultra-pure water) were performed using a Zetasizer NanoZS™ instrument (Malvern Instruments™) at the end the reaction. Each measurement was repeated for 3 times, and the averaged value was accepted as the final hydrodynamic size (Dh). The measurements were performed with an equilibration time of 1 min at room temperature. The nanoparticles in polymer solution were also viewed on a H7600 PC-TEM™ (Hitachi™) at an accelerating voltage of 80 KV, and images were recorded with an Advantage HR digital CCD camera (Advanced Microscopy Techniques™). UV-Vis spectra were recorded at room temperature in a Varian Cary 4000™ spectrophotometer using a 1 cm path length quartz cell.

Surface characterization: Attenuated Total Reflectance Fourier Transform Infrared (ATR-FTIR) spectra were recorded using a Thermo-Nicolet Nexus FTIR™ spectrometer (Nicolet Instrument™, Waltham, Mass.) with a MCT/A liquid nitrogen cooled detector, KBr beam splitter and MKII Golden Gate Single Refection ATR™ accessory (Specac Inc.™ Woodstock, Ga.). Spectra were recorded at 4 cm$^{-1}$ resolution and 64 scans were collected for each sample. PP films were used as the background to obtain the subtracted spectra. For static water contact angle measurements, digital images of a 5 μL water droplet on the surface were taken using a Retiga 1300™ digital camera (Q-imaging Co.™), and analyzed using Northern Eclipse™ software. Six different spots on the PP film were tested for each sample and the average value is reported. The variable-angle spectroscopic ellipsometry (VASE) spectra were collected on an M-2000 V™ spectroscopic ellipsometer (J. A. Woollam™, Lincoln, Nebr.) at 55, 65, and 75° at wavelengths from 480 to 700 nm with an M-2000 50 W quartz tungsten halogen light source. The VASE spectra were then fitted with a multilayer model utilizing WVASE32 analysis software based on the optical properties of a generalized Cauchy layer to obtain the dry thickness of the deposited layers. X-ray photoelectron spectroscopy (XPS) was performed using a Leybold LH Max 200™ surface analysis system (Leybold™, Cologne, Germany) equipped with a Mg Kα source at a power of 200 W. Elements were identified from survey spectra. High-resolution spectra were collected at 48 eV pass energy. Atomic force microscopy (AFM) measurements were performed on a commercially available multimode system with an atomic head of 130×130 μm$^2$ scan range which used a NanoScope IIIa™ controller (Digital Instruments™, Santa Barbara, Calif.). Surface morphology was examined under PBS buffer in contact mode using a commercially manufactured V-shaped silicon nitride ($Si_3N_4$) cantilever with gold on the back for laser beam reflection (Veeco™, NP-S20™). The spring constant of the AFM cantilever was measured using the thermal equipartition theorem. Force measurements were performed in PBS buffer. On tip approach the onset of the region of constant compliance was used to determine the zero distance, and on retraction the region in which force was unchanged was used to determine the zero force. The rate of tip-sample approach or retraction was typically 1 μm/s. The raw AFM force data were converted into force vs. separation using custom Matlab™ v.5.3 software. The software converts the cantilever deflection vs. linear voltage displacement transformer signal into restoring force vs. tip-substrate separation using user input trigger and spring constant values. We followed our published protocol for the calculation of the adhesive force.

Protein adsorption: To determine the extent of absorbed protein on the PP film, the samples were incubated with BSA-FITC conjugate or Fib-Alex-fluor 594™ conjugate buffer. 1 mg/ml BSA conjugate and 0.25 mg/mL Fib conjugate was prepared in PBS buffer. Before incubation with protein solutions, the samples were equilibrated with PBS for 10 min. Afterwards, the substrates were incubated with 0.3 mL stock solutions for 2 h, thoroughly washed with PBS buffer for 3 times and dried in a steam of nitrogen. The images of protein-absorbed samples were taken using a fluorescence microscope.

Blood collection: Blood was provided from donors at the Centre for Blood Research by an approved protocol by The University of British Columbia™ clinical ethics committee. Blood was collected in in serum tubes. Buffy coat Platelet-rich plasma (PRP) was obtained from Canadian Blood Services™. Serum was prepared by centrifuging whole blood containing serum tube at 1200*g for 30 min.

Complement activation: Two sets of samples each equilibrated with PBS were used for this assay. Both sets of samples were incubated with fresh human serum for 2 h at 37° C. and washed with PBS to remove any loosely adhered proteins. The first set of samples was incubated with FITC labeled anti-C3b antibody for 2 h and washed with PBS. The second set of samples was incubated with FITC Mouse IgG1 isotype control for 2 h and washed with PBS. All the dried samples were viewed under a fluorescent microscope. The samples without serum incubation were also examined as controls.

Platelet adhesion: The level of platelet adhesion on different coatings was quantified by SEM analysis. All samples were incubated in buffy coat PRP in a 24-well plate under static condition at 37° C. After 4 h, the samples were taken out and carefully washed with PBS and fixed with 2.5% glutaraldehyde for 2 h at 4° C. After serial dehydration with 50%, 60%, 70%, 80%, 90%, and 100% ethanol for 10 min each, the samples were dried, coated with a thin layer of Au, and observed under SEM. The number of platelet on the samples was quantified by counting the total number adhered platelet from at least 6 representative images at the sample magnification (×1000). The results obtained from the coated samples were normalized using the adhered number from original PP films.

Initial bacterial adhesion: For initial bacterial adhesion assay, different sterilized coatings were grown on a 96-well PP plate. Overnight culture of bacteria (S. aureus) was first adjusted to $10^6$ CFU/ml in LB. Each well was equilibrated with LB for 10 min and then coved with 0.2 ml bacterial suspension. The inoculated plate was incubated for 4 h at 37° C. After the bacterial adhesion process, the wells were filled with PBS and washed 3 times to remove non-adherent bacteria. The wells with adhered bacteria were ultrasonicated for 10 min to release bacteria cells into PBS (0.2 ml). The bacterial suspension was serially diluted and spread on an agar plate. After culturing overnight, the number of viable bacterial cells was quantified by counting the number of colonies on the agar plate.

Biofilm formation: S. aureus and E. coli biofilm were tested on unmodified and modified PP samples. The sterilized samples were cut into pieces and transferred into a 48-well plate. Overnight culture of bacteria was first adjusted to $10^6$ CFU/ml in LB. Each sample was equilibrated with LB for 10 min and then immersed in 0.6 ml S. aureus culture. The 48-well plate was incubated at 37° C. with shaking at 50 rpm. After 24 h incubation, suspension was removed and the samples were thoroughly washed with PBS to remove loosely adhered bacteria. For the assessment of adhered bacteria on samples, SYTO9™, a green-fluorescent nucleic acid staining agent, was used to label all the bacterial cells by penetrating cell membranes. The washed samples were soaked in a dye solution at room temperature in the dark for 15 min. The stained bacterial cells were viewed under a fluorescent microscope. For SEM analysis, the samples were taken out and fixed with 2.5% glutaraldehyde for 2 h at 4° C. After serial dehydration with 50%, 60%, 70%, 80%, 90%, and 100% ethanol for min each, the samples were dried, coated with a thin layer of Au, and observed under SEM. The number of bacteria on the samples was quantified by counting the total number adhered platelet from at least 6 representative images at the sample magnification (×5000). The results obtained from the coated samples were normalized using the adhered number from original PP films.

Stability of the coating: The stability of the coatings in physiological solution was monitored by thickness change. The samples were incubated in PBS buffer for different periods (3 days-3 weeks) before measuring the thickness change on silicon wafers.

Catheter evaluation: PU catheters were cut into 1-cm segments and coated with the optimized PDMA coating. All samples were sterilized with 70% ethanol. Unmodified and modified samples were rinsed with PBS to get rid of excess ethanol. Overnight cultures were diluted in LB to a concentration of approximately $1 \times 10^6$ CFU/ml, and 1 ml was added to 1.5 ml Eppendorf™ tubes. Cultures were incubated at 37° C. with shaking at 50 rpm for 6 hours. After incubation, samples were rinsed with PBS for 3 times to remove nonadherent organisms, and added to 1 ml PBS. The samples were ultrasonicated for 10 min in water bath and followed by vortexing for 10 s. Dilutions in sterile PBS were grown on agar plates to determine CFU/catheter.

In vivo Mouse Model: Prior to the animal procedure, a 24 G angio-catheter (B&D™, Mississauga, Ontario, Canada) was modified under strict aseptic conditions to "load" the catheter piece to be inserted into the bladder onto the needle. Animals underwent inhalational anesthesia with 3% isofluorane and were positioned on their back on a heating pad. All limbs were secured using tape, the abdomen was shaved and prepped with chlorhexidine and sterile ultrasound gel was applied. The bladder was visualized using a Vevo 770™ high frequency ultrasound system (VisualSonics™, Toronto, ON, Canada) and the needle-mounted modified 24 G angio-catheter was positioned at a 30° angle just above the pubic bone with the bevel directed anteriorly. After ultrasonic visualization of the needle, it was inserted towards the bladder. Once the isolated 4 mm segment was visualized inside the bladder, the needle was removed leaving only the short FEP segment in the lumen. The entire process was visualized in real-time under ultrasonic guidance. All animals received 2 mg/kg meloxicam (Metacam™, Boehringer Ingelheim™, Burlington, ON, Canada) subcutaneously before they were recovered from anesthesia.

One day following catheter implantation, animals were anesthetized again and $5 \times 10^5$ CFU/mL S. aureus in 50 µl of PBS was percutaneously injected into the bladder utilizing a 30 G needle under ultrasound guidance. Negative controls were injected with PBS only using the same procedure. Animals were recovered from anesthesia after a dwell time of 30 min. The amount of the bacterial inoculum was confirmed by serial dilutions and CFU counts on Luria Bertani (LB) agar incubated overnight at 37° C. Animals were recovered for 7 days, at which point they were euthanized and the catheter pieces were removed and biofilm formation was assessed via CFU counts following sonication to remove adherent bacteria.

EXAMPLES

Example 1: Preparation of Binary Coating

The polymers used in this study are commercially available or have been synthesized by aqueous atom transfer radical polymerization (ATRP). Gel permeation chromatography (GPC) was used to determine the molecular weight and polydispersity (PDI) of the polymers (TABLE 1). The one-step deposition consists of two basic components: a hydrophilic polymer and dopamine. The polymers are co-dissolved with dopamine-hydrochloride in a pH=8.5 solution, in which the substrates are immersed at room temperature in air (FIG. 1A).

TABLE 1

Characteristics of the hydrophilic polymer used in this study, including dry thickness of the deposited film on silicon wafer:

| Polymer | Mn | Mw | PDI | Rh (nm) | Thickness (nm) |
|---|---|---|---|---|---|
| PDA | | | | | 32.2 ± 0.1 |
| *PDMA | 43K | 102K | 2.38 | 8.9 | 33.8 ± 0.4 |
| *PDMA | 146K | 209K | 1.43 | 13.0 | 21.9 ± 0.4 |
| *PDMA | 213K | 356K | 1.67 | 15.5 | 20.8 ± 0.1 |
| *PDMA | 412K | 555K | 1.35 | 20.4 | 18.3 ± 0.6 |
| *PDMA | 795K | 1260K | 1.58 | 28.1 | 18.9 ± 1.3 |
| *PDMA | 996K | 1290K | 1.30 | 29.2 | 17.7 ± 0.4 |
| *PAM | 441K | 614K | 1.39 | 21.4 | 20.7 ± 0.2 |
| *PHMA | 503K | 1200K | 2.38 | 19.7 | 12.0 ± 0.1 |
| *PHEA | 932K | 1290K | 1.38 | 33.4 | 16.0 ± 0.1 |

TABLE 1-continued

Characteristics of the hydrophilic polymer used in this study, including dry thickness of the deposited film on silicon wafer:

| Polymer | Mn | Mw | PDI | Rh (nm) | Thickness (nm) |
|---|---|---|---|---|---|
| *PTHMAM | 632K | 1050K | 1.66 | 21.7 | 8.9 ± 0.1 |
| *PHPMA | 824K | 1150K | 1.39 | 24.2 | 24.5 ± 0.2 |
| *PMPDSAH | 968K | 1160K | 1.19 | 16.2 | 12.5 ± 0.2 |
| *PMPC | 1310K | 1600K | 1.22 | 28.4 | 12.7 ± 0.1 |
| *PVP | ND | 1300K | ND | ND | 2.3 ± 0.2 |
| *PEO | ND | 900K | ND | ND | 8.2 ± 0.4 |
| *HPG | 703K | 865K | 1.23 | ND | 14.6 ± 0.2 |
| *Dextran | 705K | 1190K | 1.68 | ND | 16.8 ± 0.2 |

*with PDA weight PDMA. Further characterization of the coating was performed using contact angle measurements and ATR-FTIR measurements.

TABLE 2A

Comparison of chemical compositions of various deposited coatings on silicon wafers based on X-ray Photoelectron Spectroscopy (XPS) Analysis.

| POLYMER | Si (AT %) | C (AT %) | N (AT %) | O (AT %) | N/O | N/C | O/C |
|---|---|---|---|---|---|---|---|
| PDA only | 0.72 | 70.09 | 7.73 | 21.46 | 0.360 | 0.110 | 0.306 |
| *PDMA43K | 1.19 | 72.50 | 8.20 | 18.11 | 0.453 | 0.113 | 0.250 |
| *PDMA213K | 0.82 | 71.16 | 10.21 | 17.81 | 0.573 | 0.143 | 0.250 |
| *PDMA795K | 0.45 | 71.67 | 10.67 | 17.21 | 0.620 | 0.149 | 0.240 |

*with PDA

TABLE 2B

Comparison of chemical compositions of various deposited coatings on silicon wafers based on X-ray Photoelectron Spectroscopy (XPS) Analysis.

| POLYMER | Si | C | N | O | S | P | N/O | N/C | O/C |
|---|---|---|---|---|---|---|---|---|---|
| Silicone only | 50.65 | 9.38 | 0 | 39.97 | 0 | 0 | 0 | 0 | 4.26 |
| *PMPDSAH | 4.51 | 64.07 | 7.38 | 20.74 | 3.30 | 0 | 0.36 | 0.12 | 0.32 |
| *PMPC | 3.53 | 63.23 | 5.97 | 25.13 | 0 | 2.14 | 0.24 | 0.09 | 0.40 |
| *PVP | 31.41 | 37.75 | 5.66 | 25.28 | 0 | 0 | 0.22 | 0.15 | 0.67 |
| *PEO | 13.80 | 55.87 | 5.63 | 24.70 | 0 | 0 | 0.23 | 0.10 | 0.44 |
| *HPG | 1.64 | 64.27 | 3.75 | 30.34 | 0 | 0 | 0.12 | 0.06 | 0.47 |
| *DEXTRAN | 1.07 | 64.76 | 5.53 | 28.63 | 0 | 0 | 0.19 | 0.09 | 0.44 |

*with PDA

Example 2: Dependence of the Molecular Weight of the Polymer on the Physical and Biological Properties of the Coating Silicon wafer was used as a model surface determining the properties of the coating and study the polymerization of process. PDMA having different molecular weights ranging from 43K Da to 996K Da (TABLE 1) was used for the preparation of the coating. Small pieces of silicon wafer were immersed in a solution of the polymer and dopamine at room temperature for 24 h without stirring and were rinsed thoroughly with tris-buffered saline and water followed by drying in a flow of argon gas. Ellipsometry measurements were used for the determination of the thickness of the coating. PDA gave a dry thickness of 32.2±0.1 nm on the surface. The binary coating prepared by mixing PDMA and dopamine gave thicknesses in the range from 17.7 to 33.8 nm (TABLE 1). The thickness of the coating decreased with increasing molecular weight of the PDMA used.

Figure 2A:
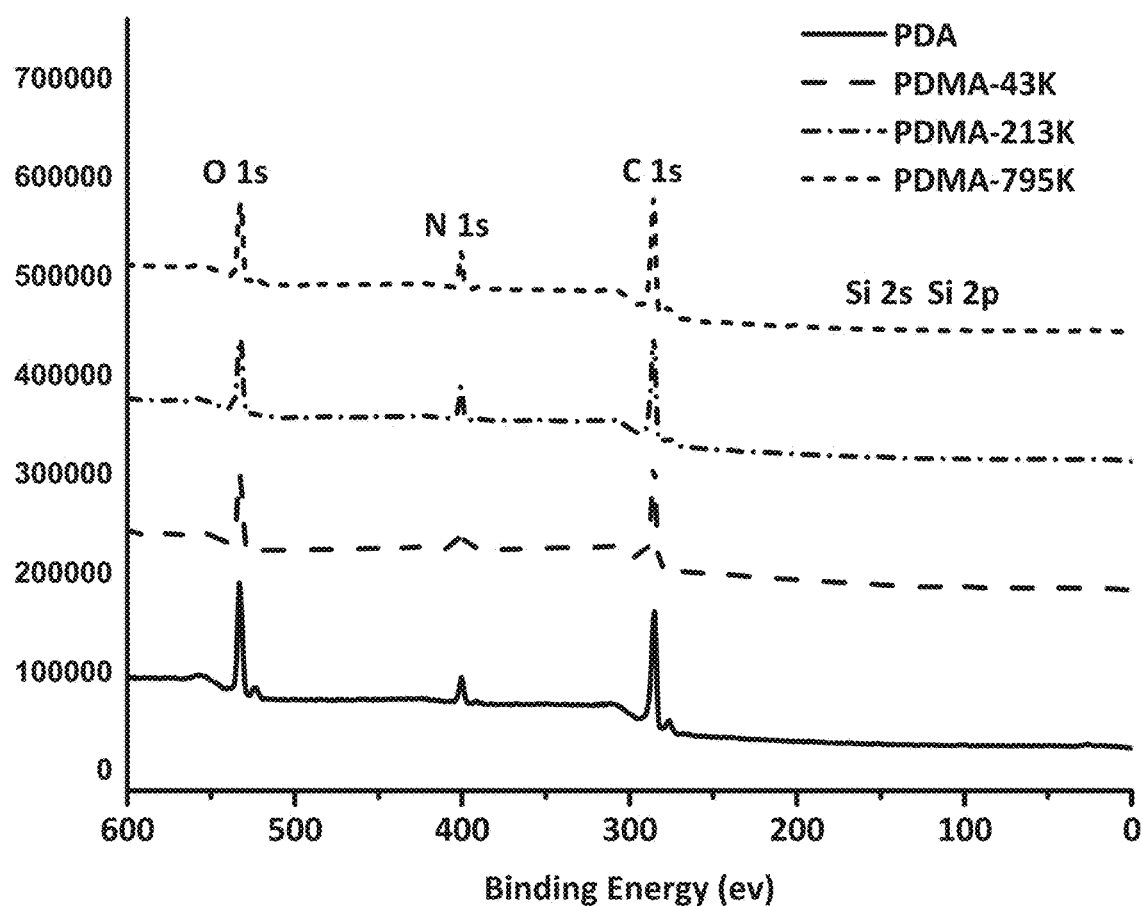
FIG. 2A shows surface characterization (binding energy (ev)) of PDA, PDA/PDMA-43K, PDA/PDMA-213K and, PDA/PDMA-795K coated silicon wafers by XPS spectra.
Figure 2B:
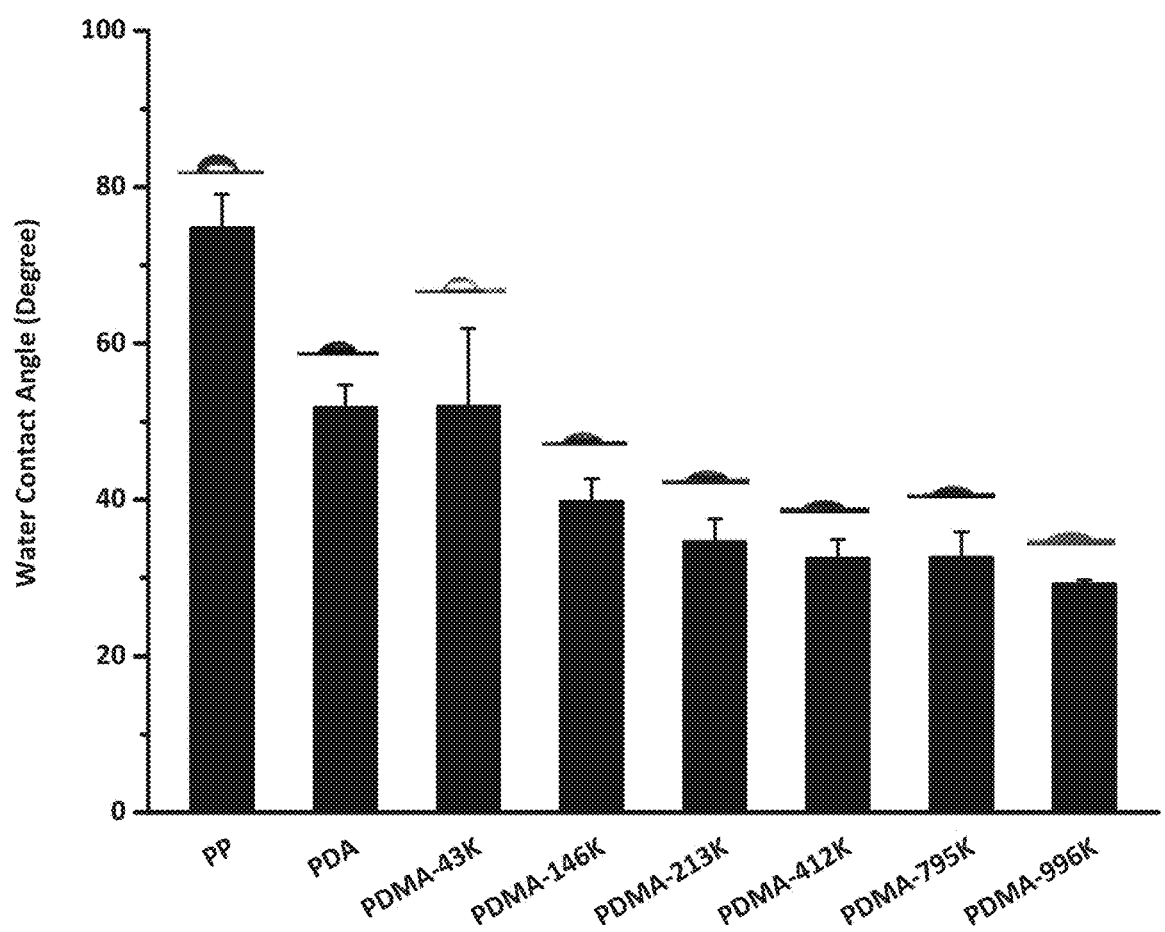
FIG. 2B shows water contact angles for polypropylene (PP) substrate, PP coated in PDA, PP coated in PDA/PDMA-43K, PP coated in PDA/PDMA-146K, PP coated in PDA/PDMA-213K, PP coated in PDA/PDMA-412K, PP coated in PDA/PDMA-795K and PP coated in PDA/PDMA-996K.
Figure 7A:
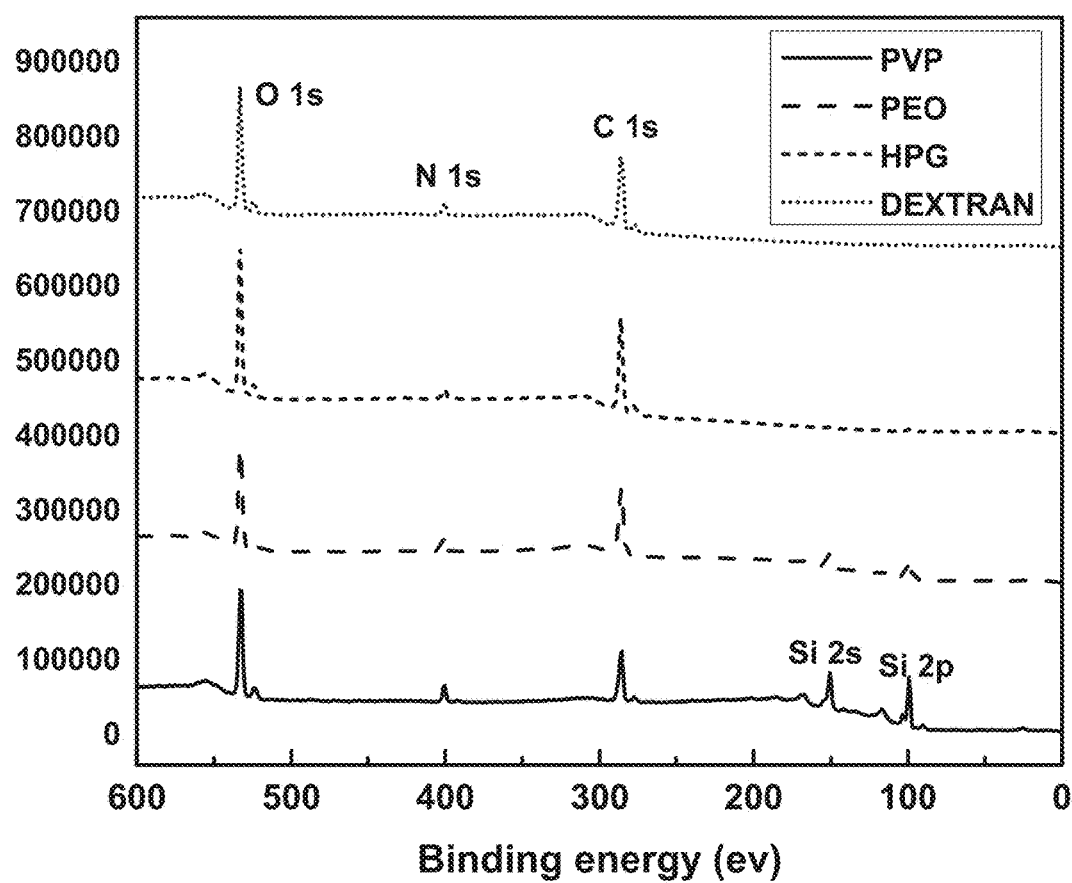
FIG. 7A shows wide scan of the high molecular weight PVP, PEO, HPG, and Dextran coated silicon wafers by XPS spectra, with detailed nitrogen (N1S) Spectra of PMPDSAH and PMPC coated silicon wafers characterized by XPS spectra.
Figure 7B:
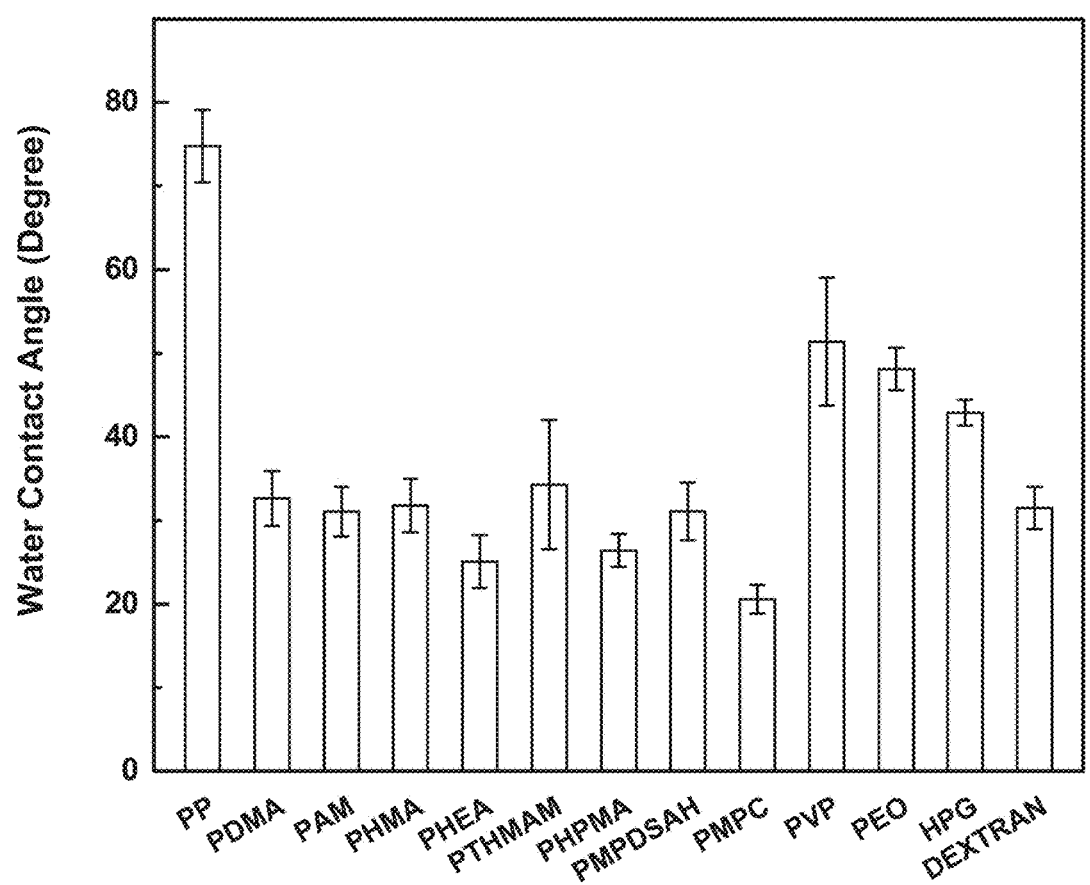
FIG. 7B shows water contact angles of uncoated PP and PDA with: HMW PDMA; HMW PAM; HMW PHMA; HMW PHEA; HMW PTHMAM; HMW PHPMA; HMW PMPDSAH; HMW PMPC; HMW PVP; HMW PEO; HPG; and Dextran, deposited PP substrates.

The chemical composition of the deposited coating was determined using XPS analysis. A comparison of PDA coating and binary PDA-PDMA coating is shown in FIG. 2A and TABLE 2A. Similarly, a comparison of high molecular weight PVP, PEO, HPG, and Dextran coated silicon wafers by XPS spectra is shown in FIG. 7A and TABLE 2B. The intensity of the nitrogen peak increased with increasing molecular weight of the PDMA. The coating prepared using the PDMA 795K showed higher intensity of nitrogen and lower intensity of oxygen, indicating more PDMA was incorporated into the coating. This fact was also verified from the increased intensity of C=O component in the C is detail spectrum of the coating prepared using high molecular After successful preparation of the coating on silicon surface, a similar protocol was used to prepare a coating on polypropylene (PP) film. The binary coating on the PP surface was evidenced from the static water contact angle and ATR-FTIR analyses. Coating of the PP substrate with binary coating led to a considerable decrease in the static water contact angle from 73° for the bare PP film to 29° for the binary coating that used 996 K PDMA (FIG. 2B). Similarly, FIG. 7B shows water contact angles of uncoated PP as compared to PDA/PDMA, PDA/PAM, PDA/PHMA, PDA/PHEA, PDA/PTHMAM, PDA/PHPMA, PDA/PMPDSAH, PDA/PMPC, PDA/PVP, PDA/PEO, PDA/HPG and PDA/Dextran deposited PP substrates. The decrease in static water contact angle represents a decrease in hydrophobicity of the coating. ATR-FTIR spectra also provided information on the chemical compositions of the coatings. The pure PDA coating showed two distinctive peaks at 1617 $cm^{-1}$ and 1510 $cm^{-1}$, which were attributed to the overlap of the C=C vibrations in the aromatic ring and the N—H bending vibrations, respectively. An increase in absorbance at 1622 $cm^{-1}$ was seen for the binary PDA-PDMA coating, demonstrating the incorporation of PDMA component into the coating.

Figure 2C:
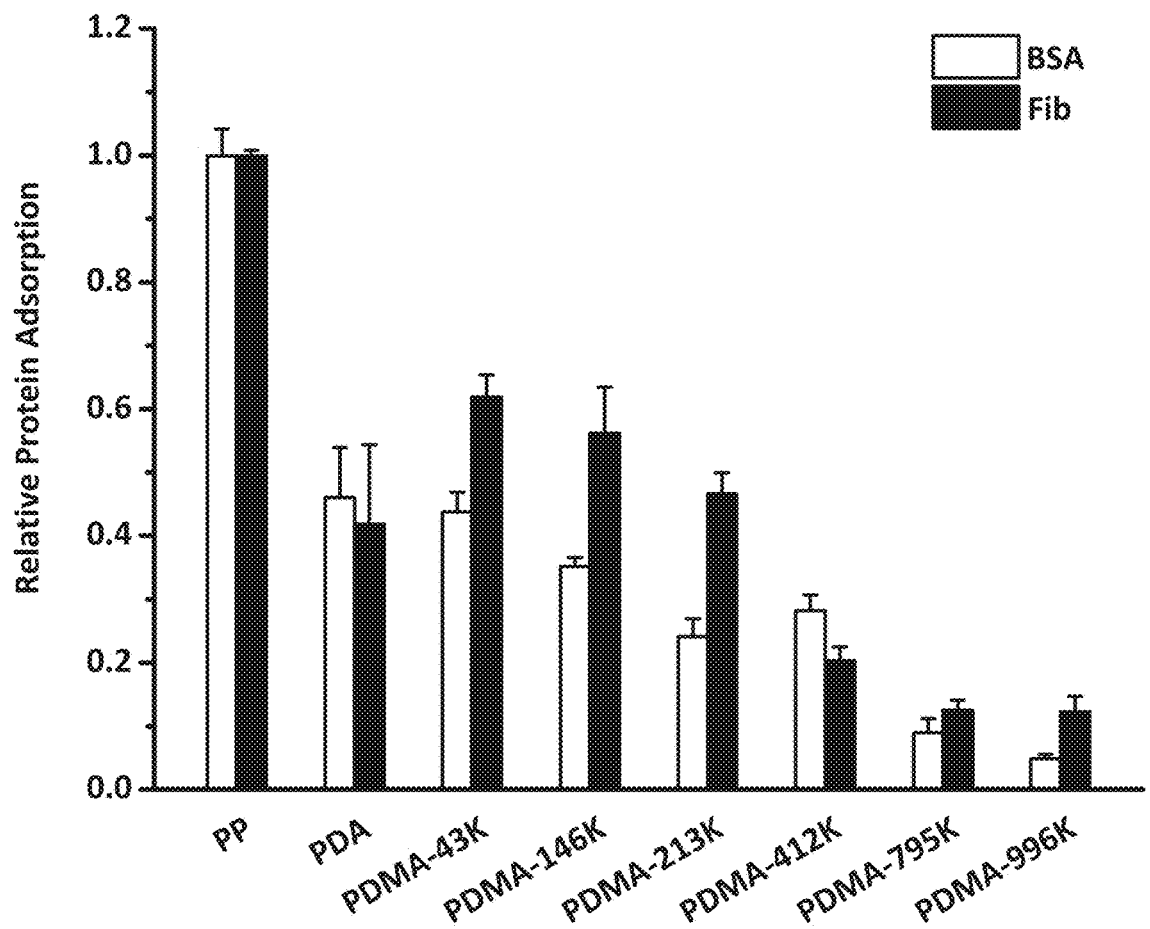
FIG. 2C shows adsorption of bovine serum albumin (BSA) and Fibrinogen (Fib) onto the different molecular weight PDMAs (i.e. PP coated in PDA/PDMA-43K, PP coated in PDA/PDMA-146K, PP coated in PDA/PDMA-213K, PP coated in PDA/PDMA-412K, PP coated in PDA/PDMA-795K and PP coated in PDA/PDMA-996K) deposited PP films as compared to uncoated PP and PDA only coated PP.

The initial screening of antifouling properties of the binary coating (i.e. PDA) prepared from different molecular weight PDMAs on PP films were tested using single protein adsorption and biofilm formation. The ability to resist non-specific protein adsorption was tested by incubating the unmodified (i.e. PP only), PDA coated PP, PDA/PDMA-43K coated, PDA/PDMA-146K coated, PDA/PDMA-213K coated, PDA/PDMA-412K coated, PDA/PDMA-795K coated and PDA/PDMA-996K coated PP surfaces with 0.25 mg/ml fibrinogen (Alex Fluor-594 conjugate) and FITC labeled-BSA for 2 h, and then thoroughly washing. The coating was evaluated by fluorescence microscopy measurements taken before protein incubation and after incubation. Fluorescently labeled proteins, FITC labeled-BSA and Alex Fluro594 fibrinogen (Fib), were used for evaluation (micrographs not shown). The high molecular weight PDMA-996K deposited surface significantly reduced the BSA and Fib adsorption compared to unmodified samples, as evident from 95.0% and 88.7% reduction in fluorescence intensity (FIG. 2C) reflecting the performance of the coating and the dependence on the molecular weight.

Figure 2D:
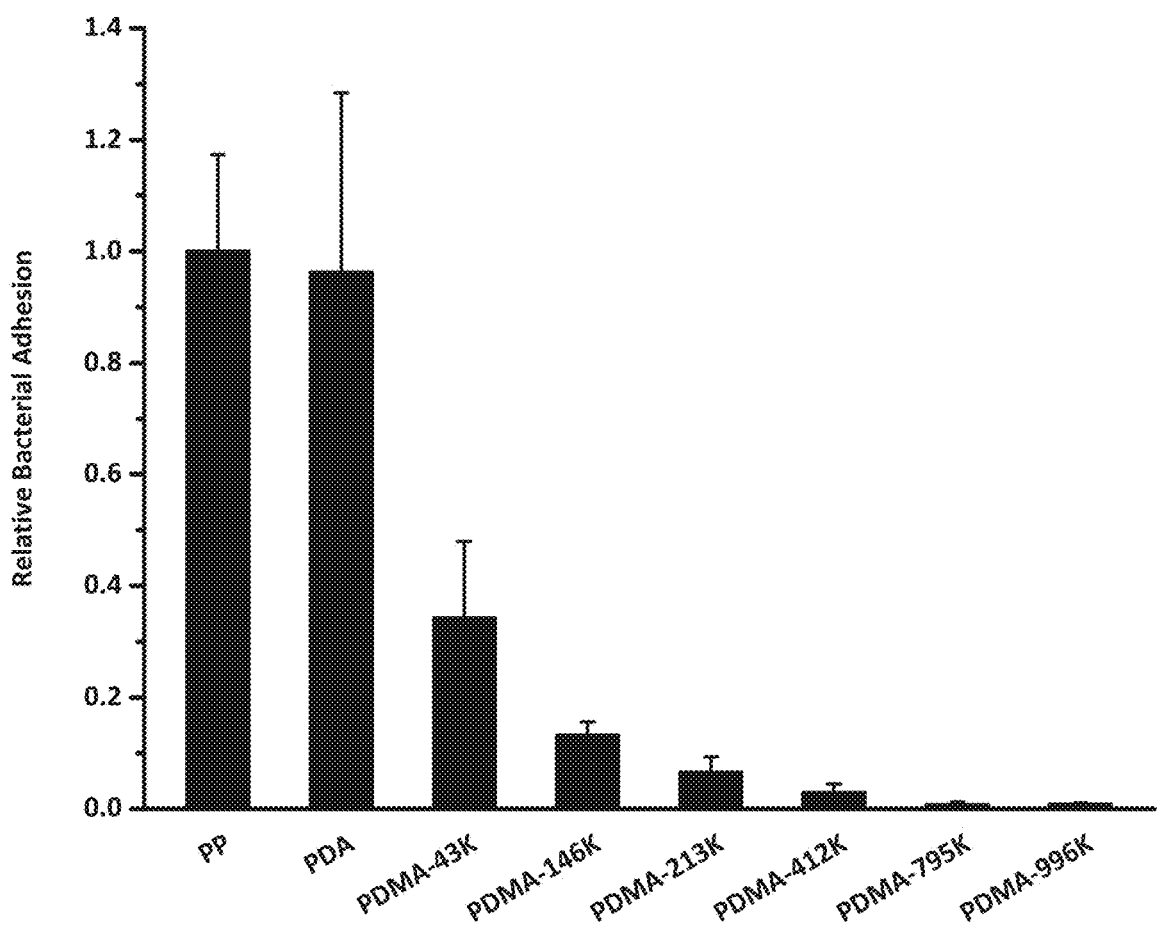
FIG. 2D shows normalized bacterial density of adhered *S. aureus* on uncoated PP and PDA only coated PP, as compared to PP coated in PDA/PDMA-43K, PP coated in PDA/PDMA-146K, PP coated in PDA/PDMA-213K, PP coated in PDA/PDMA-412K, PP coated in PDA/PDMA-795K and PP coated in PDA/PDMA-996K.
Figure 3A:
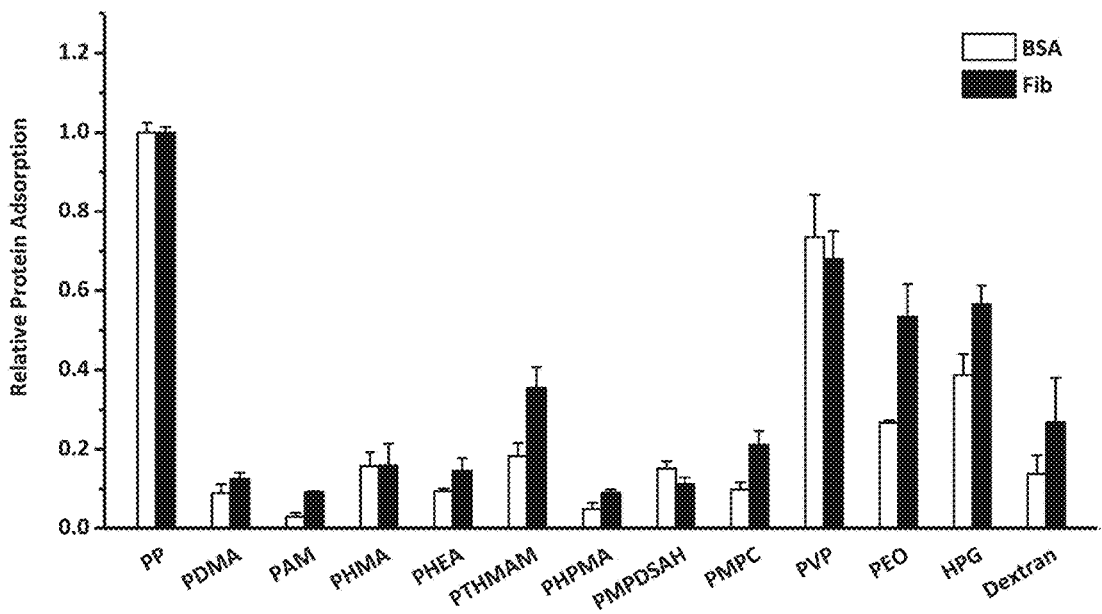
FIG. 3A shows relative adsorption of BSA and Fib on uncoated PP, as compared to high molecular weight PDMA, PAM, PHMA, PHEA, PTHMAM, PHPMA, PMPDSAH, PMPC, PVP, PEO, HPG and dextran compositions with PDA, wherein adsorption was measured at 2 h at 37° C.
Figure 3B:
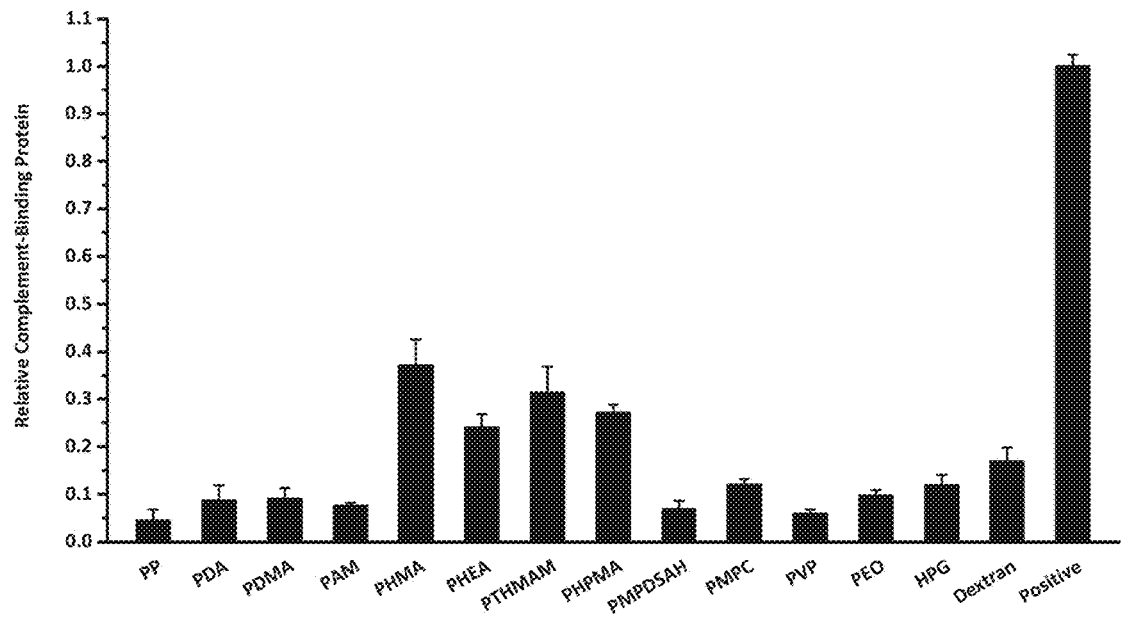
FIG. 3B shows complement activation on uncoated PP, as compared to high molecular weight PDMA, PAM, PHMA, PHEA, PTHMAM, PHPMA, PMPDSAH, PMPC, PVP, PEO, HPG and dextran compositions with PDA, wherein samples were incubated with fresh serum for 2 h.
Figure 3C:
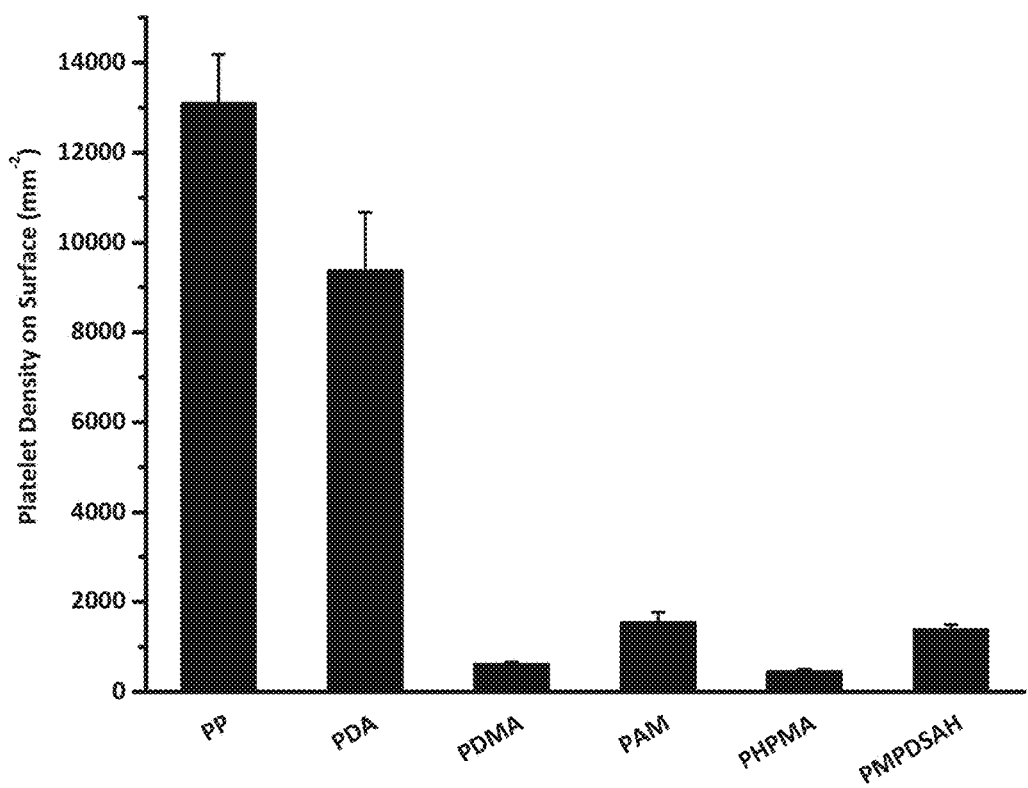
FIG. 3C shows platelet adhesion on the high molecular weight hydrophilic polymers (i.e. PDMA, PAM, PHPMA and PMPDSAH) deposited with PDA on PP surfaces relative to that on the uncoated PP surface and PDA alone.
Figure 3D:
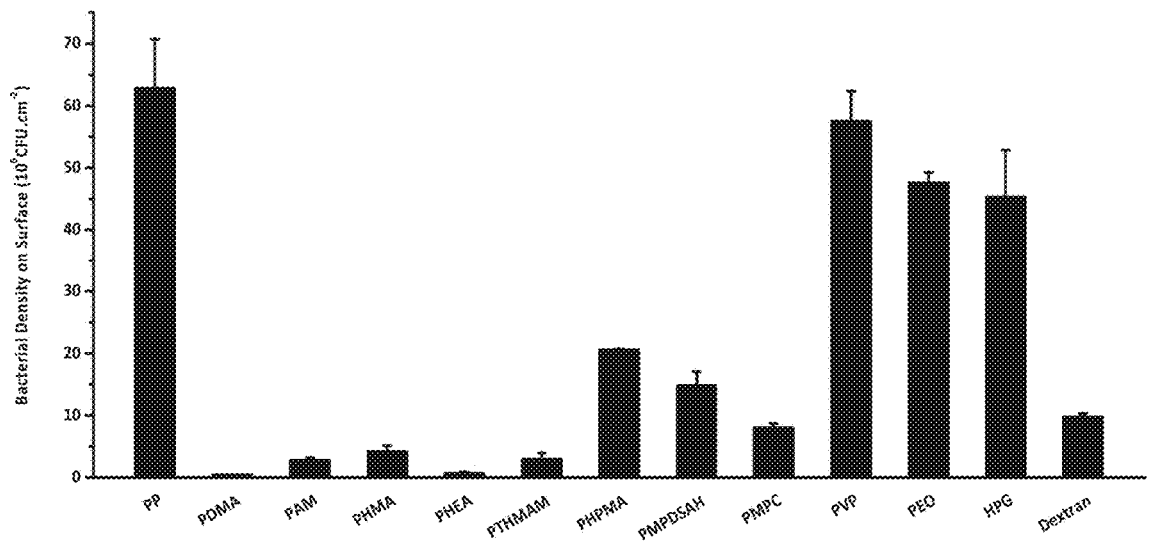
FIG. 3D shows normalized count of adherent *S. aureus* after incubation in LB containing $10^6$ starting cells/ml for 24 h as determined by the SEM images, wherein uncoated PP and PDA only coated PP, are compared to high molecular weight PDMA, PAM, PHMA, PHEA, PTHMAM, PHPMA, PMPDSAH, PMPC, PVP, PEO, HPG and dextran compositions with PDA.

To screen the anti-biofilm performance of polymer coatings, the unmodified (i.e. PP only), PDA coated PP, PDA/PDMA-43K coated, PDA/PDMA-146K coated, PDA/PDMA-213K coated, PDA/PDMA-412K coated, PDA/PDMA-795K coated and PDA/PDMA-996K coated PP surfaces were incubated with S. aureus suspension for 24 h. The number of bacteria that adhered on the surface was determined by SEM analysis and CFU counts images. The SEM analysis revealed (micrographs not shown) very few S. aureus cells adhered on the coating prepared using high molecular weight PDA/PDMA whereas large amount of S. aureus cells were found on both unmodified PP and PDA coated PP surfaces. In particular, PDA/PDMA-795K coated and PDA/PDMA-996K coated PP surfaces showed a reduction in biofilm formation of S. aureus cells by 99.3% and 99.2% (FIG. 2D), respectively compared to pristine PP surface. Similarly, relative bacterial adhesion of S. aureus on uncoated PP, PDA coated PP, high molecular weight PDMA, PAM, PHMA, PHEA, PTHMAM, PHPMA, PMPDSAH, PMPC, PVP, PEO, HPG and dextran compositions with PDA are shown after 24 (FIG. 3D). Consistently, the least S. aureus bacterial adhesion was shown with coatings of PDA with either PDMA, PAM, PHMA, PHEA or PHPMA, wherein the hydrophilic polymer was a high molecular weight polymer.

Further long term biofilm studies with S. aureus lux: uncoated TiO$_2$ and coated (PDMA-795 k/PDA) (5:1) TiO$_2$ were placed on 24-well plates in a total volume of 1 ml Tryptic Soy Broth (TSB) culture containing 500,000 cells/ml was added to each well. After every 24 hours, suspension was removed and new TSB culture with 500,000 cells/ml was added. At days 3 and 7, the samples were thoroughly washed and the fluorescent stain Syto-9™ was used to microscopically assess the surface-attached biomass. The samples were anayzed using a confocal laser scanning microscope.

Visulization of the uncoated sample demostrated S. aureus biofilm formation after 3 days. However, the coated surfaces demostrated markedly delayed surface colonization, with very few bacteria on the surface on day 3. Similar observations were made on day 7, where biofilm formation was significantly reduced on coated sample relative to that of uncoated sample.

Example 2: Dependence on Polymer Chemistry of the Properties of the Coatings

The coating technique was adapted to other high molecular weight hydrophilic polymers. As shown in (FIG. 1B), a small library of twelve hydrophilic polymers with high molecular weight was selected to provide wide chemical diversity, including linear neutral polymers, linear zwitterionic polymers, and branched polymers. The molecular weight of the polymers ranged from 441 k to 1310 k and hydrodynamic size ranging from 16.2 nm to 29.2 nm. The deposition of different polymers assisted by dopamine was first examined on the silicon wafers. PVP, PEO, and PTHMAM were among the thinnest layers with values of 2.3±0.2 nm, 8.2±0.4 nm, and 8.9±0.1 nm, respectively, while other polymer coatings gave layers around 12.0 nm-24.5 nm (TABLE 1). The X-ray photoelectron spectroscopy (XPS) wide scans, S 2p or P 2p core-level spectra of the PMPDSAH and PMPC coatings were measured (data not shown). As expected, the sulfur (S) peak was detected in PMPDSAH coated sample and phosphorus (P) peak was detected in PMPC coated sample, demonstrating the incorporation of these polymers. Furthermore, a nitrogen peak appeared at 403.0 eV, which was attributed to the cationic nitrogen in the zwitterionic polymers, was detected in both PMPDSAH and PMPC coated samples, confirming the deposition of these hydrophilic polymers. In the case of HPG and Dextran coated samples, an overall increase of oxygen was visible in widescan mode, indicating the successful incorporation of these hydrophilic polymers. The PEO incorporated coatings behaved differently than HPG and Dextran coatings, showing no change on the intensity of oxygen compared to PDA coating indicating the poor incorporation of PEO on the surface coating. The difference in water contact angle of PDA and high molecular weight polymer coated PP films also provided evidence that most of the high molecular weight polymers were incorporated into the coatings. Other than PEO and PVP coatings, a decrease in static water contact angle was observed for all other coatings compared to the pure PDA coating. In addition, the deposited hydrophilic polymers could be clearly detected by ATR-FTIR spectra on PP films.

To investigate the antifouling performance of coatings with diverse chemical compositions, unmodified and modified PP films were analyzed for protein adsorption, complement protein binding, platelet adhesion, and biofilm formation. Compared to control PP films, most of the PP films coated with binary coating composed of hydrophilic high molecular weight polymers were able to strongly reduce the adsorption of both proteins. In the case of PDMA, PAM, and PHPMA coated samples, the BSA and Fib adsorptions on these modified samples were only approximately 5% and 10% compared to the controls (FIG. 3A). The complement protein (C3) determined based on intensity of anti-C3b adsorption of the surface is shown in FIG. 3B, wherein the polymers containing —OH groups induced significant antibody binding compared to the other polymers and control samples. Accordingly, PHMA, PHEA, PTHMAM and PHPMA would not likely be chosen as the hydrophilic polymer, where the substrate to be coated is intended for contact with blood or fractions thereof. The ability of the coatings to prevent platelet adhesion was also tested, wherein SEM images of uncoated, PDA coated, PDA with HMW PDMA, PAM, PHPMA and PMPDSAH PP substrates were examined platelet adhesion after incubation with buffy-coated PRP for 4 h. (micrographs not shown). The binary coating composed PDA and HMW hydrophilic polymers (i.e. PDMA, PAM, PHPMA and PMPDSAH) reduced the platelet adhesion dramatically compared to the control PP surface. Compared to uncoated PP substrate, the number of adhered platelets decreased by 95.4%, 88.2%, 96.6%, and 89.5% on PDMA, PAM, PHPMA, and PMPDSAH based coatings, respectively (FIG. 3C).

As discussed briefly above, the biofilm formation on the coatings and the influence of chemistry of the polymers were also investigated. Incubation of S. aureus in Luria Bertani (LB) medium for 24 h led to the formation of a thick biofilm on unmodified PP substrate, whereas significantly reduced biofilm formation was detected on binary coating prepared from hydrophilic polymers (FIG. 3D). Differences were detected between the different polymers used for the coating showing that the choice of the hydrophilic polymer in the coating is of importance. In particular, PDA combined with certain HMW hydrophilic polymers (i.e. PDMA, PAM, PHMA, PHEA and PHPMA) showed the best reduction in bacterial adhesion for S. aureus.

Example 3: Universality of the Approach and Stability of the Coating

Figure 4A:
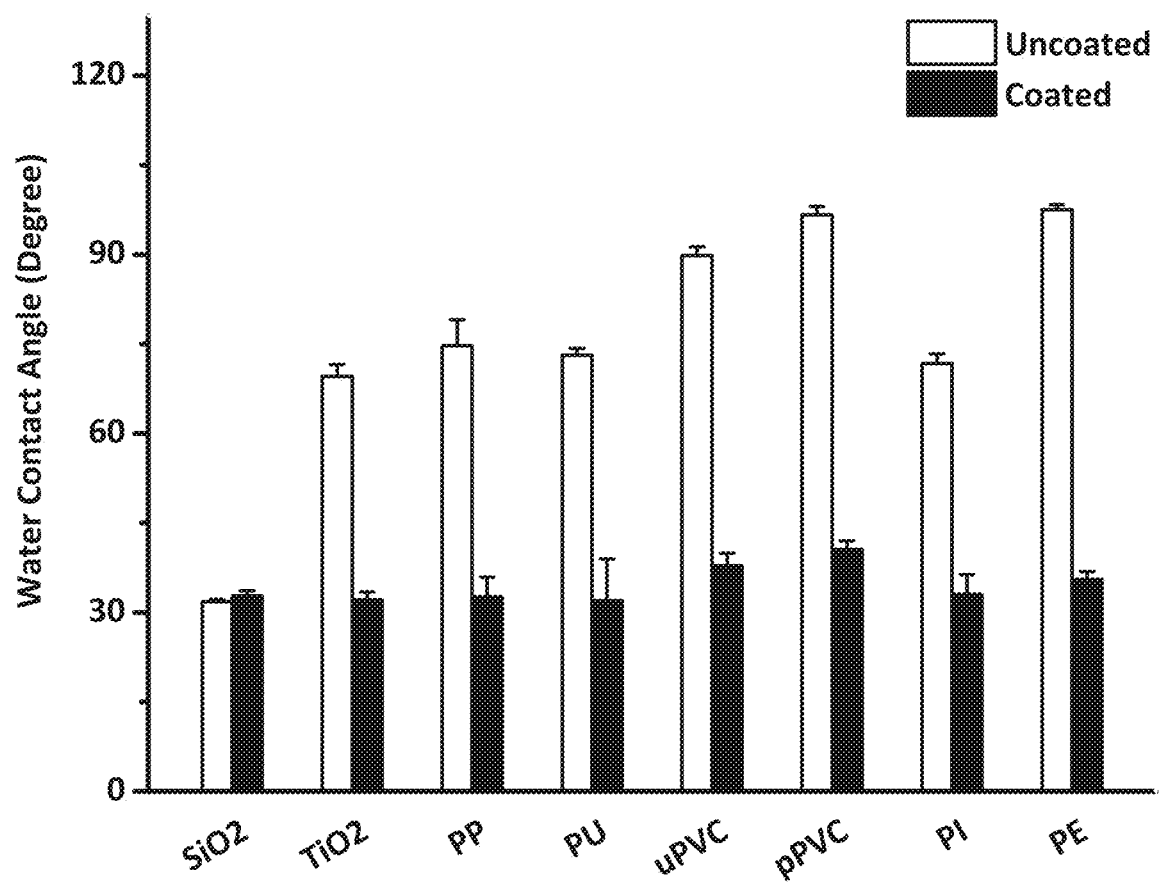
FIG. 4A shows water contact angles of uncoated and PDMA-795K coated substrates for a variety of substrates (i.e. Si, $TiO_2$, PP, PU, UPVC, PPVC, PI and PE).

The performance of the coating prepared using 795K PDMA and PDA was tested on a variety of substrates (i.e. TiO$_2$, polypropylene (PP), polyurethane (PU), polyethylene (PE), unplasticized polyvinyl chloride (uPVC), plasticized PVC (pPVC) and polyimide (PI)). All substrates were immersed in solutions containing dopamine and 795K PDMA. After the coating process the wettability changes of the substrates were measured via water contact angle measurements. Coatings on all the substrates showed significant decrease in water contact angle compared to the uncoated surfaces (FIG. 4A) except SiO$_2$. Similarly, the protein adsorption and biofouling measurements showed excellent resistant against protein and bacterial adhesion. Accordingly, the results suggest that the combination of HMW PDMA and PDA is useful for coating a wide range of substrates and provides significant resistance against protein and bacterial adhesion.

Figure 4B:
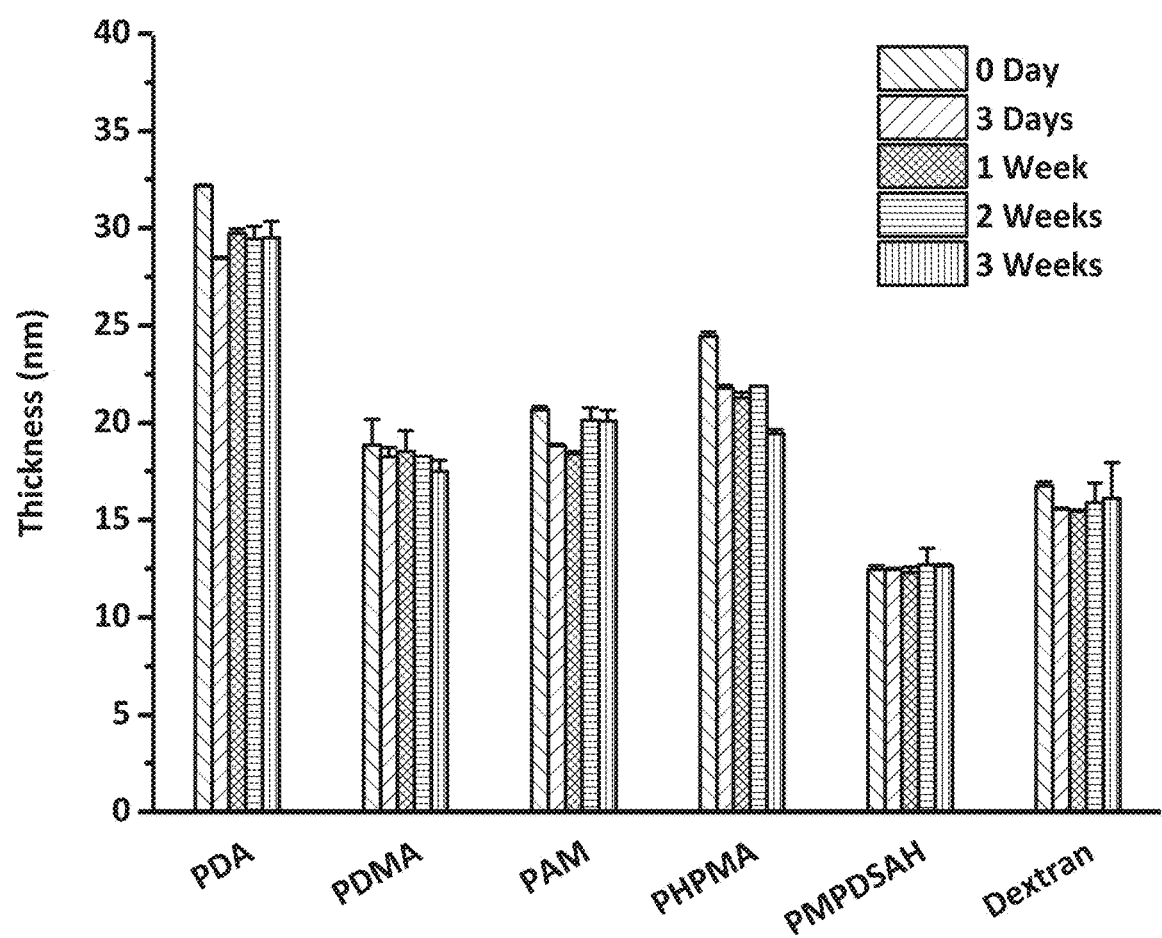
FIG. 4B shows the thickness of high molecular weight deposited coatings on silicon surfaces after 0 days, 3 days, 1 week, 2 weeks and 3 weeks of incubation in PBS buffer, as determined by ellipsometry.

The stability of the coating was investigated by measuring the thickness of the coating prepared on silicon wafer stored over extended periods of time in PBS buffer (pH 7.4) (up to 3 weeks), wherein different HMW hydrophilic polymers combined with PDA were compared (i.e. PDMA, PAM, PHPMA, PMPDSAH and dextran) to PDA alone. Results shown in FIG. 4B indicate that no significant changes in thickness upon storage. Furthermore, the stability of the coating after 10 minutes sonication was studied, which showed a slight decrease in the thickness (~10% reduction), however, this change did not result in any increase in bio-adhesion by the coating.

Figure 4C:
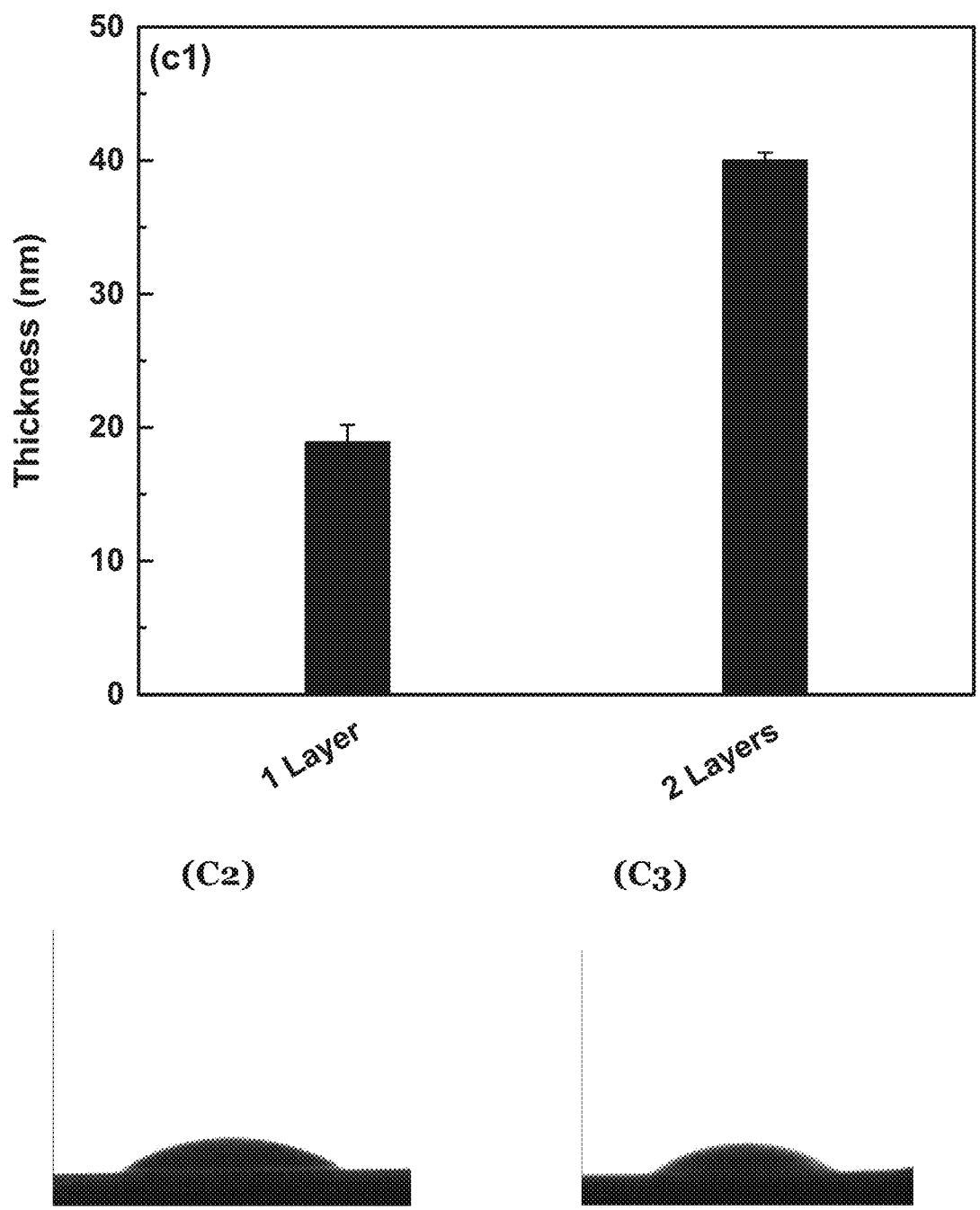
FIG. 4C shows (c1) Ellipsometric thickness of PDMA-795K coatings on silicon substrate after 1 cycle and 2 cycles of deposition (i.e. deposition followed by drying and subsequence second deposition and second drying); (c2) Water contact angle of PDMA-795K coating on PP substrate after 1 cycle of deposition; (c3) Water contact angle of PDMA-795K coating on PP substrate after 2 cycles of deposition.
Figure 8A:
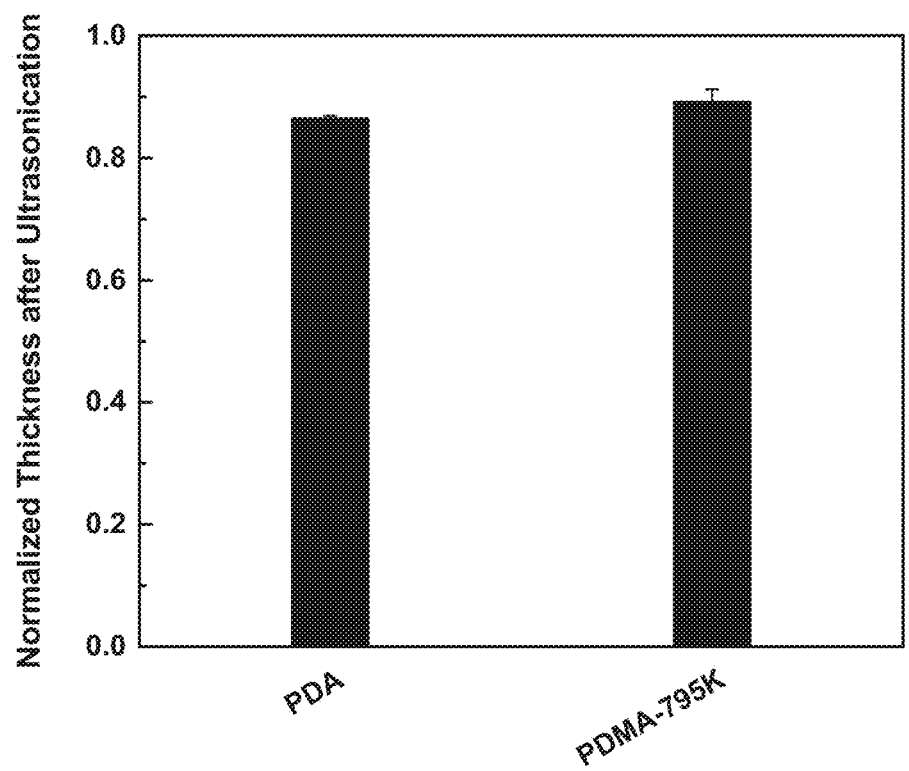
FIG. 8A shows normalized thickness of polydopamine and PDMA-795K deposited coatings on silicon wafers after 10 minutes ultrasonication in PBS buffer, as determined by ellipsometry.
Figure 8B:
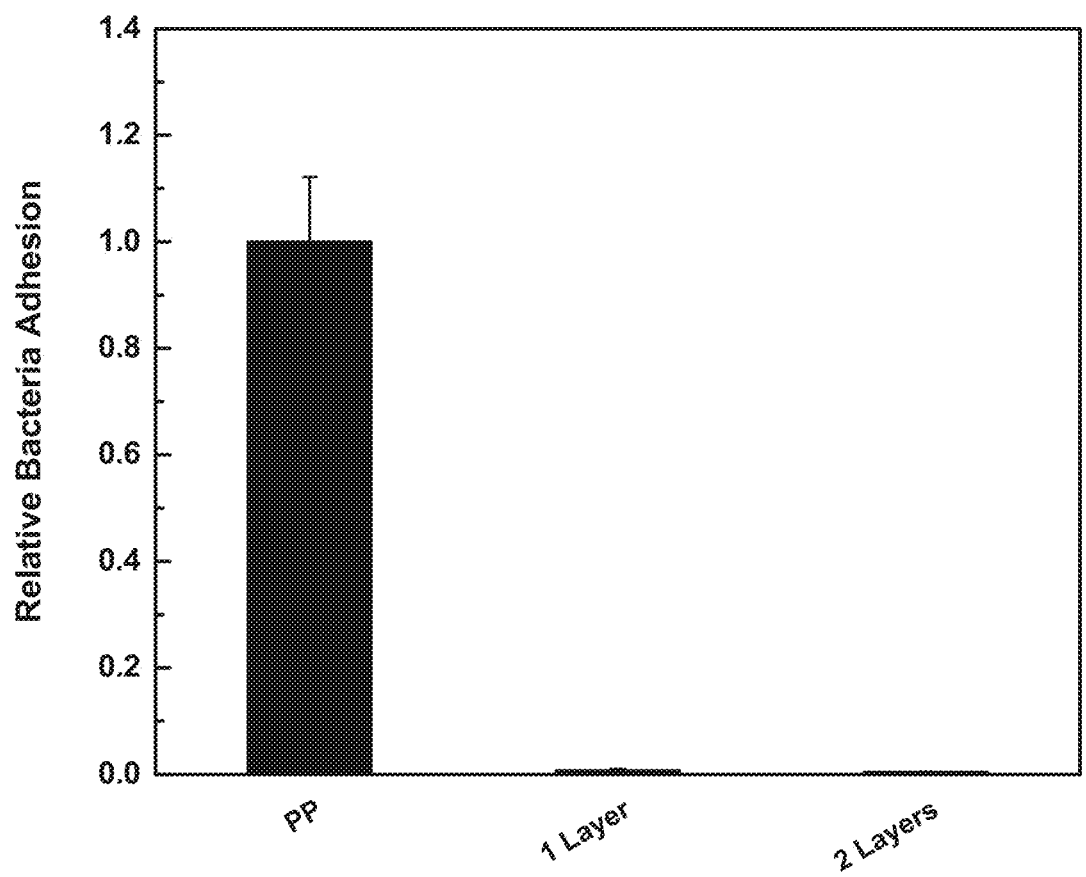
FIG. 8B shows relative biofilm formation of S. aureus on 1 layer and 2 layers PDA/PDMA-795K coated polypropylene films after 24 h incubation in LB medium determined by SEM images.
Figure 8C:
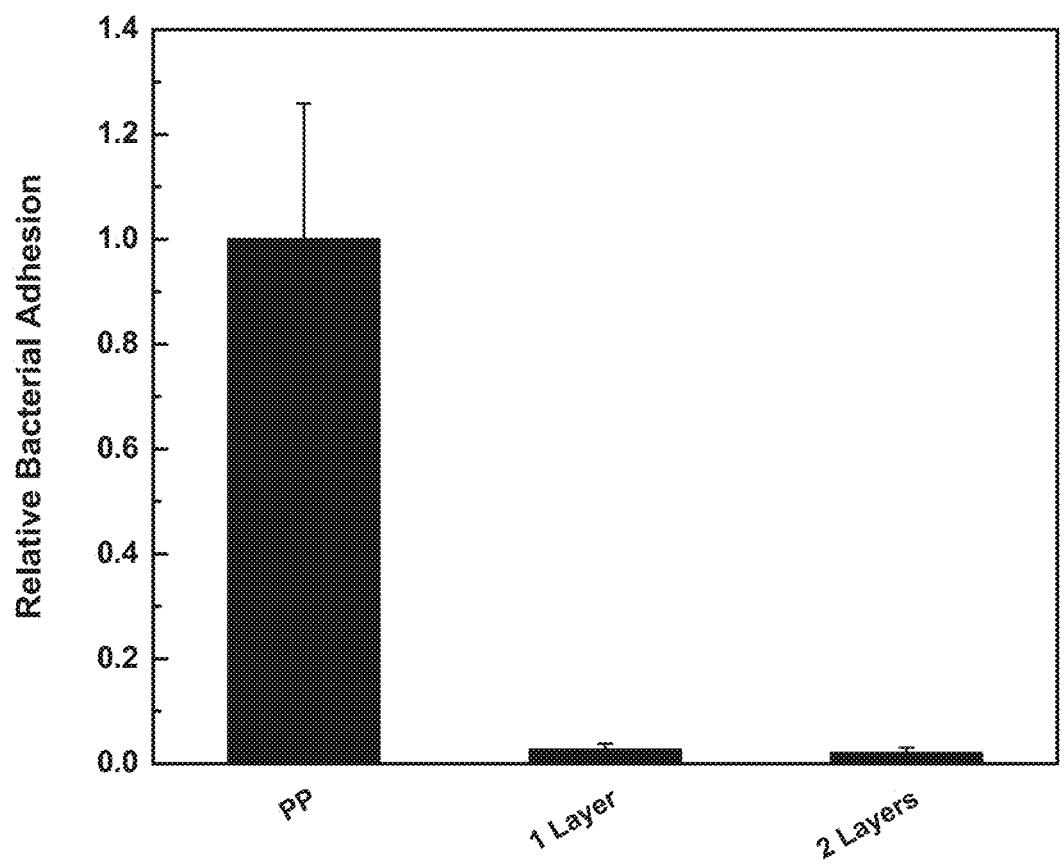
FIG. 8C shows relative biofilm formation of E. coli on 1 layer and 2 layers PDA/PDMA-795K coated polypropylene films after 24 h incubation in LB medium determined by SEM images.

The possibly of multilayer coating on the substrates to increase the thickness of the coating was also investigated. The studies showed that even after incubating over 24 h with the PDMA 795 and dopamine solution, the dry thickness of the coating never increased beyond 20 nm indicative of a uniform deposition of the particles and uncontrolled aggregation of the particles. Thus to increase the coating thickness, after initial drying of the coating, an additional layer of PDA-PDMA was deposited on the surface using similar methodology. As shown in FIG. 4C, the thickness of the initial layer was about 19 nm and nearly double thickness of the coating was obtained upon the addition of second layer. This potentially increased the robustness and the possibility of achieving desired thickness by controlling the dip coating process. A comparison of S. aureus and E. coli adhesion to uncoated PP substrate with 1 layer of PDA/PDMA-795K coated PP substrate and 2 layers of PDA/PDMA-795K coated PP substrate were tested. Although both single and double coated substrates showed a vast improvement in bacterial adhesions, the double layer coating had slightly improved biofilm resistant properties compared to the single layer coating (see FIGS. 8B and 8C).

Figure 5A:
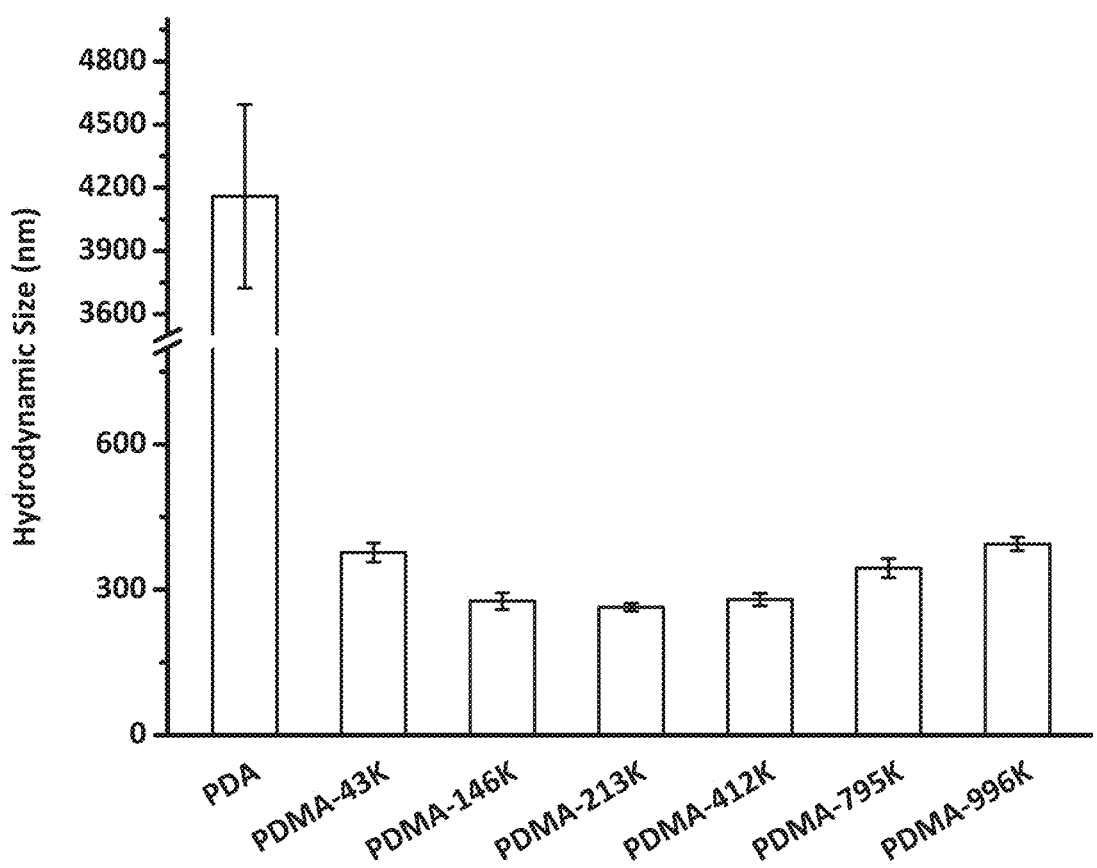
FIG. 5A shows a DLS study of particle formation (hydrodynamic size) in a TRIS buffered solution of dopamine and in a TRIS buffered solution of dopamine at different molecular weight PDMA.
Figure 9A:
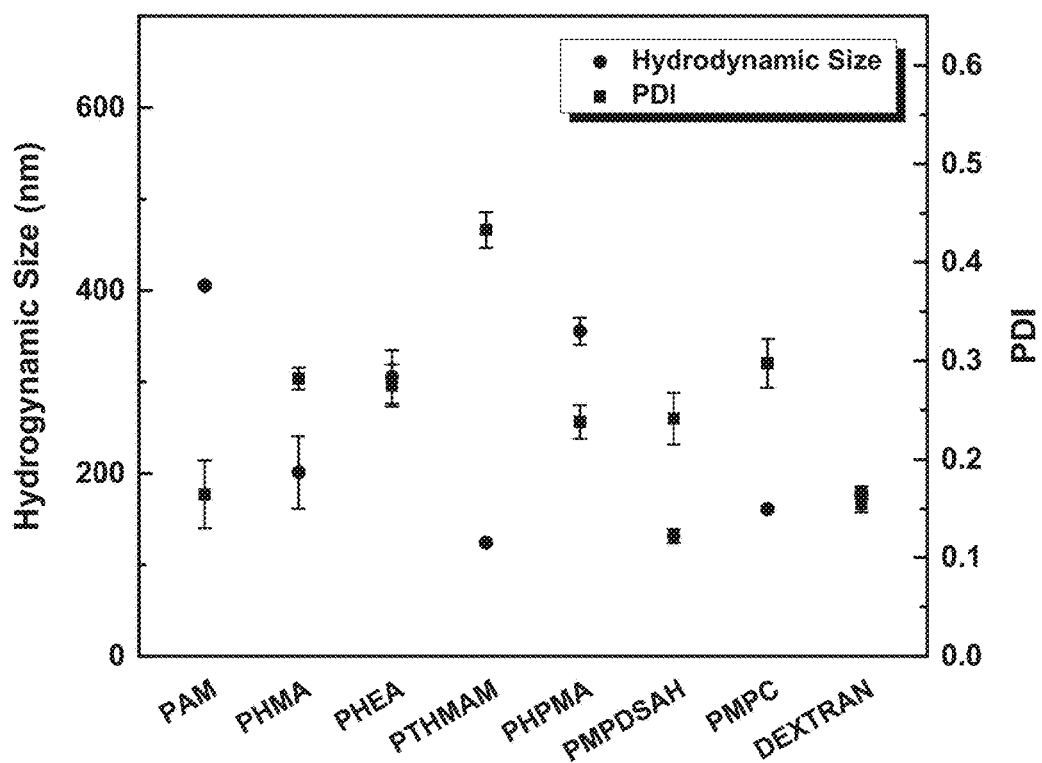
FIG. 9A shows DLS and TEM studies of particle formation in a TRIS buffered solution of dopamine and PAM, PHMA, PHEA, PTHMAM, PHPMA, PMPDSAH, PMPC, and Dextran.

Example 4: Mechanism of the Deposition Process and the Formation Antifouling Coating The results from the antifouling analyses demonstrated that the molecular weight and chemistry of the hydrophilic polymer used in the binary coating (i.e. polymeric binder and hydrophilic polymer) play an important role that determine the properties of the coating. A self-assembly process is involved in the formation polydopamine deposition on the surface. To investigate the mechanism of the coating process, the formation of PDA particles in presence of PDMA with different molecular weights (i.e. 43K, 146K, 213K, 412K, 795K and 996K) were investigated. The hydrodynamic size of the particles was measured using dynamic light scattering (DLS) and the size of the dry particles was measured using transmission electron microscopy (TEM) analysis. The average hydrodynamic size of the PDA in the absence of the polymer was around 4000 nm. PDA particles were highly unstable and resulted in aggregation. However, upon the addition of different molecular weight of the PDMA, particle size was significantly decreased (see TABLE 3). There was an initial decrease in particle size and then it increased with increases in molecular weight of the PDMA component (see FIG. 5A). The stability of the particles increased with increase in molecular weight of PDMA used. Similarly, hydrodynamic size and PDI were compared for PAM, PHMA, PHEA, PTHMAM, PHPMA, PMPDSAH, PMPC, and Dextran (see FIG. 9A).

TABLE 3

Number-averaged particle size of DPA and DPA/PDMA 1:5 ratio in pH 8.5 TRIS Buffered solution after 24 hours as determined by TEM

| SAMPLE | AVERAGE PARTICLE SIZE (NM) | SD (NM) | SWELLING RATIO |
|---|---|---|---|
| PDA | 4343.6 | 3330.3 | 0.958 |
| PDMA-43K | 301.9 | 36.4 | 1.247 |
| PDMA-213K | 113.2 | 25.5 | 2.332 |
| PDMA-795K | 127.6 | 17.1 | 2.701 |

TEM studies showed that particles formed in solution were uniform compared to the highly aggregated particles formed in the case of PDA alone (micrographs not shown). High molecular weight PDMA prevented spontaneous aggregation and cross-linking of PDA particles and the particle size decreased with increase in molecular weight of PDMA chains. Particle size obtained in the case of PDA-PDMA795K was around 130 nm. TEM images of binary particles gave a dense core surrounded with a light shell; due to the polymeric nature of the both the components, it was difficult ascertain which component constituted the shell (micrographs not shown).

Moreover, the process of self-assembly of the PDA-PDMA binary particles on the surface was studied using AFM force measurements and XPS analysis. The composition of binary particles obtained by mixing 1:5 dopamine and PDMA was similar to the original composition. However, the deposition of PDA-PDMA particles changed the composition on surface coating. For instance the surface composition of the binary coating analyzed by XPS analysis gave a closer composition to PDMA than PDA-PDMA initial composition suggesting the possibility of rearrangement of polymer chains upon particle deposition on the surface (FIG. 2A).

Figure 5B:
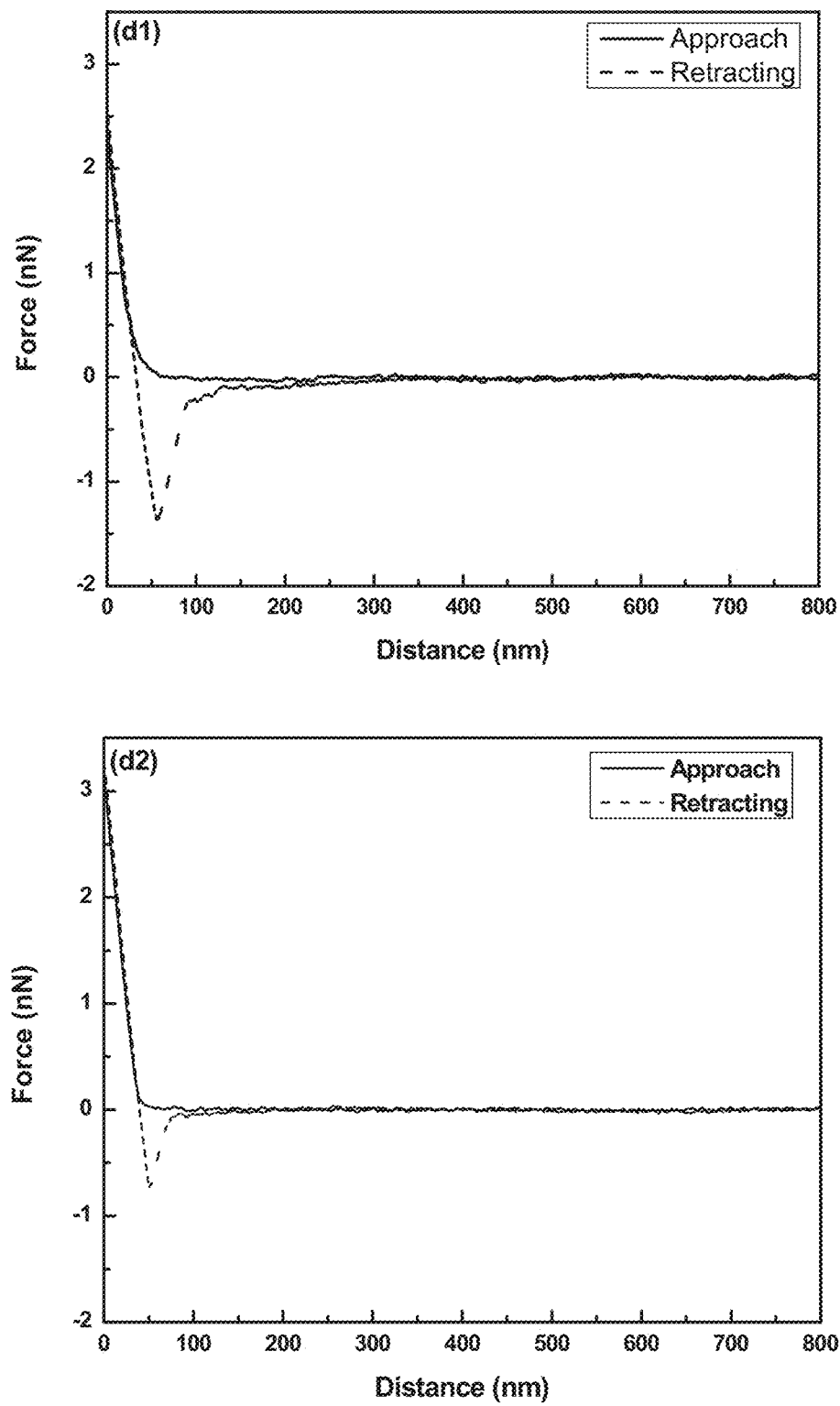
FIG. 5B shows force measurements of (d1) PDA-coated Si, (d2) PDA/PDMA-43K-coated Si, (d3) PDA/PDMA- 213K-coated Si, (d4) PDA/PDMA-795K-coated Si, wherein representative approach (solid line) and retraction (broken line) force curves are shown.
Figure 5B:
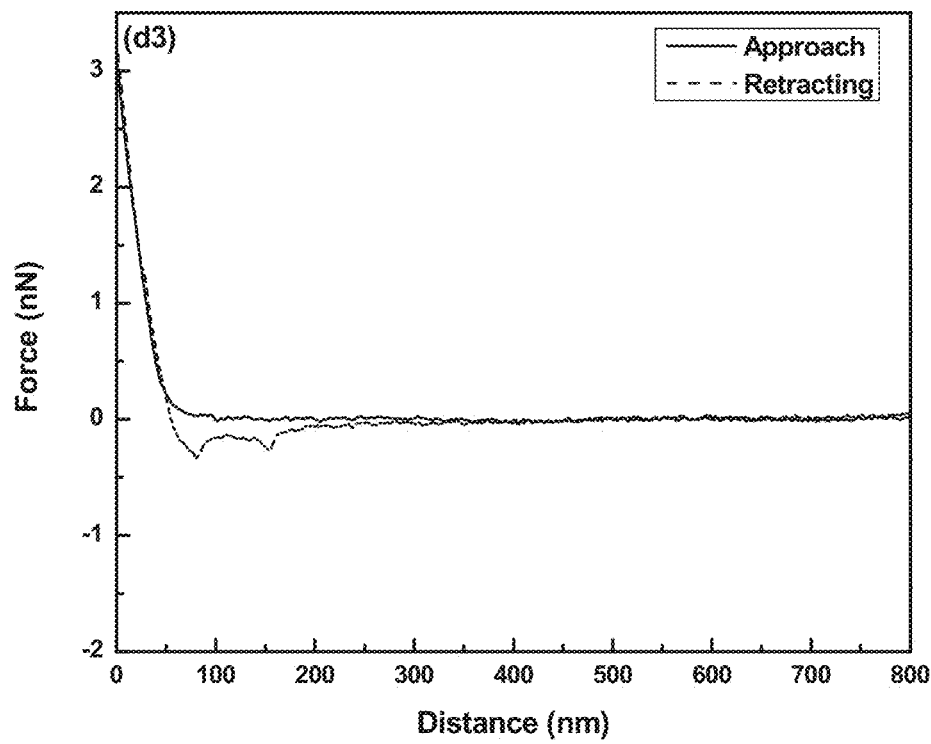
Figure 5B:
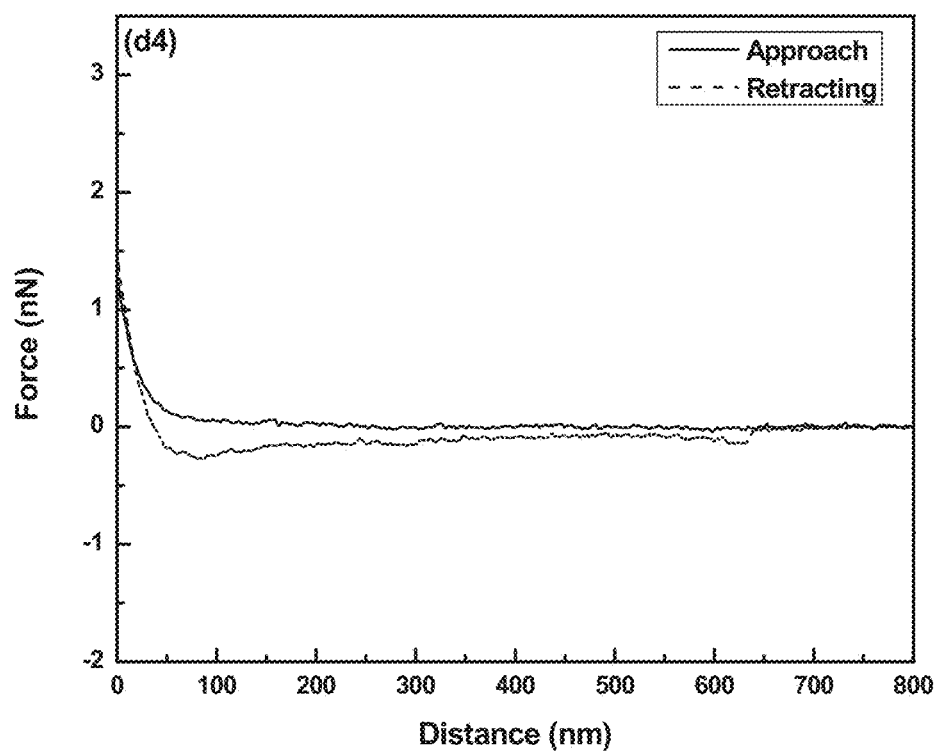
Figure 5C:
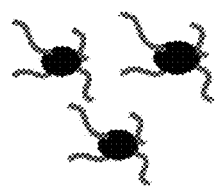
FIG. 5C shows a schematic of a possible mechanism for PDMA-795K coating formation onto substrate surface.
Figure 5C:
Figure 5C:
Figure 5D:
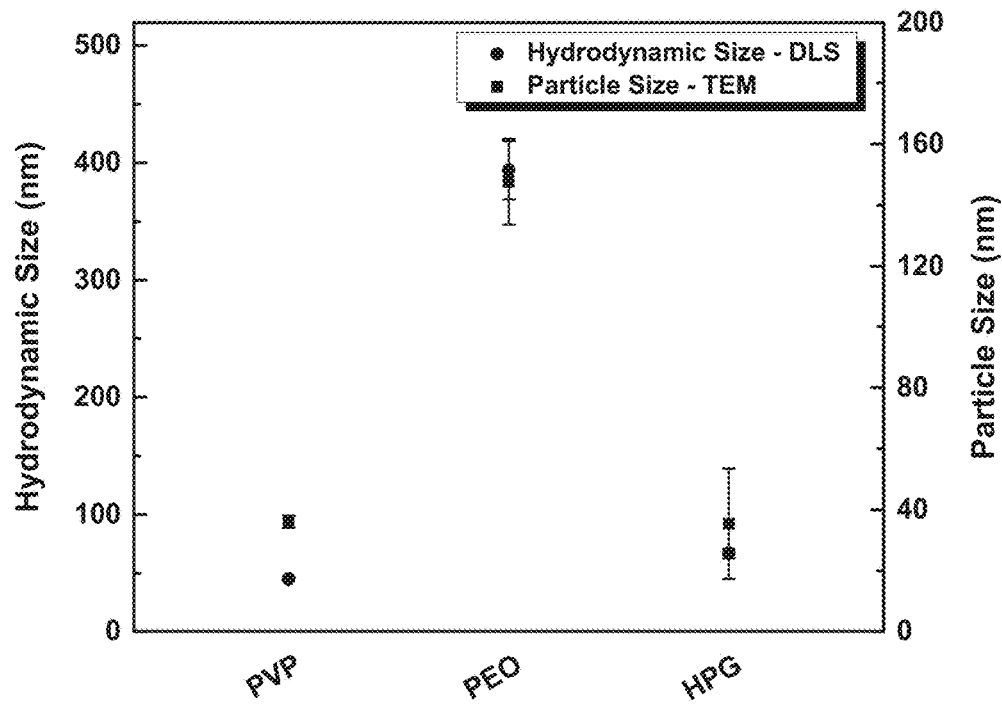
FIG. 5D shows dynamic light scattering (DLS) and TEM studies of particle formation in a TRIS buffered solution of dopamine and in a TRIS buffered solution of PDA with either PEO, PVP or HPG.
Figure 5E:
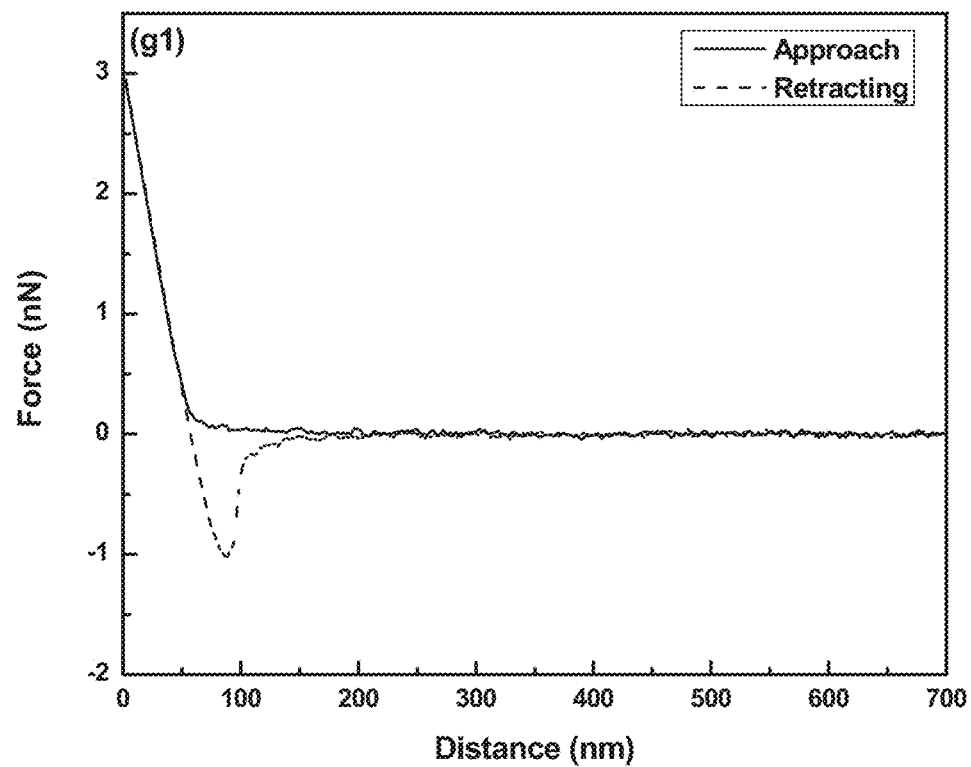
FIG. 5E shows force measurements of PDA combined with high molecular weight (g1) PVP, (g2) PEO, and (g3) HPG coated Si substrates, wherein representative approach (solid line) and retraction (broken line) force curves are shown.
Figure 5E:
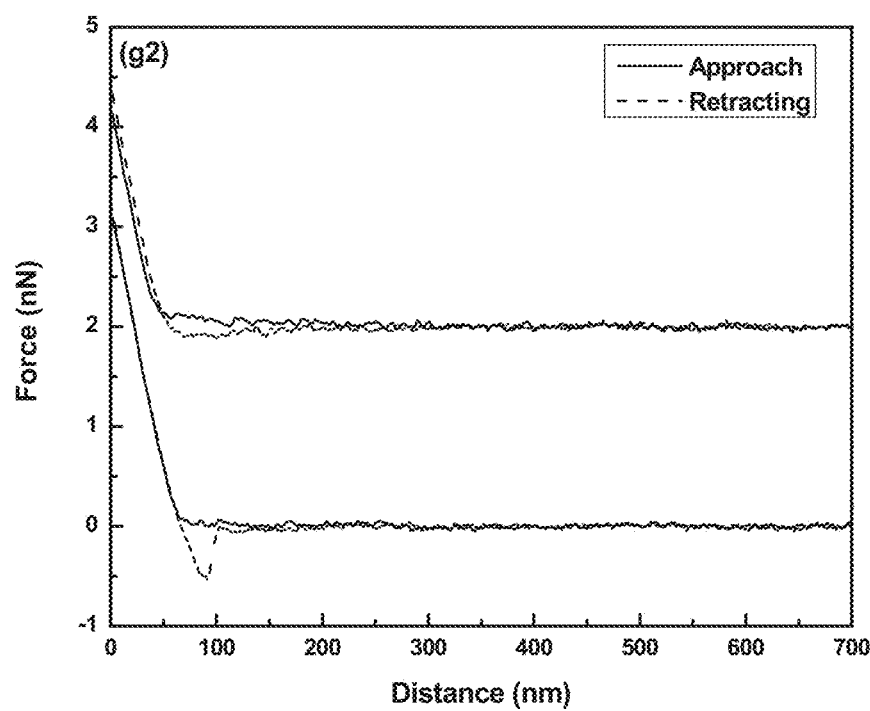
Figure 5E:
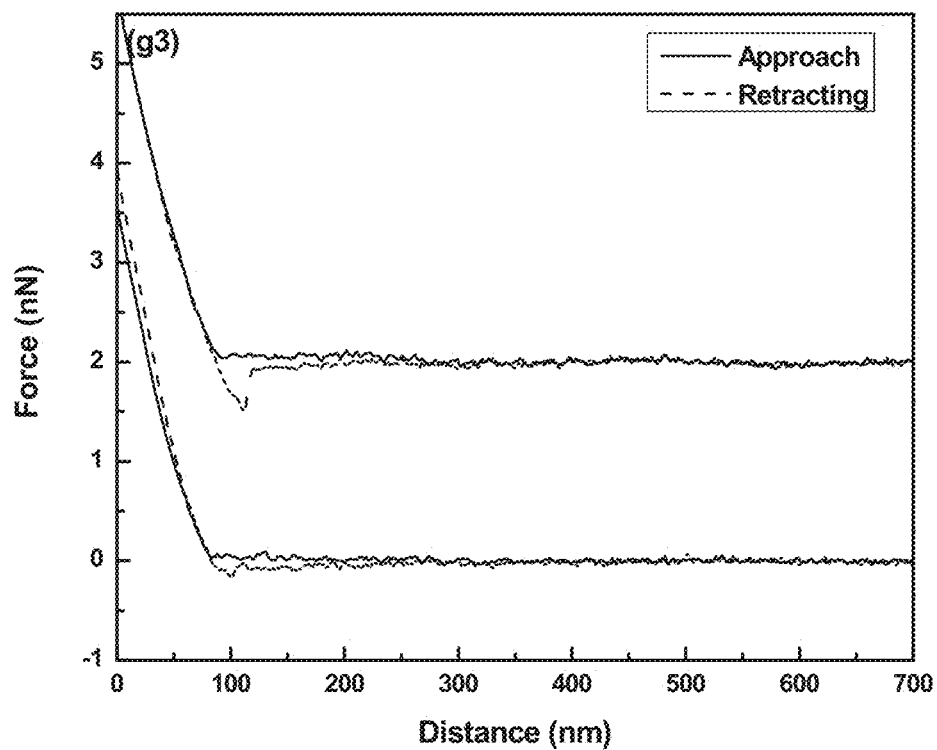

The surface structure of the binary coating was probed using AFM force measurements (see FIGS. 5B and 5E). AFM approach curves on binary coating showed typical profile for steric repulsion exerted by the polymer grafts on surface. Equilibrium thickness increased with increase in the molecular weight of the PDMA chains. Retraction curve on binary coating gave characteristic profile for loop-like assembly of the PDMA chains on the surface and the extension length increased with increase in molecular weight of PDMA.

Figure 9B:
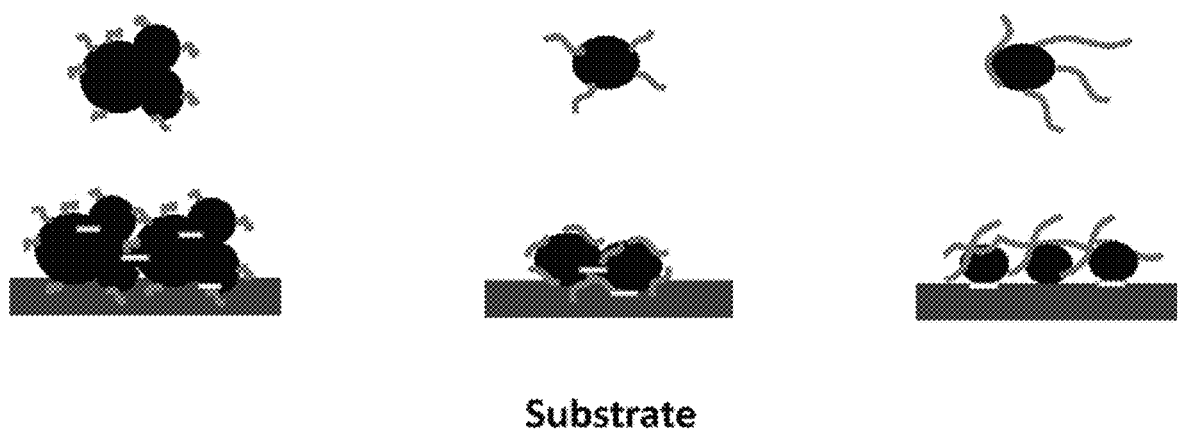
FIG. 9B shows an illustration of a possible mechanism of coating formation onto surface using different molecular weight PDA/PDMA.
Figure 9C:
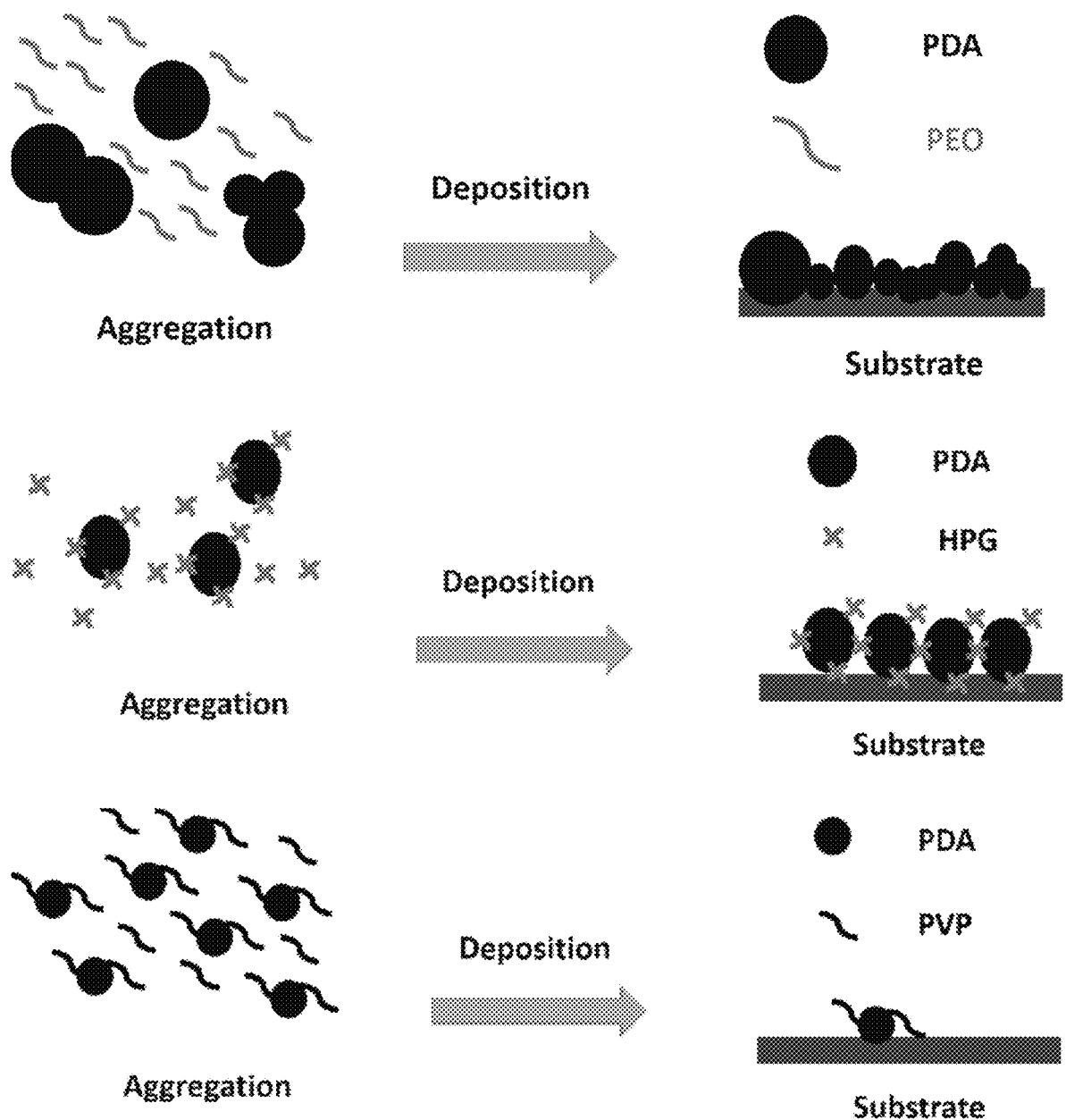
FIG. 9C shows an illustration of possible mechanism of coating formation onto a substrate surface using PDA and different high molecular weight hydrophilic polymers.

Based on these observations, a mechanism was proposed for the formation of a stable binary coating (FIG. 5C) which influences the self-assembly of PDA polymerization. The mechanism involves series of processes including (1) formation of uniform particles composed of hydrophilic polymer and PDA through possible hydrogen bonding and hydrophobic-hydrophobic interactions, (2) deposition of particles on the surface which influences the structure and thickness of the coating layer, (3) rearrangement of deposited PDA-PDMA particles on the surface by the rearrangement of polymer chains on the surface to from a PDMA enriched surface and (4) the formation of stable cross-linked binary coating on the surface anchored by PDA on the surface and PDMA preferentially enriched on the surface. Compare to proposed mechanisms for 43K, 213K and 795K PDMA (FIG. 9B) and for PEO and HPG (FIG. 9C).

Example 5: Adaptation of the Technology for Catheter Modification

Figure 6A:
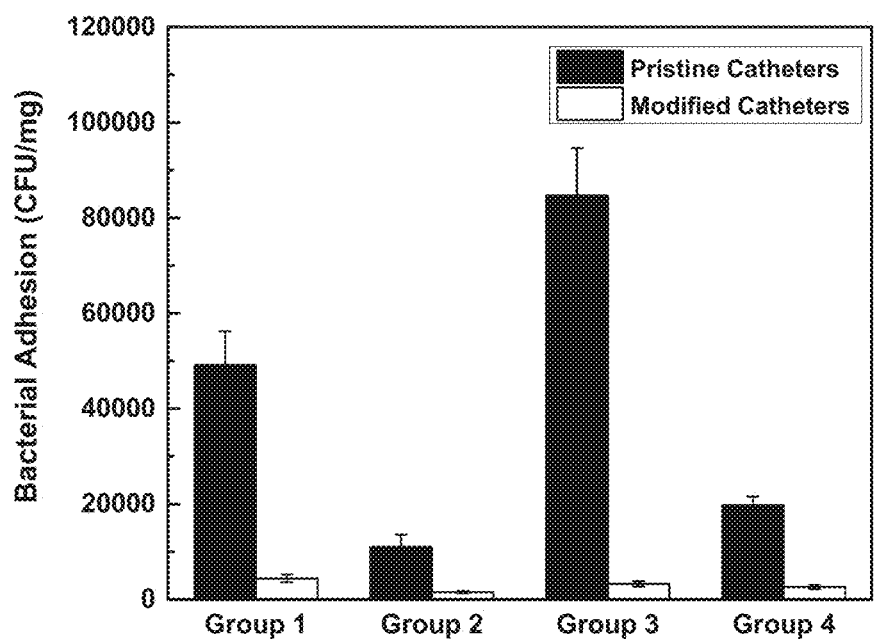
FIG. 6A shows adherence of S. aureus to uncoated (pristine) and PDA/PDMA-795K coated catheters (modified), wherein adherence was assessed by the CFU method, wherein each group contains one uncoated and one coated catheter and 4 uncoated and 4 coated catheters for in vitro experiment.
Figure 6B:
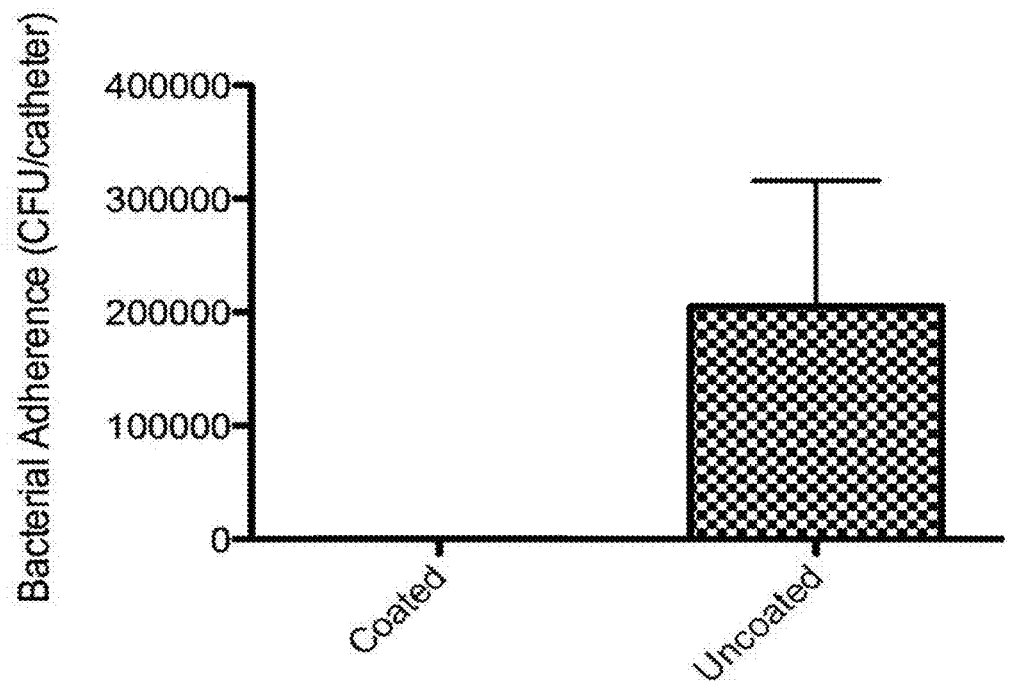
FIG. 6B shows in vivo adherence of S. aureus to uncoated and PDA/PDMA-795K coated catheters tested in a mouse model of Catheter-associated urinary tract infection (CAUTI), to compare adherent bacteria and biofilm formation on the catheter surface when challenged with 500,000 CFU/mL S. aureus bacteria over 7 days.

Given the ability of the PDMA coating to prevent surface bacterial adhesion and biofilm formation, the surface-coating method was adapted to prevent bacteria adhesion and subsequent biofilm formation on urinary catheters. Biofilm formation on the urinary catheter increases the risk of sepsis in patients with indwelling catheters. Uncoated (pristine) and coated (modified) catheters were exposed to $1\times10^6$ cells/ml of S. aureus in LB medium for 6 h. Determination of the number of bacteria adhere on the surface of PDMA coated samples showed a 86.3% to 96.1% reduction compared to unmodified catheters (FIG. 6). Each group contains one uncoated and one coated catheter, whereby 4 uncoated and 4 coated catheters for in vitro experiment were used.

Figure 6C:
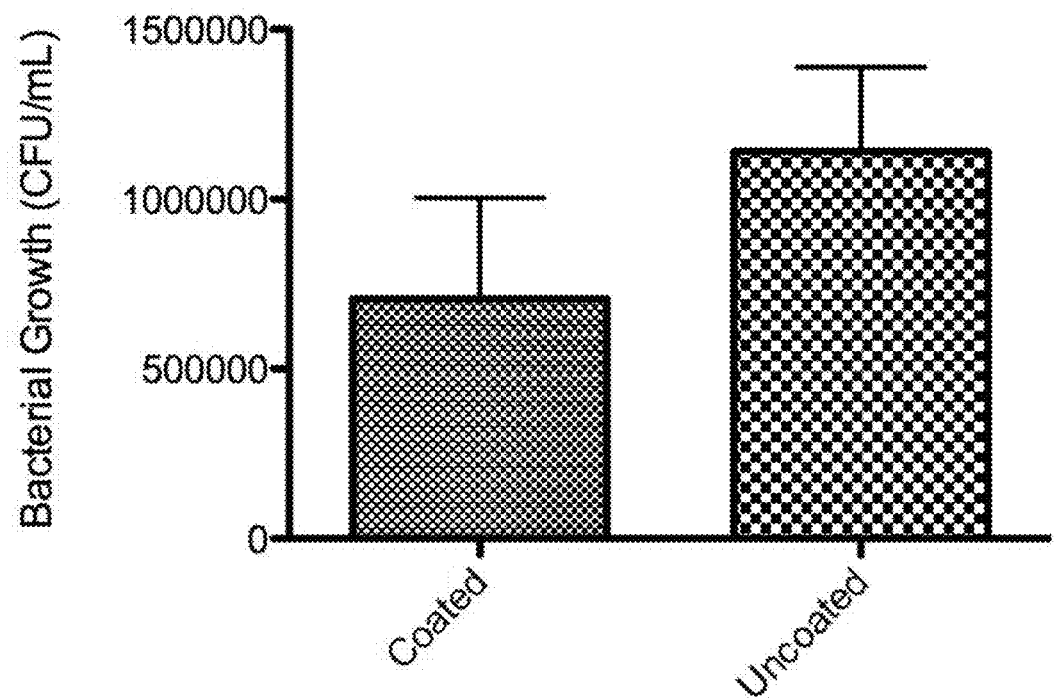
FIG. 6C shows the bacterial growth in mouse urine taken from the CAUTI mice in FIG. 6B, to compare bacterial growth (CFU/mL) in the urine after 7 days.

In vivo experiments were also conducted, wherein coated and uncoated catheters (substrates) were produced for testing in a mouse model of Catheter-associated urinary tract infection (CAUTI), to compare adherent bacteria and biofilm formation on the catheter surface when challenged with $10^8$ CFU/mL S. aureus bacteria over 7 days. Catheters were placed in a buffer solution containing dopamine and ultra-high molecular weight hydrophilic synthetic polymers (PDMA-795K (10 mg/ml)). Bacterial adhesion in vivo of the anti-biofilm coated catheters was tested using a mouse model of CAUTI, dramatically reducing (99.7%) adherent bacteria and biofilm formation on the catheter surface compared to uncoated catheters when challenged with $10^8$ CFU/mL bacteria over 7 days (FIG. 6B) and also surprisingly showed a reduction of bacterial growth within the urine (FIG. 6C).

Example 6: Studies to Distinguish Low Molecular Weight and High Molecular Weight PDA/PDMA Coatings Synthesis of Coating:
Seven PDMA/PDA coatings were prepared with PDMA 43K (coatings 2 and 3), 213 K (coatings 4 and 5) and 795K (coatings 6 and 7). The synthesis process is similar to previous experiments, however, some differences are in terms of the ratio between PDMA and PDA used. The ratio of PDMA/PDA is changed from 5:1 to 15:1 (wt/wt) to understand whether the composition change in the initial coating solution was influencing the physico-chemical properties and biofilm formation.

TABLE 4

Experimental details and characteristics of PDA/PDMA coatings

| Sample ID | PDMA (Mn) & Conc. | Dopamine | Ratio of PDMA/PDA | #Thickness (Si) | $Thickness (Ti) | @Particle Size |
|---|---|---|---|---|---|---|
| Coating 1 | | 2 mg/ml | | 33.2 nm | 22.4 nm | 3000 nm |
| Coating 2 | 43K; 10 mg/ml | 2 mg/ml | 5:1 | 60.8 nm | 57.9 nm | 744 nm |
| Coating 3 | 43K; 30 mg/ml | 2 mg/ml | 15:1 | 20.4 nm | 16.6 nm | 335 nm |
| Coating 4 | 213K, 10 mg/ml | 2 mg/ml | 5:1 | 19.1 nm | 17.1 nm | 341 nm |
| Coating 5 | 213K, 30 mg/ml | 2 mg/ml | 15:1 | 13.5 nm | 15.8 nm | 387 nm |
| Coating 6 | 795K, 10 mg/ml | 2 mg/ml | 5:1 | 18.4 nm | 15.5 nm | 418 nm |
| Coating 7 | 795K, 30 mg/ml | 2 mg/ml | 15:1 | 20.9 nm | 14.2 nm | 511 nm | thickness of the coating is measured by ellipsometry analysis on silicon wafer
$thickness of the coating is measured by ellipsometry analysis on Ti surface.
@particle size (hydrodynamic size) is measured by dynamic light scattering.

Scanning electron microscopy (SEM) analysis was performed to determine the morphology of the coatings prepared at different conditions. The coatings were scanned under both dry and wet conditions (aqueous).

Morphology of the coating depends on the molecular weight of the PDMA. Only high MW PDMA gave uniform coating. Even at higher ratio of low MW PDMA (15:1) uniform morphology was not observed. Uniform coating is needed to generate low fouling surfaces (micrographs not shown).

Similarly, surface roughness was evaluated by AFM morphology analysis. Usually, a smooth surface gives better antifouling performance. Only high molecular weight PDMA along with PDA generated smooth surfaces possibly due to the differences in aggregation of PDA in presence of PDMA. Unlike low MW PDMA (43K), High MW PDMA (213K and 795K) stabilized the particles which generated smooth deposition process (micrographs not shown). Micrographs taken at the same resolution show considerable surface irregularities for PDA alone and PDA/PDMA-43K coated substrates, while PDA/PDMA-213K and PDA/PDMA-795K coated substrates showed almost completely uniform smooth surfaces at the same resolution.

Surface Chemistry by XPS Analysis (Substrate: Si)
Surface compositions of the different coatings set out in TABLE 4 were compared. The nitrogen content increased with increasing polymer MW as well as composition suggesting that more PDMA is accumulated on the surface. Nitrogen content >10 At % (N/C ratio is >0.150) is only achieved for high MW PDMA based coating. The data suggests that there is an enrichment of high MW polymer on the surface compared to the low MW polymer which produced the best anti-fouling performance.

TABLE 5

Comparison of chemical compositions of various deposited coatings on silicon wafers based on X-ray Photoelectron Spectroscopy (XPS) Analysis.

| Sample | C | N | O | Si | N/C |
|---|---|---|---|---|---|
| Coating 1 | 59.28 | 6.38 | 30.96 | 3.38 | 0.108 |
| Coating 2 | 71.40 | 8.10 | 20.20 | 0.30 | 0.113 |
| Coating 3 | 71.43 | 9.34 | 23.62 | 1.83 | 0.132 |
| Coating 4 | 69.02 | 9.55 | 21.12 | 0.31 | 0.138 |
| Coating 5 | 55.42 | 8.32 | 23.84 | 12.42 | 0.150 |

TABLE 5-continued

Comparison of chemical compositions of various deposited coatings on silicon wafers based on X-ray Photoelectron Spectroscopy (XPS) Analysis.

| Sample | C | N | O | Si | N/C |
|---|---|---|---|---|---|
| Coating 6 | 71.67 | 10.67 | 17.21 | 0.45 | 0.150 |
| Coating 7 | 70.54 | 11.78 | 17.13 | 0.55 | 0.167 |

Coating 5: Low N content is due to the thinner layer formed (see section 1).

AFM Force Curve Analysis

AFM force curve analysis was performed on different coatings and the data are summarized below. Coatings prepared on Si wafer are used for the analysis under aqueous conditions. The goal of the experiment was to determine whether increasing the concentration of PDMA in the coating could alter the short range hydrophobic attractive forces and force curves.

Figure 9D:
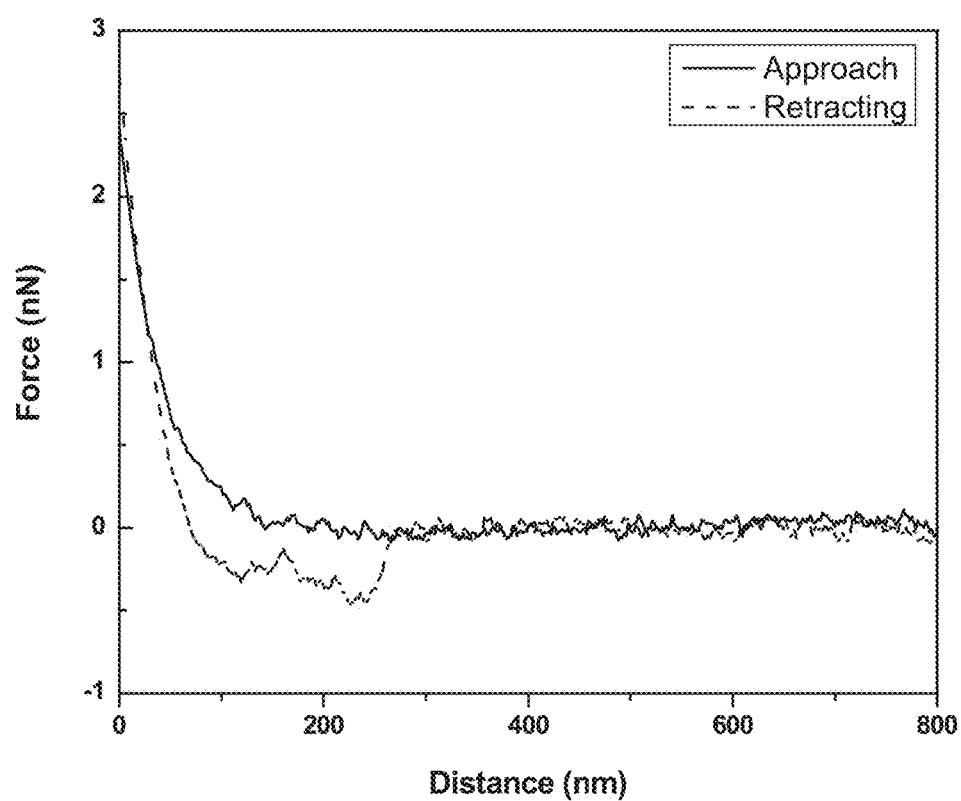
FIG. 9D shows force measurements of coating 3, 43K: 30 mg/ml PDMA 2 mg/ml PDA, wherein representative approach (solid line) and retraction (broken line) force curves are shown.
Figure 9E:
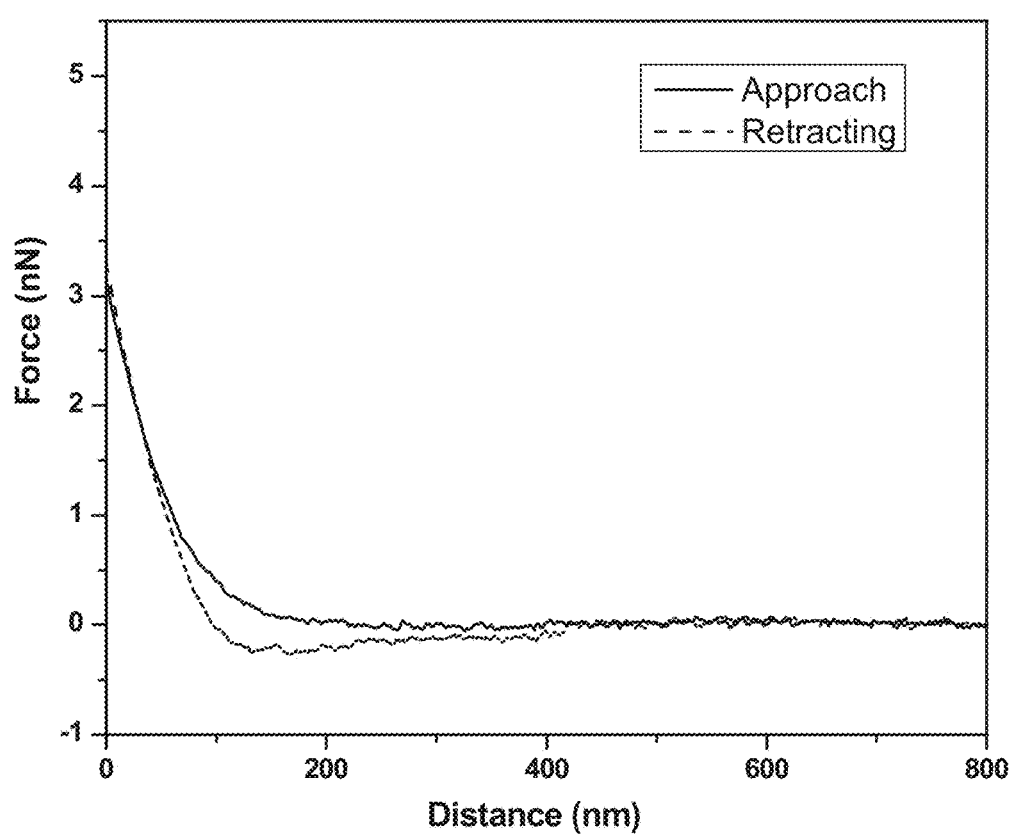
FIG. 9E shows force measurements of coating 5, 213K: 3 mg/ml PDMA; 2 mg/ml PDA, wherein representative approach (solid line) and retraction (broken line) force curves are shown.
Figure 9F:
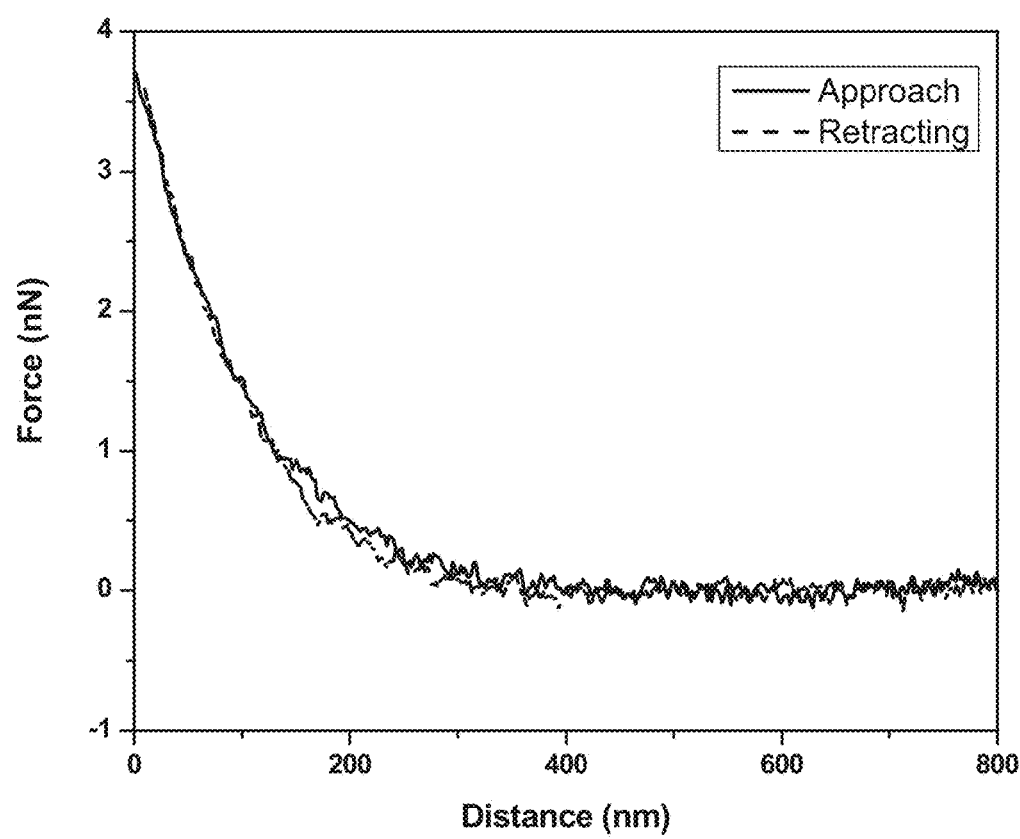
FIG. 9F shows force measurements of coating 7,795K: 30 mg/ml PDMA; 2 mg/ml PDA, wherein representative approach (solid line) and retraction (broken line) force curves are shown.
Figure 10A:
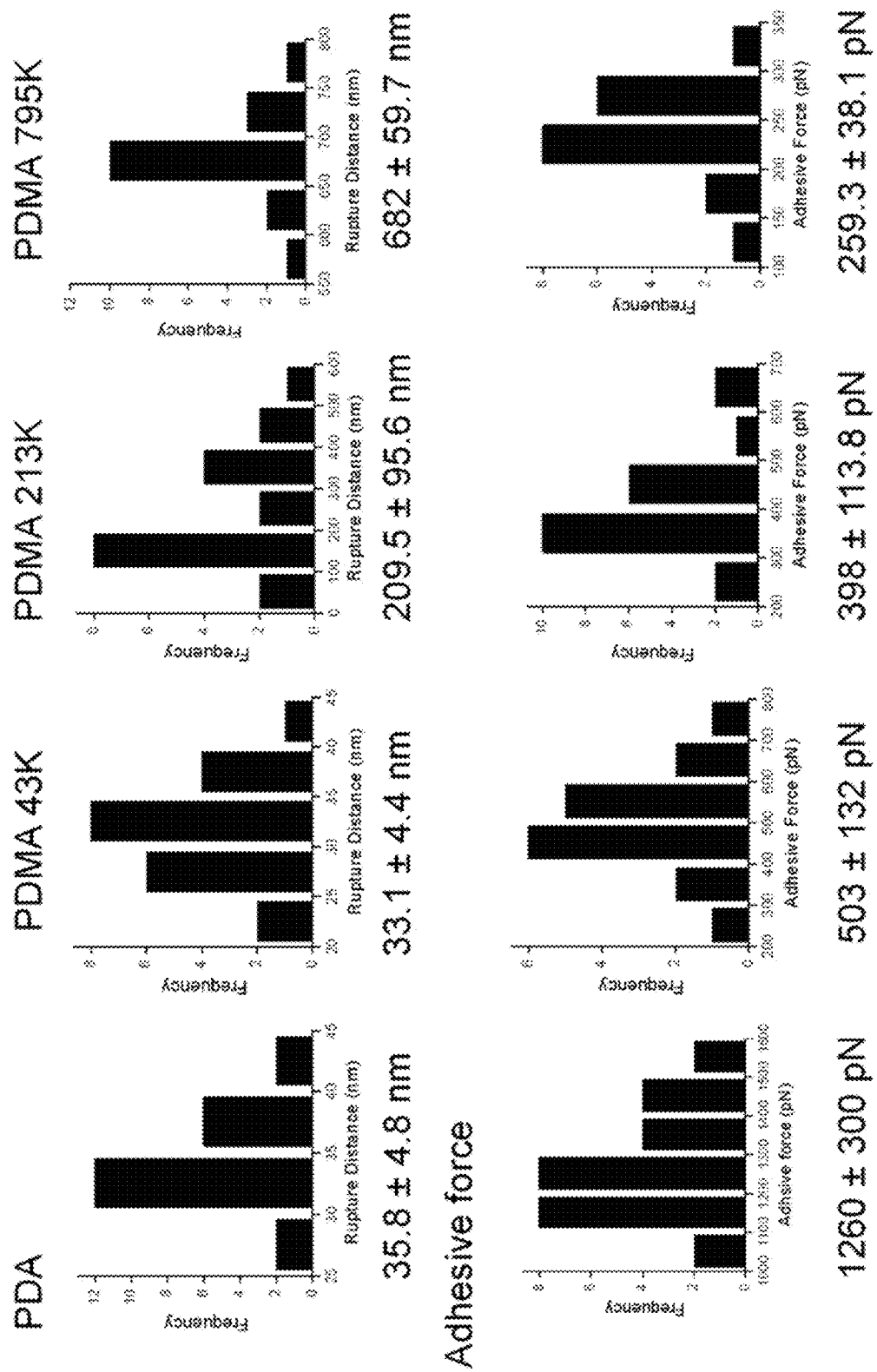
FIG. 10A shows a series of histograms representing the rupture distance and adhesive force calculated from the force curves for PDA-coating, PDA/PDMA-43K-coating, PDA/PDMA-213K-coating, PDA/PDMA-795K-coating with a mix ratio of PDMA and PDA about 5:1 (10 mg/mL PDMA, 2 mg/mL PDA).
Figure 10B:
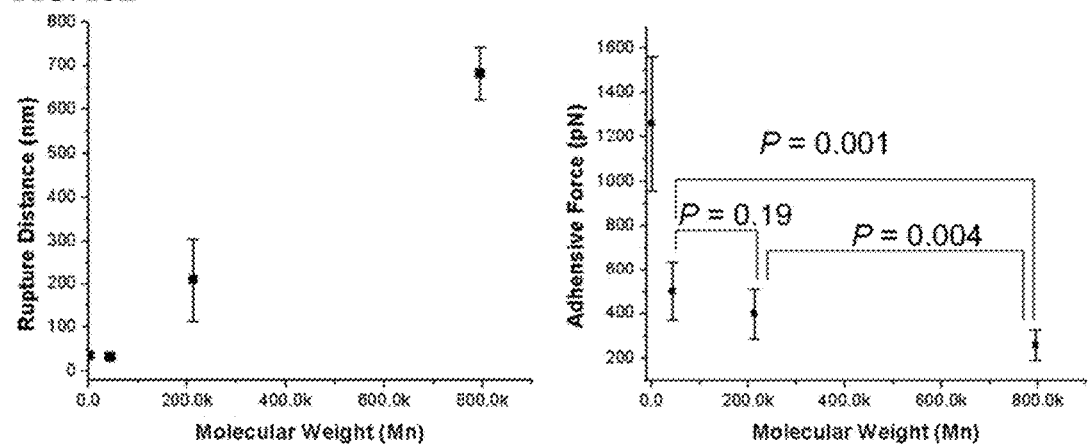
FIG. 10B shows two plots of dependence of rupture distance and adhesive force on the molecular weight of PDMA used in the coating with a mix ratio of PDMA and PDA about 5:1 (10 mg/mL PDMA, 2 mg/mL PDA).
Figure 10C:
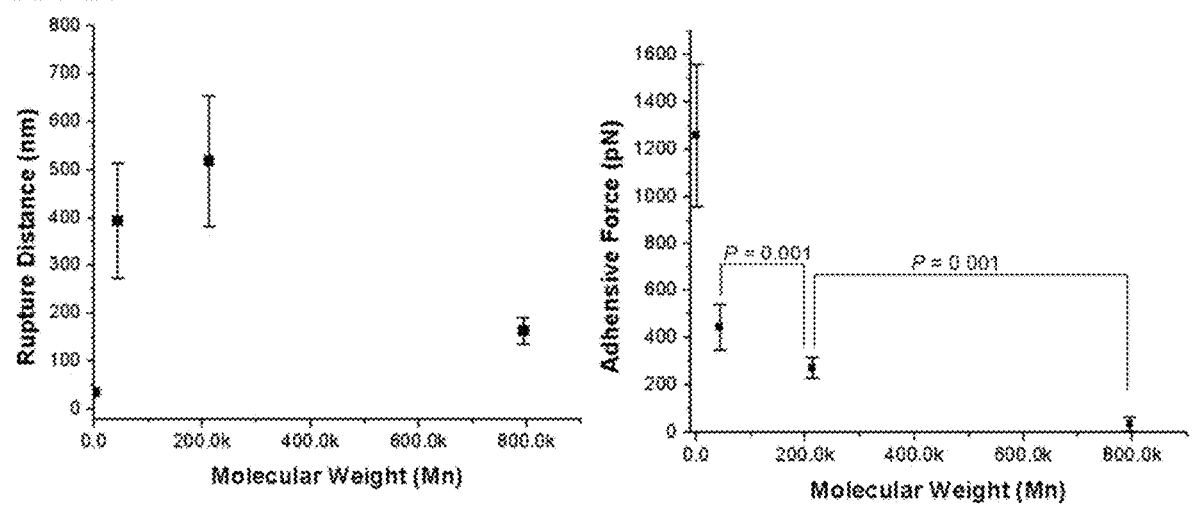
FIG. 10C shows two plots of dependence of rupture distance and adhesive force on the molecular weight of PDMA used in the coating with a mix ratio of PDMA and PDA about 15:1 (30 mg/mL PDMA, 2 mg/mL PDA).
Figure 10D:
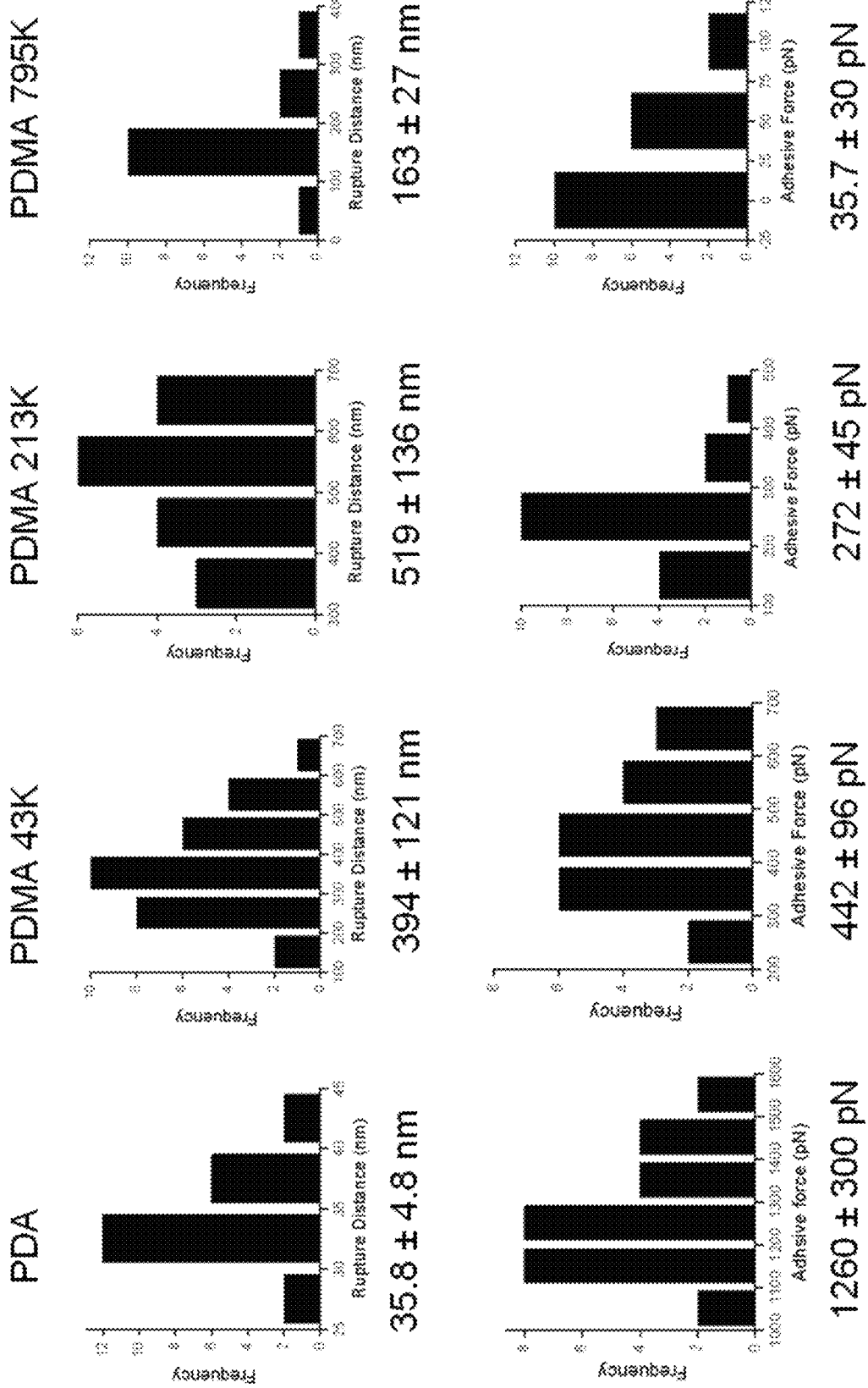
FIG. 10D shows a series of histograms representing the rupture distance and adhesive force calculated from the force curves for PDA-coating, PDA/PDMA-43K-coating, PDA/PDMA-213K-coating, PDA/PDMA-795K-coating with a mix ratio of PDMA and PDA about 15:1 (30 mg/mL PDMA, 2 mg/mL PDA).

FIGS. 9D, 9E and 9F show AFM force measurements of PDA/PDMA (43K, 213K and 795K, respectively) coatings containing PDA/PDMA at 1:15 ratio (details given in TABLE 4), wherein the high MW PDMA coating has distinct force profile (approach and retract compared to low MW PDMA coating). 795K shows almost no difference in the approach and retraction forces, but 213K and 43K show marked differences, which increase as the molecular weight decreases. The AFM force curves and analyses (FIG. 10A-D) clearly confirm that the structure of the coating prepared by low MW and high MW PDMA is different. Hydrophobic interactions between the AFM tip and the coating illustrate that only high MW PDMA are able to prevent short range interactions. In addition, the shape of force curves are different for low MW and high MW polymer coatings, which suggests that the organization of PDMA on the surface of coating is different. In the case of low MW PDMA/PDA coating, increase in the ratio of PDMA/PDA is not sufficient to prevent the hydrophobic short range interactions. High MW PDMA/PDA coating effectively reduces such interactions. This confirms that difference the physical properties of the coating are due to the MW of the PDMA and not due to the concentration. Only high MW polymer is able to provide an optimal structure which significantly reduces short range hydrophobic forces. The reduction in hydrophobic interaction is correlated well with the early stage biofilm adhesion.

The Influence of MW and Composition PDMA in the PDMA/PDA Coating on Early Stage of Biofilm Formation.

Coatings prepared on titanium oxide surface were used for this analysis of S. aureus lux strain on biofilm formation after 24 h. Initial bacterial concentration was 106 CFU/mL in LB media. After 24 h of incubation, CFU counts and fluorescent images are taken (micrographs not shown). Images and CFU data are analyzed using the following criteria. CFU/Image=0 equal to Adhesion Score=0; CFU/Image=1-10 equal to Adhesion Score=1; CFU/Image=10-100 equal to Adhesion Score=2; CFU/Image=100-1000 equal to Adhesion Score=3; CFU/Image>1000 equal to Adhesion Score=4.

Coating 1 had an average Score of 3.25 (Adhered Bacteria/Image around 500-1000). Coating 2 had an average Score of 3.00 (Adhered Bacteria/Image around 500-1000). Coating 3 had an average Score of 2.75 (Adhered Bacteria/Image around 500). Coating 4 had an average Score of 2.5 (Adhered Bacteria/Image around 200). Coating 5 had an average Score of 1.75 (Adhered Bacteria/Image=44). Coating 6 had an average Score of 1.25 (Adhered Bacteria/Image=13). Coating 7 had an average Score of 1.25 (Adhered Bacteria/Image=22)

There was a reduction in bacterial adhesion with PDMA/PDA coating in comparison to control surface. There was reduced bacterial adhesion as MW of the coating increased. However, irrespective of the composition of the low MW PDMA used, the coating prepared from low MW PDMA (coatings 2 & 3) were not as effective at resisting bacterial adhesion. High MW PDMA coating effectively prevented bacterial adhesion.

Figure 11:
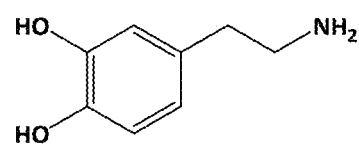
FIG. 11 shows the chemical structures of polymeric binder monomers tested herein for substrate coating (i.e. DA: Dopamine; NE: Norepinephrine; TA: Tannic acid; PG: Pyrogallol).
Figure 11:
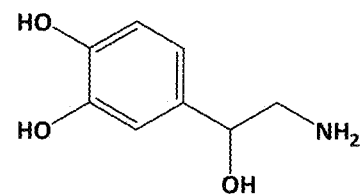
Figure 11:
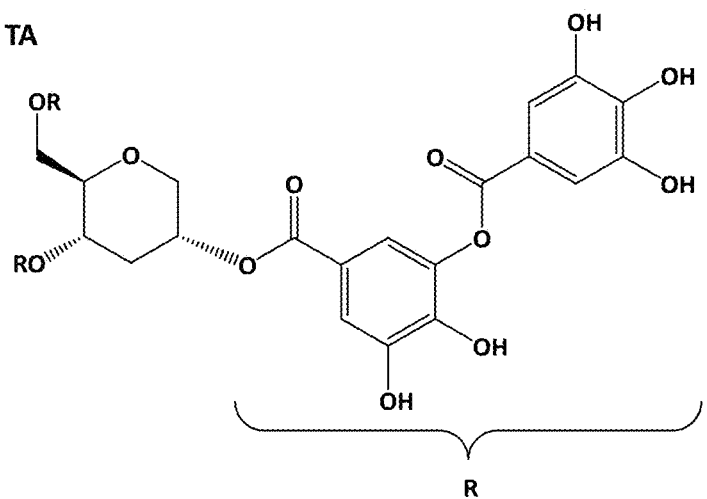
Figure 11:
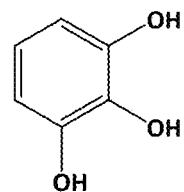

Example 7: Comparison of Alternative Polymeric Binders for Use with High Molecular Weight PDMA Coatings Catechol (2 mg/ml) and polydimethylacrylamde (795K) (PDMA-795K (10 mg/ml)) were mixed together in aqueous buffer and coating was applied via a simple dip coating process for 24 h at room temperature without stirring. 10 mM Tris buffer (pH=8.5) was used when DA or NE (see FIG. 11) was used for coating precursor. 10 mM Tris buffer with 0.6M NaCl (Ph=7.5) was used when TA or PG (see FIG. 11) was used for coating precursor. Titanium surface (Ti) was used as the substrate for coating.

TABLE 6

Characterization of the coatings generated by different catechols.

| Sample | PDMA (mg/mL) | Catechol | $Particle Size | &Thickness | STDEV |
|---|---|---|---|---|---|
| Ti-1 | 0 | DA | 3264.1 nm | 18.8 nm | 1.1 nm |
| Ti-2 | 10 | DA | 370.7 nm | 16.7 nm | 3.7 nm |
| Ti-3 | 0 | NE | 617.8 nm | 36.3 nm | 1.3 nm |
| Ti-4 | 10 | NE | 334.9 nm | 13.7 nm | 1.6 nm |
| Ti-5 | 0 | TA | 1652.9 nm | 25.3 nm | 1.5 nm |
| Ti-6 | 10 | TA | 153.2 nm | 16.2 nm | 3.3 nm |
| Ti-7 | 0 | PG | 4121.2 nm | 7.0 nm | 0.3 nm |
| Ti-8 | 10 | PG | 270.1 nm | 4.1 nm | 0.1 nm |

$particle size of PDMA (795K)/Catechol binary complex measured by dynamic light scattering.
&thickness of the coating on Ti-surface measured by ellipsometry measurements.

Selected polymeric binders were used to generate uniform binary coating on Ti-surface. Fluorescence microscopy images of S. aureus adhesion on uncoated $TiO_2$; PDA/PDMA-795K coated $TiO_2$; PNE/PDMA-795K coated $TiO_2$; PTA/PDMA-795K coated $TiO_2$; PPG/PDMA-795K coated $TiO_2$ were compared after 24 h incubation in LB medium with an initial concentration at $10^6$ cells/ml. All the coatings were effective in preventing short-term biofilm formation by S. aureus (data not shown). The fluorescence level on the coated surface after bacterial adhesion was similar to the background.

PDA/PDMA (795K) coating of a Ti surface was placed in S. aureus suspension for 3 and 7 days to determin the prevention of long-term biofilm formation. The biofilm formation was investigated using confocal microscopy after live-dead staining. Confocal fluorescence microscopy images of S. aureus adhesion on uncoated TiO2; were compared with PDA/PDMA-795K coated TiO2 after 72 h incubation in TSB medium with an initial concentration at $5 \times 10^4$ cells/ml. Medium was changed every 24 hours with a fresh addition of bacteria.

The PDA/PDMA (795 k) coating was highly effective in preventing biofilm in enriched media (data not shown). Similar data for 7-day biofilm inhibition has also been observed (data not shown).

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention. The invention includes all embodiments and variations substantially as hereinbefore described and with reference to the examples and drawings.

REFERENCES

Antoni, P.; Nyström, D.; Pietrzak, K.; Vincent, L. (Carmeda A B, Sweden; W. L. Gore & Assoc., USA). Coating For a Substrate. PCT Appl. WO 2014/118382 A1. Aug. 7, 2014.

Carcia-Fernandez, L.; Cui, J.; Serrano, C.; Shafiq, Z.; Gropeanu, R. A.; Miguel, V. S.; Ramos, J. I.; Wang, M.; Auernhammer, G. K.; Ritz, S.; Golriz, A. A.; Berger, R.; Wagner, M.; del Campo, A. *Adv. Mat.* 2013, 25, 529-533.

Chuan, Y.; Ding, X.; Ono, R. J.; Lee, H.; Hsu, L. Y.; Tong, Y. W.; Hedrick, J.; Yang, Y. Y. *Adv. Mater.* 2014, 26, 7346-7351.

Dalsin, J. L.; Hu, B.-H.; Lee, B. P.; Messersmith, P. B. *J. Am. Soc. Chem.* 2003, 125, 4253-4258.

Dang, Y.; Xing, C.-M.; Quan, M.; Wang, Y.-B.; Zhang, S.-P.; Shi, S.-Q.; Gong, Y.-K. *J. Mater. Chem. B* 2015, 3, 4181-4190.

Dang, Y.; Quan, M.; Xing, C.-M.; Wang, Y.-B.; Gong, Y.-K. *J. Mater. Chem. B* 2015, 3, 2350-2361.

Ding, X.; Yang, C.; Lim, T. P.; Hsu, L. Y.; Engler, A. C.; Hedrick, J. L.; Yang, Y.-Y. *Biomat.* 2012, 33, 6569-6603.

Dreyer, D. R.; Miller, D. J.; Freeman, B. D.; Paul, D. R.; Bielawski, C. W. *Chem. Sci.* 2013, 4, 3796-3802.

Du, X.; Li, L.; Li, J.; Yang, C.; Frenkel, N.; Welle, A.; Heissler, S.; Nefedov, A.; Grunze, M.; Levkin, P. A. *Adv. Mater.* 2014, 26, 8029-8033.

Ejima, H.; Richardson, J. J.; Liang, K.; Best, J. P.; van Koeverden, M. P.; Such, G. K.; Cui, J.; Caruso, F. *Science* 2013, 341, 154-157.

Ham, H. O.; Park, S. H.; Kurutz, J. W.; Szleifer, I. G.; Messersmith, P. B. *J. Am. Chem. Soc.* 2013, 135, 13015-13022.

Hong, S.; Na, Y. S.; Choi, S.; Song, I. T.; Kim, W. Y.; Lee, H. *Adv. Funct. Mater.* 2012, 22, 4711-4717.

Kang, S. M.; Hwang, N. S.; Yeom, J.; Park, S. Y.; Messersmith, P. B.; Choi, I. S.; Langer, R.; Anderson, D. G.; Lee, H. *Adv. Funct. Mater.* 2012, 22, 2949-2955.

Kim, K.; Shin, M.; Koh, M. Y.; Ryu, J. H.; Lee, M. S.; Hong, S.; Lee, H. *Adv. Funct. Mater.* 2015, DOI: 10.1002/adfm.201500034.

Lau, K. H. A.; Sileika, T. S.; Park, S. H.; Sousa, A. M. L.; Burch, P.; Szleifer, I; Messersmith, P. B. *Adv. Mater. Interfaces* 2015, 2, 1400225.

Lee, H.; Dellatore, S. M.; Miller, W. M.; Messersmith, P. B. *Science* 2007, 318, 426-430.

Lee, H.; Lee, Y.; Statz, A. R.; Rho, J.; Park, T. G.; Messersmith, P. B. *Adv. Mater.* 2008, 20, 1619-1623.

Lee, H.; Scherer, N. F.; Messersmith, P. B. *Science* 2006, 103, 12999-13003.

Li, L.; Yan, B.; Yang, J.; Chen, L.; Zeng, H. *Adv. Mater.* 2014, 27, 1294-1299.

Lynge, M. E.; van der Westen, R.; Postma, A.; Städler, B. *Nanoscale*, 2011, 3, 4916-4928.

Messersmith, P. B.; Lee, H. H. L.; Lee, B. P. (USA). Biomimetic Modular Adhesive Complex: Materials, Methods and Applications Therefore. U.S. Pat. No. 8,563,117 B2. Oct. 22, 2013.

Miller, D. J.; Araujo, P. A.; Correia, P. B.; Ramsey, M. M.; Kruithof, J. C.; van Loosdrecht, M. C. M.; Freeman, B. D.; Paul, D. R.; Whiteley, M.; Vrouwenvelder, J. S. *Water Res.* 2012, 46, 3737-3753.

Park, J. Y.; Yeom, J.; Kim, J. S.; Lee, M.; Lee, H.; Nam, Y. S. *Macromol. Biosci.* 2013, 13, 1511-1519.

Pop-Georgievski, O; Popelka, S.; Houska, M.; Chvostova, D.; Proks, V.; Rypacek, F. *Biomacromol.* 2011, 12, 3232-3242.

Ryu, J. H.; Jo, S.; Koh, M. Y.; Lee, H. *Adv. Funct. Mater.* 2014, 24, 7709-7716.

Sauer, K.; Rickard, A. H.; Davies, D. G. Microbe 2007, 2, 347-353.

Sileika, T. S.; Barrett, D. G.; Zhang, R.; Lau, K. H. A.; Messersmith, P. B. *Angew. Chem. Int. Ed.* 2013, 52, 10766-10770.

Sileika, T. S.; Kim, H.-D.; Maniak, P.; Messersmith, P. B. *Appl. Mater. Interfaces* 2011, 3, 4602-4610.

Sundaram, H. S.; Han, X.; Nowinski, A. K.; Brault, N. D.; Li, Y.; Ella-Menye, J. R.; Amoaka, K. A.; Cook, K. E.; Marek, P.; Senecal, K.; Jiang, S. Y. *Adv. Mater. Interface* 2014, 1, 140071.

Vecchia, N. F. D.; Avolio, R.; Alfe, M.; Errico, M. E.; Napolitano, A.; d'Ischia, M. *Adv. Funct. Mater.* 2013, 23, 1331-1340.

Waite, J. H.; Andersen, N. H.; Jewhurst, S.; Sun, C. *J. Adhes.* 2005, 81, 297-317.

Wei, Q.; Achazi, K.; Liebe, H.; Schulz, A.; Noeske, P. L. M.; Grunwald, I.; Haag, R. *Angew. Chem. Int. Ed.* 2014, 53, 11650-11655.

Wei, Q.; Becherer, T.; Noeske, P. L. M.; Grunwald, I.; Haag, R. *Adv. Mater.* 2014, 26, 2688-2693.

Yang, C.; Ding, X.; Ono, R. J.; Lee, H.; Hsu, L. Y.; Tong, Y. W.; Hedrick, J.; Yang, Y. Y. *Adv. Mater.* 2014, 26, 7346-7351.

Yu, X.; Fan, H.; Wang, L.; Jin, Z. *Angew. Chem. Int. Ed.* 2014, 53, 12600-12604.

B. M. Holzapfel, J. C. Reichert, J. T. Schantz, U. Gbureck, L. Rackwitz, U. Noth, F. Jakob, M. Rudert, J. Groll, D. W. Hutmacher, Adv. Drug Deliv. Rev. 65 (2013) 581.

N. Huebsch, D. J. Mooney, Nature 462 (2009) 426.

R. Langer, D. A. Tirrell, Nature 428 (2004) 487.

M. B. Gorbet, M. V. Sefton, Biomaterials 25 (2004) 5681.

J. M. Anderson, A. Rodriguez, D. T. Chang, Semin. Immunol. 20 (2008) 86.

K. N. Ekdahl, J. D. Lambris, H. Elwing, D. Ricklin, P. H. Nilsson, Y. Teramura, I. A. Nicholls, B. Nilsson, Adv. Drug Deliv. Rev. 63 (2011) 1042.

D. Ricklin, G. Hajishengallis, K. Yang, J. D. Lambris, Nat. Immunol. 11 (2010) 785.

H. J. Busscher, H. C. van der Mei, G. Subbiandoss, P. C. Jutte, J. van den Dungen, S. A. J. Zaat, M. J. Schultz, D. W. Grainger, Sci. Transl. Med. 4 (2012) 10.

B. D. Ratner, Biomaterials 28 (2007) 5144.

E. A. Vogler, C. A. Siedlecki, Biomaterials 30 (2009) 1857.

What is claimed is:

1. A composition, the composition comprising a co-dissolved solution of (a) and (b), wherein:
   (a) is a polymeric binder, wherein the polymeric binder is polymeric dopamine (PDA) and
   (b) is a hydrophilic polymer, wherein the hydrophilic polymer is selected from one or more of: poly(acrylamide) (PAM); poly(N,N-dimethyl acrylamide) (PDMA); poly(N-hydroxymethyl acrylamide) (PHMA); poly(N-hydroxyethyl acrylamide) (PHEA); poly{N-[tris(hydroxymethyl) methyl]acrylamide} (PTHMAM); poly(methacrylamide) (PMA); poly(N-(2-hydroxypropyl)methacrylamide) (PHPMA); poly(N-(3-(methacryloylamino)propyl)-N,N-dimethyl-N-(3-sulfopropyl) ammonium hydroxide) (PMPDSAH); and poly(2-methacryloyloxyethyl phosphorylcholine) (PMPC);
wherein the hydrophilic polymer is a high molecular weight hydrophilic polymer having a molecular weight ≥100,000 daltons and wherein the composition forms a stable mixture when in solution.

2. The composition of claim 1, wherein the composition further comprises:
   (a) a buffer;
   (b) an aqueous solution;
   (c) a water soluble organic solvent; or
   (d) water.

3. The composition of claim 2, wherein: (a) the aqueous solution lacks a salt; (b) the buffer has a pH of between 7 and 12; or (c) the buffer comprises a salt.

4. The composition of claim 1, wherein the ratio of a polymeric binder to hydrophilic polymer in mg/ml is: (a) between 100:1 and 1:100; (b) between 1:1 and 1:30; or (c) between 1:5 and 1:15.

5. The composition of claim 1, wherein the hydrophilic polymer has a number average molecular weight ($M_n$) of:
   (a) at least 100 kDa;
   (b) at least 200 kDa; or
   (c) at least 300 kDa.

6. The composition of claim 1, wherein the hydrophilic polymer is:
   (a) selected from one or more of: poly(acrylamide) (PAM); poly(N,N-dimethyl acrylamide) (PDMA); poly(N-hydroxymethyl acrylamide) (PHMA); poly(N-hydroxyethyl acrylamide) (PHEA); poly{N-[tris(hydroxymethyl) methyl]acrylamide} (PTHMAM); poly(N-(2-hydroxypropyl)methacrylamide) (PHPMA); poly(N-(3-(methacryloylamino)propyl)-N,N-dimethyl-N-(3-sulfopropyl) ammonium hydroxide) (PMPDSAH); poly(carboxybetaine methacrylate) (PCBMA); and poly(2-methacryloyloxyethyl phosphorylcholine) (PMPC);
   (b) selected from one or more of: PAM; PDMA; PHMA; PHEA; and PHPMA; or
   (c) PDMA.

7. A coated substrate, the coated substrate comprising:
   (a) a substrate;
   (b) a polymeric binder, wherein the polymeric binder is selected from one or more of: PDA; and
   (c) a hydrophilic polymer, wherein the hydrophilic polymer is selected from one or more of: PAM, PDMA, PHMA, PHEA, PTHMAM, PMA, PHPMA, PMPDSAH, and PMPC;
wherein the coated substrate comprises a co-dissolved solution of (b) and (c);
wherein the hydrophilic polymer is a high molecular weight hydrophilic polymer having a molecular weight ≥100,000 daltons.

8. The coated substrate of claim 7, wherein the substrate is a plastic, a metal, a ceramic, a carbon based material, a metal oxide, a hydrogel, a biological tissue, a wood or a cement.

9. The coated substrate of claim 7, wherein the substrate is:
   (a) selected from poly(propylene) (PP); poly(urethane) (PU); poly(ethylene) (PE); unplasticized polyvinyl chloride (uPVC); plasticized polyvinyl chloride (pPVC); poly(imide) (PI); ethylene vinyl acetate (EVA); poly(tetrafluoroethylene) (PTFE); titanium dioxide ($TiO_2$), and silicon dioxide ($SiO_2$);
   (b) selected from PP, PU, PE, uPVC, pPVC, PI, EVA, and PTFE; or
   (c) is $TiO_2$ or $SiO_2$.

10. The coated substrate of claim 7, wherein the substrate forms part of an apparatus.

11. The coated substrate of claim 10, wherein the apparatus is selected from: a urinary device; a dental fixture; an artificial joint; a vascular device; a storage device; a microfluidic device; a filtration membrane; a feed tube; or a diagnostic device.

12. The coated substrate of claim 11, wherein:
   (a) the vascular device is selected from a catheter, a lead, and a stent;
   (b) the urinary device is selected from a urine storage device, catheter, and a stent; or
   (c) the filtration membrane is selected from a blood filtration membrane, a water purification membrane, and an air purification membrane.

13. A method of coating a substrate, wherein the substrate is immersed in a solution comprising the composition of claim 1 or the substrate is sprayed with a solution comprising the composition of claim 1.

14. The method of claim 13, wherein the method further comprises one or more of the following:
   (a) drying the substrate;
   (b) applying a further coat of the solution following the drying of the substrate;
   (c) a second drying of the substrate;
   (d) one or more repetitions of the applying a further coat of the solution followed by one or more subsequent drying steps;
   (e) mechanical agitation following immersion in the solution; or
   (f) application of a primer, prior to immersion in or spraying of a solution.

15. The method of claim 14, wherein the drying is in flow of argon gas or a flow of nitrogen gas.

16. The composition of claim 1, wherein the composition is for use as an anti-fouling agent or for use as an anti-adhesion agent.

17. The method of claim 13, wherein the coated substrate reduces biofouling, reduces adhesion or reduces thrombus formation.

* * * * *